United States Patent
Yang et al.

(10) Patent No.: US 11,684,404 B2
(45) Date of Patent: Jun. 27, 2023

(54) METHODS AND DEVICES FOR OPTOACOUSTIC STIMULATION

(71) Applicant: Trustees of Boston University, Boston, MA (US)

(72) Inventors: Chen Yang, Newton, MA (US); Ji-Xin Cheng, Newton, MA (US); Nan Zheng, Allston, MA (US); Yueming Li, Brighton, MA (US); Ying Jiang, Brighton, MA (US); Lu Lan, Allston, MA (US); Linli Shi, Allston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/690,948

(22) Filed: Mar. 9, 2022

(65) Prior Publication Data
US 2022/0287758 A1    Sep. 15, 2022

Related U.S. Application Data

(60) Provisional application No. 63/177,029, filed on Apr. 20, 2021, provisional application No. 63/158,566, filed on Mar. 9, 2021.

(51) Int. Cl.
*A61B 18/04*    (2006.01)
*B01J 19/10*    (2006.01)
(Continued)

(52) U.S. Cl.
CPC ............ *A61B 18/04* (2013.01); *A61B 5/0095* (2013.01); *A61B 18/26* (2013.01); *B01J 19/10* (2013.01);
(Continued)

(58) Field of Classification Search
CPC ....... A61B 18/04; A61B 5/0095; A61B 18/26; A61B 5/0035; A61B 5/0059;
(Continued)

(56) References Cited

U.S. PATENT DOCUMENTS

2013/0310908 A1* 11/2013 Omenetto ............... H01L 35/30
   428/338
2014/0018663 A1    1/2014 Harmer et al.
(Continued)

OTHER PUBLICATIONS

Chen ["Review of Laser-Generated Ultrasound Transmitters and Their Applications to All-Optical Ultrasound Transducers and Imaging", Appl. Sci. 2017, 7, 25; doi:10.3390/app7010025] (Year: 2017).*
(Continued)

*Primary Examiner* — Oommen Jacob
(74) *Attorney, Agent, or Firm* — Burns & Levinson LLP; Steven M. Mills

(57) ABSTRACT

A tapered fiber optoacoustic emitter includes a nanosecond laser configured to emit laser pulses and an optic fiber. The optic fiber includes a tip configured to guide the laser pulses. The tip has a coating including a diffusion layer and a thermal expansion layer, wherein the diffusion layer includes epoxy and zinc oxide nanoparticles configured to diffuse the light while restricting localized heating. The thermal expansion layer includes carbon nanotubes (CNTs) and Polydimethylsiloxane (PDMS) configured to convert the laser pulses to generate ultrasound. The frequency of the ultrasound is tuned with a thickness of the diffusion layer and a CNT concentration of the expansion layer.

23 Claims, 53 Drawing Sheets

(51) Int. Cl.
| | |
|---|---|
| B82Y 40/00 | (2011.01) |
| B82Y 30/00 | (2011.01) |
| A61B 5/00 | (2006.01) |
| A61B 18/26 | (2006.01) |
| A61B 8/00 | (2006.01) |
| A61B 18/22 | (2006.01) |
| G01N 29/24 | (2006.01) |
| G01S 15/89 | (2006.01) |
| F21V 8/00 | (2006.01) |
| G02B 6/02 | (2006.01) |
| G02B 6/34 | (2006.01) |

(52) U.S. Cl.
CPC ............... *B82Y 30/00* (2013.01); *B82Y 40/00* (2013.01); *A61B 5/0035* (2013.01); *A61B 5/0059* (2013.01); *A61B 8/4416* (2013.01); *A61B 8/4483* (2013.01); *A61B 2018/2205* (2013.01); *A61B 2018/2244* (2013.01); *A61B 2018/2261* (2013.01); *A61B 2018/266* (2013.01); *G01N 29/2431* (2013.01); *G01S 15/8968* (2013.01); *G02B 6/004* (2013.01); *G02B 6/021* (2013.01); *G02B 6/02033* (2013.01); *G02B 6/02104* (2013.01); *G02B 6/34* (2013.01)

(58) Field of Classification Search
CPC ................ A61B 8/4416; A61B 8/4483; A61B 2018/2205; A61B 2018/2244; A61B 2018/2261; A61B 2018/266; B01J 19/10; B82Y 30/00; B82Y 40/00; G01N 29/2431; G01S 15/8968; G02B 6/004; G02B 6/02033; G02B 6/021; G02B 6/02104; G02B 6/34; A61N 2007/0026; A61N 2007/0047
See application file for complete search history.

(56) References Cited

U.S. PATENT DOCUMENTS

| | | | | |
|---|---|---|---|---|
| 2014/0046178 | A1* | 2/2014 | Kamalakaran | A61B 17/00 600/424 |
| 2014/0112107 | A1* | 4/2014 | Guo | B06B 1/00 427/596 |
| 2014/0303476 | A1* | 10/2014 | Dogra | A61B 8/08 600/407 |
| 2014/0334005 | A1* | 11/2014 | Omenetto | G02B 1/005 977/773 |
| 2016/0303402 | A1* | 10/2016 | Tyler | A61N 5/062 |
| 2018/0310831 | A1 | 11/2018 | Cheng et al. | |
| 2021/0013551 | A1* | 1/2021 | Zhi | H01M 10/38 |
| 2022/0287758 | A1* | 9/2022 | Yang | A61B 18/04 |

OTHER PUBLICATIONS

Hou ["Carbon-Nanotube-Wrapped Spider Silks for Directed Cardiomyocyte Growth and Electrophysiological Detection" Appl. Mater. Interfaces 2018, 10, 6793-6798 (Year: 2018).*

Reizabal [Optimized silk fibroin piezoresistive nanocomposites for pressure sensing applications based on natural polymers Nanoscale Adv., 2019, 1, 2284-2292 This journal] (Year: 2019).*

Mayberg et al., "Deep Brain Stimulation for Treatment-Resistant Depression," Neuron, vol. 45, pp. 651-660, DOI:10.1016/j.neuron.2005.02.014 (2005).

Mehic, E. et al., "Increased Anatomical Specificity of Neuromodulation via Modulated Focused Ultrasound," PLoS ONE, vol. 9(2):e86939, 13 pps., DOI:10.1371/journal.pone.0086939 (2014).

Micheva, K. et al., "A large fraction of neocortical myelin ensheathes axons of local inhibitory neurons," eLife 2016, 5:e15784, 29 pps., DOI:10.7554/eLife.15784 (2016).

Miller, D. et al., "Sonoporation of cultured cells in the rotating tube Exposure system," Ultrasound in Med. & Biol., vol. 25, No. 1, pp. 143-149, (1999).

Mitragotri, S., "Healing sound: the use of ultrasound in drug delivery and other therapeutic applications," Nature Reviews, vol. 4, pp. 255-260 doi:10.1038/nrd1662 (2005).

Mohammadzadeh, M. et al., "Photoacoustic shock wave emission and cavitation from structured optical fiber tips," Appl. Phys. Lett. 108, 6 pgs., DOI:10.1063/1.4939511 (2016).

Mulik, R. et al., "Localized delivery of low-density lipoprotein docosahexaenoic acid nanoparticles to the rat brain using focused ultrasound," Biomaterials 83, pp. 257-268, DOI:10.1016/j.biomaterials.2016.01.021 (2016).

Nakamura, T. et al., "Synergistic Release of Ca2+ from IP3-Sensitive Stores Evoked by Synaptic Activation of mGluRs Paired with Backpropagating Action Potentials," Neuron, vol. 24, pp. 727-737 (Nov. 1999).

Naor et al., "Ultrasonic neuromodulation," Journal of Neural Engineering, vol. 13, 18 pps., DOI:10.1088/1741-2560/13/3/031003 (2016).

Nguyen, T. et al., "Dependence of cavitation, chemical effect, and mechanical effect thresholds on ultrasonic frequency," Ultrasonics—Sonochemistry 39, pp. 301-306, DOI:10.1016/j.ultsonch.2017.04.037 (2017).

Nicolaides, K. et al., "The Effect of Backing Material on the Transmitting Response Level and Bandwidth of a wideband underwater Transmitting Transducer using 1-3 Piezocomposite Material," Physics Procedia 3, pp. 1041-1045, DOI:10.1016/j.phpro.2010.01.134 (2010).

Noimark, S. et al., "Carbon-Nanotube-PDMS Composite Coatings on Optical Fibers for All-Optical Ultrasound Imaging," Adv. Fund. Mater., vol. 26, pp. 8390-8396, DOI:10.1002/adfm.201601337 (2016).

Noimark, S. et al., "Polydimethylsiloxane Composites for Optical Ultrasound Generation and Multimodality Imaging," Adv. Fund. Mater., vol. 28, 16 pps., DOI:10.1002/adfm.201704919 (2018).

Park, E. et al., "Ultrasound Mediated Transdermal Insulin Delivery in Pigs Using a Lightweight Transducer," Pharmaceutical Research, vol. 24, No. 7, DOI: 10.1007/s11095-007-9306-4 (2007).

Poduval, R. et al., "Optical fiber ultrasound transmitter with electrospun carbon nanotube-polymer composite," Appl. Phys. Lett. 110, 223701, 6 pgs., DOI:10.1063/1.4984838 (2017).

Richardson et al., "Optical Stimulation of Neural Tissue," Healthcare Technology Letters, vol. 7, iss. 3, pp. 58-65, DOI:10.1049/htl.2019.0114 (2020).

Rizzo, J., "Update on Retinal Prosthetic Research: The Boston Retinal Implant Project," J. Neuro-Opthalmology 31, pp. 160-168, DOI:10.1097/WNO.0b013e31821eb79e (2011).

Rosin et al., "Closed-Loop Deep Brain Stimulation is Superior in Ameliorating Parkinsonism," Neuron, vol. 72, pp. 370-384, DOI:10.1016/j.neuron.2011.08.023 (2011).

Shapiro, M. et al., "Infrared light excited cells by changing their electrical capacitance," Nature Communications 3:736, 11 pps., DOI:10.1038/ncomms1742(2012).

Shemesh, O. et al., "Temporally precise single-cell-resolution optogenetics," Nature Neuroscience, vol. 20, pp. 1796-1806, DOI:10.1038/s41593-017-0018-8 (2017).

Shi et al., "A Fiber Optoacoustic Emitter with Controlled Ultrasound Frequency for Cell Membrane Sonoporation at Submillimeter Spatial Resolution," Photoacoustics, 10 pps., DOI:10.1016/j.pacs.2020.100208 (Oct. 2020).

Smith, N. et al., "Perspectives on transdermal ultrasound mediated drug delivery," International Jounral of Nanomedicine 2(4), pp. 585-594 (2007).

Smith, N. et al., "Ultrasound-mediated transdermal transport of insulin in vitro through human skin using novel transducer Designs," Ultrasound in Med. & Biol., vol. 29, No. 2, pp. 311-317, DOI:10.1016/S0301-5629(02)00706-8 (2003).

Song, Y. et al., "Ultrasound-mediated DNA transfer for bacteria," Nucleic Acids Research, vol. 35, No. 19, DOI:10.1093/nar/gkm710, 9 pgs. (2007).

Sun, T. et al., "Closed-loop control of targeted ultrasound drug delivery across the blood-brain/tumor barriers in a rat glioma

(56) References Cited

OTHER PUBLICATIONS model," PNAS (Nov. 13, 2017), E10281-E10290, DOI:10.1073/pnas.1713328114/-/DCSupplemental.
Svanstrom, E., "Analytical photoacoustic model of laser-induced ultrasound in a planar layered structure," Licentiate Thesis, Lulea Univ. of Tech., Dept. of Computer Sci., Electrical & Space Eng., Lulea, Sweden, 100 pgs. (2013).
Szablowski, J. et al., "Acoustically targeted chemogenetics for the non-invasive control of neural circuits," Nature Biomedical Engineering, vol. 2, pp. 475-484, DOI:10.1038/s41551-018-0258-2 (Jul. 2018).
Tufail et al., "Transcranial Pulsed Ultrasound Stimulates Intact Brain Circuits," Neuron, vol. 66, pp. 681-694, DOI:10.1016/j.neuron.2010.05.008 (2010).
Tufail et al., "Ultrasonic neuromodulation by brain stimulation with transcranial ultrasound," Nature Protocols, vol. 6, No. 9, pp. 1453-1470, DOI:10.1038/nprot.2011.371 (2011).
Tyler, W. et al., "Remote Excitation of Neuronal Circuits Using Low-Intensity, Low-Frequency Ultrasound," PLoS ONE, vol. 3, iss. 10, 11 pps., DOI:10.1371/journal.pone.0003511 (2008).
Tyler, W. et al., "Ultrasonic modulation of neural circuit activity," Curr. Opinion in Neurobiology, 50:222-231, DOI:10.1016/j.conb.2018.04.011 (2018).
Wang, L. and Hu, S., "Photoacoustic Tomography: In Vivo Imaging from Organelles to Organs," Science, vol. 335, pp. 1458-1462, DOI:10.1126/science.1216210 (2012).
Wang, L. and Yao, J., "A practical guide to photoacoustic tomography in the life sciences," Nature Methods, vol. 13, No. 8, pp. 627-638, DOI:10.1038/nmeth.3925 (2016).
Wells et al., "Biophysical Mechanisms of Transient Optical Stimulation of Peripheral Nerve," Biophysical Journal, vol. 93, pp. 2567-2580, DOI:10.1529/biophysj.107.104786 (2007).
Xu et al., "Focal infrared neural stimulation with high-field functional MRI: A rapid way to map mesoscale brain connectomes," Sci. Adv., vol. 5:eaau7046, 9 pps. (Apr. 2019).
Ye, P. P. et al., "Frequency dependence of ultrasound neurostimulation in the mouse brain," Ultrasound Med. Biol. 42(7), pp. 1512-1530 (2016).
International Search Report and Written Opinion in Application No. PCT/US22/19569 dated Sep. 1, 2022 (10 pgs.).
Asteriti, S. et al., "Calcium signalling in Drosophila photoreceptors measured with GCaMP6f," Cell Calcium, vol. 65, pp. 40-51, DOI:10.1016/j.ceca.2017.02.006 (2017).
Best, T. et al., "Low Intensity Ultrasound for Promoting Soft Tissue Healing: a Systematic Review of the Literature and Medical Technology," Intern Med Rev (Wash D C). Dec. 2016; 2(11), 9 pgs., DOI:10.18103/imr.v2i11.271.
Blackmore et al., "Ultrasound neuromodulation: a review of results, mechanisms and safety," Ultrasound in Med. & Biol., vol. 45, No. 7, pp. 1509-1536, DOI:10.1016/j.ultrasmedbio.2018.12.015 (2019).
Boon et al., Deep Brain Stimulation in Patients with Refractory Temporal Lobe Epilepsy,: Epilepsia 48(8):1551-1560 (2007).
Boyden et al., "Millisecond-timescale, genetically targeted optical control of neural activity," Nature Neuroscience, vol. 8, No. 9, pp. 1263-1268, DOI:10.1038/nn1-525 (2005).
Cayce et al., "Infrared neural stimulation of human spinal nerve roots in vivo," Neurophotonics, vol. 2, No. 1, 10 pps., DOI:10.1117/1.NPh.2.1.015007 (2015).
Cayce et al., "Infrared neural stimulation of primary visual cortex in non-human primates," Neuroimage, vol. 84, pp. 181-190, DOI:10.1016/j.neuroimage.2013.08.040 (2014).
Chernov et al., "Histological Assessment of Thermal Damage in the Brain following Infrared Neural Stimulation," Brain Stimul., vol. 7, No. 3, pp. 476-482, DOI:10.1016/j.brs.2014.01.006 (2014).
Cohen, J. and Fields, R. D., "Extracellular Calcium Depletion in Synaptic Transmission," Neuroscientist, vol. 10(1), pp. 12-17, DOI:10.1177/1073858403259440 (2004).
Colchester, R. et al., "Laser-generated ultrasound with optical fibres using functionalised carbon nanotube composite coatings," Applied Physics Letters, vol. 104, 5 pgs., DOI:10.1063/1.4873678 (2014).

Csicsvari, J. et al., "Reliability and state dependence of pyramidal cell-interneuron synapses in the hippocampus: an ensemble approach in the behaving rat," Neuron, vol. 21, pp. 179-189 (Jul. 1998).
Dana, H. et al., "High-performance calcium sensors for imaging activity in neuronal populations and microcompartments," Nature Methods, vol. 16, pp. 649-657, DOI:10.1038/s41592-019-0435-6 (2019).
Deffieux, T. et al., "Low-intensity focused ultrasound modulates monkey visuomotor behavior," Current Biology, vol. 23, pp. 2430-2433, DOI:10.1016/j.cub.2013.10.029 (2013).
Desilets, C. et al., "The Design of Efficient Broad-Band Piezoelectric Transducers," IEEE Transactions on Sonics and Ultrasonics, vol. SU-25, No. 3, 11 pgs. (May 1978).
Do Nascimento, V. et al., "Influence of backing and matching layers in ultrasound transducer performance," Proc. SPIE 5035, Medical Imaging 2003: Ultrasonic Imaging and Signal Processing, 12 pgs., DOI:10.1117/12.479924(May 23, 2003).
Escoffre & Bouakaz, eds., "Sonoporation: Concept and Mechanisms," in Therapeutic Ultrasound, Advances in Experimental Medicine and Biology, vol. 880, Chapter 10, 15 pps., DOI 10.1007/978-3-319-22536-4_10 (2016).
Fairand, B. P. and Clauer, A. H., "Laser generation of high-amplitude stress waves in materials," Journal of Applied Physics, vol. 50, pp. 1497-1502, DOI:10.1063/1.326137 (1979).
Fan, C.-H. et al., "Noninvasive, Targeted, and Non-Viral Ultrasound-Mediated GDNF-Plasmid Delivery for Treatment of Parkinson's Disease," Sci. Rep. 6, 19579; 11 pgs., DOI:10.1038/srep19579 (2016).
Fernandez, F. et al., "Differences in the Electrophysiological Properties of Mouse Somatosensory Layer 2/3 Neurons In Vivo and Slice Stem from Intrinsic Sources Rather than a Network-Generated High Conductance State," eNeuro, vol. 5(2), DOI:10.1523/ENEURO.0447-17.2018, 18 pps. (2018).
Ferrara, K., "Driving delivery vehicles with ultrasound," Advanced Drug Delivery Reviews 60 (2008), pp. 1097-1102.
Ferraro, G. et al., "Histologic Effects of External Ultrasound-Assisted Lipectomy on Adipose Tissue," Aesth. Plast. Surg. 32, pp. 111-115, DOI:10.1007/s00266-007-9031-8 (2008).
Folloni, D. et al., "Manipulation of Subcortical and Deep Cortical Activity in the Primate Brain Using Transcranial Focused Ultrasound Stimulation," Neuron 101, pp. 1109-1116, DOI:10.1016/j.neuron.2019.01.019 (2019).
Grunt, S. et al., "Long-term outcome and adverse effects of selective dorsal rhizotomy in children with cerebral palsy: a systematic review," Developmental Medicine & Child Neurology, pp. 490-498, DOI:10.1111/j.1469-8749.2011.03912.x (2011).
Guillermic, R.-M. et al., "A PDMS-based broadband acoustic impedance matched material for underwater applications," Ultrasonics 94, pp. 152-157, DOI:10.1016/j.ultras.2018.10.002 (2018).
Ha, G. and Cheong, E., "Spike Frequency Adaptation in Neurons of the Central Nervous System," Exp. Neurobiol., vol. 26(4), pp. 179-185, DOI:10.5607/en.2017.26.4.179 (2017).
Houweling, A. and Brecht, M., "Behavioural report of single neuron stimulation in somatosensory cortex," Nature Lett., vol. 451, pp. 65-69, DOI:10.1038/nature06447 (2008).
Ineichen et al., "Understanding the Effects and Adverse Reactions of Deep Brain Stimulation: Is It Time for a Paradigm Shift Toward a Focus on Heterogenous Biophysical Tissue Properties Instead of Electrode Design Only?" Frontiers in Human Neuroscience, vol. 12, article 468, 13 pps., DOI:10.3389/fnhum.2018.00468 (2018).
Izzo et al., "Laser Stimulation of the Auditory Nerve," Lasers in Surgery and Medicine, vol. 38, pp. 745-753, DOI:10.1002/lsm.20358 (2006).
Jiang, Y. et al., "Optoacoustic brain stimulation at submillimeter spatial precision," Nature Communications 11:881, 9 pgs., DOI:10.1038/s41467-020-14706-1 (2020).
Karshafian, R. et al., "Sonoporation by ultrasound-activated microbubble contrast agents: effect of acoustic exposure Parameters on cell membrane permeability and cell viability," Ultrasound in Med. & Biol., vol. 35, No. 5, pp. 847-860, DOI:10.1016/j.ultrasmedbio.2008.10.013 (2009).

(56) References Cited

OTHER PUBLICATIONS

Kim, C. et al., "Integration of optogenetics with complementary methodologies in systems neuroscience," Nature, vol. 18, pp. 222-235, DOI:10.1038/nrn.2017.15 (2017).

Kinoshita, M. et al., "Noninvasive localized delivery of Herceptin to the mouse brain by MRI-guided focused ultrasound-induced blood-brain barrier disruption," PNAS, vol. 103, No. 31, (Aug. 1, 2006) DOI:10.1073/pnas.0604318103.

Kodandaramaiah et al., "Automated whole-cell patch-clamp electrophysiology of neurons in vivo," Nature Methods, vol. 9, No. 6, pp. 585-590, DOI:10.1038/nmeth.1993 (2012).

Krasovitski, B. et al., "Intramembrane cavitation as a unifying mechanism for ultrasound-induced bioeffects," PNAS, vol. 108, No. 8, pp. 3258-3263, DOI:10.1073.pnas.1015771108 (2011).

Kubanek, J., "Neuromodulation with transcranial focused ultrasound," Neurosurg. Focus, vol. 44(2):e14, 12 pps., DOI:10.3171/2017.11.FOCUS17621 (2018).

Lammertink, B. et al., "Duration of ultrasound-mediated enhanced plasma membrane permeability," International Journal of Pharmaceutics, vol. 482, pp. 92-98, DOI:10.1016/j.ijpharm.2014.12.013 (2014).

Lammertink, B. et al., "Dynamic Fluorescence Microscopy of Cellular Uptake of Intercalating Model Drugs by Ultrasound-Activated Microbubbles," Molecular Imaging and Biology 19, pp. 683-693, DOI:10.1007/s11307-016-1042-x (2017).

Lee, T. et al., "Efficient Photoacoustic Conversion in Optical Nanomaterials and Composites," Adv. Optical Mater., 6:1800491, 30 pgs., DOI:10/1002/adom.201800491 (2016).

Legon et al., "Transcranial focused ultrasound modulates the activity of primary somatosensory cortex in humans," Nature Neuroscience, vol. 17, No. 2, pp. 322-332, DOI:10.1038/nn.3620 (2014).

Lentacker, I. et al., "Understanding ultrasound induced sonoporation: Definitions and underlying mechanisms," Advanced Drug Delivery Reviews, vol. 72, pp. 49-64, DOI:10.1016/j.addr.2013.11.008 (2013).

Lethiecq, M. et al., "Piezoelectric transducer design for medical diagnosis and NDE," Piezoelectric and Acoustic Materials for Transducer Applications, Springer, 2008, pp. 191-215.

LeWitt, P. et al., "AAV2-GAD gene therapy for advanced Parkinson's disease: a double-blind, sham-surgery controlled, randomised trial," Lancet Neurol. 10, pp. 309-319, DOI:10.1016/s1474-4422(11)70039-4 (2011).

Li, C.-Y. et al., "Burst Spiking of a Single Cortical Neuron Modifies Global Brain State," Science 324(5927), pp. 643-646, DOI:10.1126/science.1169957 (May 2009).

Li, G-F. et al., "Improved Anatomical Specificity of Non-invasive Neuro-stimulation by High Frequency (5 MHz) Ultrasound," Nature Scientific Reports 6:24738, 11 pps., DOI:10.1038/srep24738 (2016).

Liang, H-D. et al., "Sonoporation, drug delivery, and gene therapy," Proc. IMechE, vol. 224, part H: J. Engineering in Medicine, pp. 343-361, DOI:10.1243/09544119JEIM565 (Jul. 2009).

Long, L. et al., "Treatment of Parkinson's disease in rats by Nrf2 transfection using MRI-guided focused ultrasound delivery of nanomicrobubbles," Biochemical and Bophysical Research Communications 482, pp. 75-80, DOI:10.1016/j.bbrc.2016.10.141 (2017).

Loudin, J. et al., "Design of a High-resolution optoelectronic retinal prosthesis," Proc. of SPIE, vol. 7163, DOI:10.1088/1741-2560/2/1/012 (Apr. 2005).

Lyu, Y. et al., "Semiconducting Polymer Nanobioconjugates for Targeted Photothermal Activation of Neurons," J. Am. Chem. Soc., vol. 138, pp. 9049-9052, DOI:10.1021/jacs.6b05192 (2016).

Mahmud, M. and Vassanelli, S., "Differential modulation of excitatory and inhibitory neurons during periodic stimulation," Frontiers in Neuroscience, vol. 10, article 62, 12 pps., DOI:10.3389/fnins.2016.00062 (2016).

Mallet, L. et al., "Stimulation of subterritories of the subthalamic nucleus reveals its role in the integration of the emotional and motor aspects of behavior," PNAS, vol. 104, No. 25, pp. 10661-10666, DOI:10.1073/pnas.0610849104 (2007).

\* cited by examiner

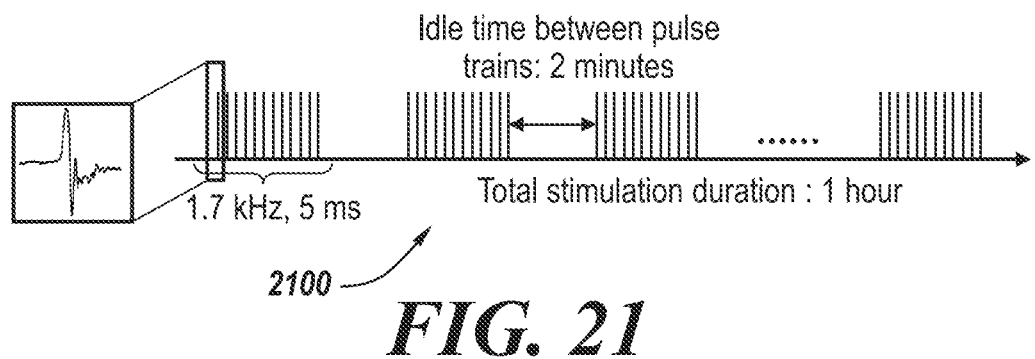
FIG. 21
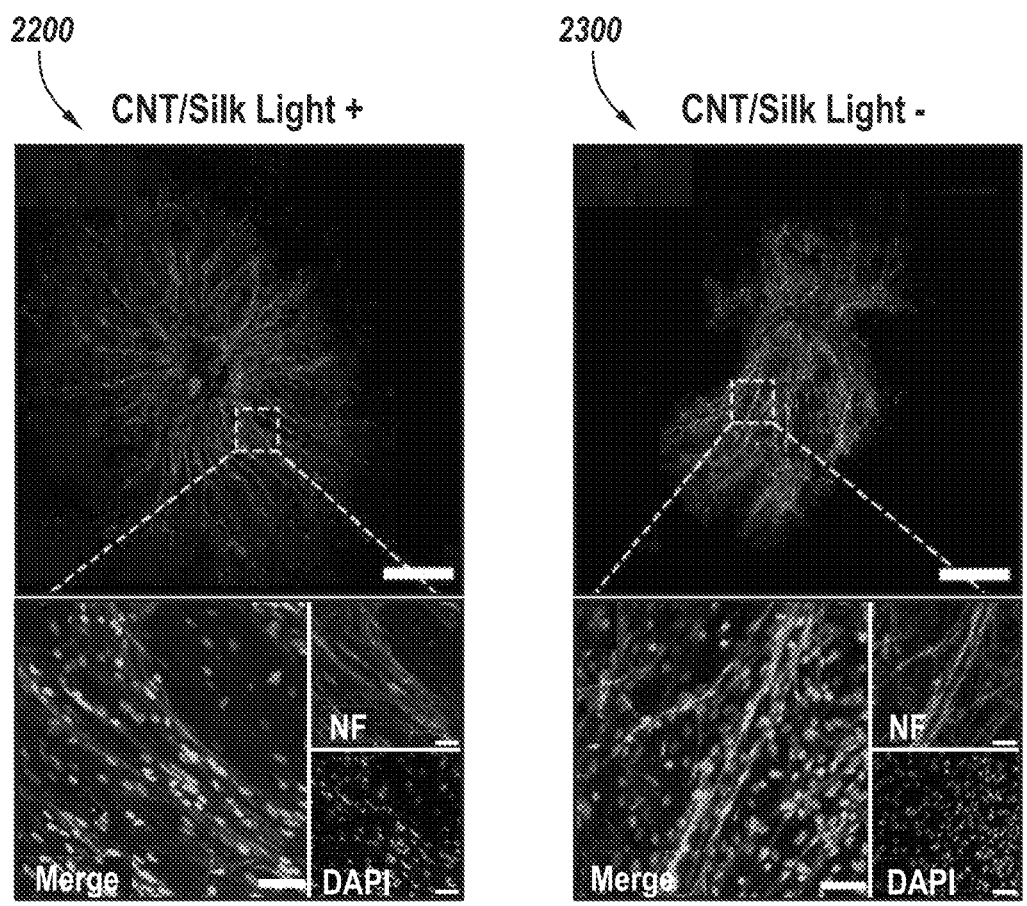
FIG. 22  FIG. 23

Excitatory pyramidal cell (5 µm) (-75 mV)

Excitatory pyramidal cell (10 µm) (-75 mV)

Inhibitory interneuron (5 μm) (-75 mV)

Inhibitory interneuron (5 μm) (-40 mV)

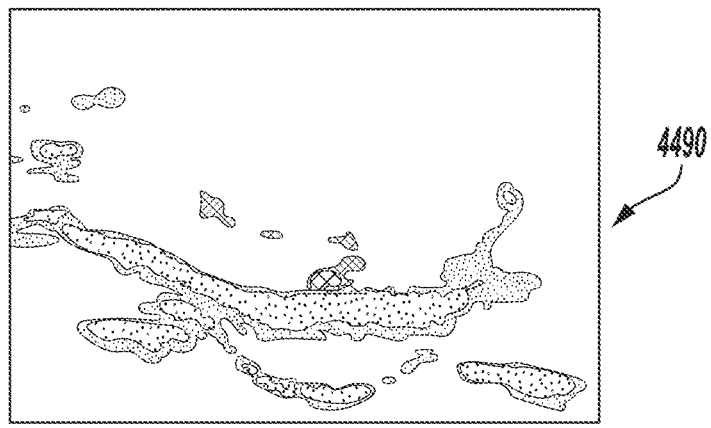
FIG. 44I
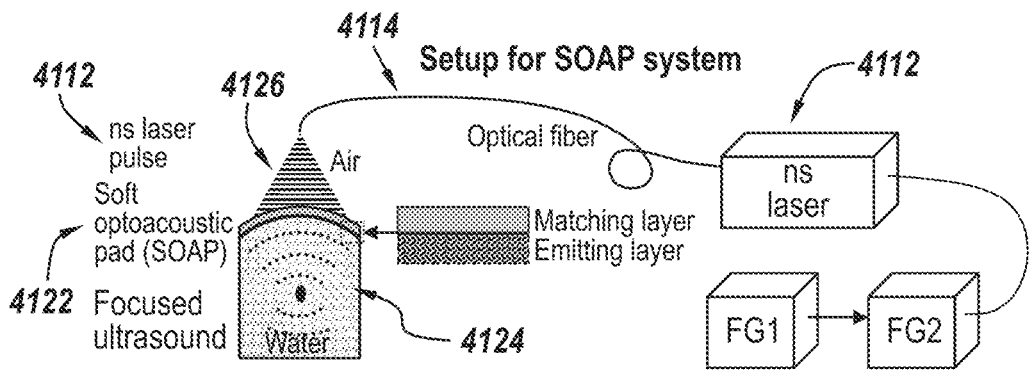
FIG. 45
| | Diameter | Focal length |
|---|---|---|
| Human subject | 30 mm | 25 mm |
| Mouse | 5 mm | 3 mm |
FIG. 46

Ultrasound wave form with different thicknesses

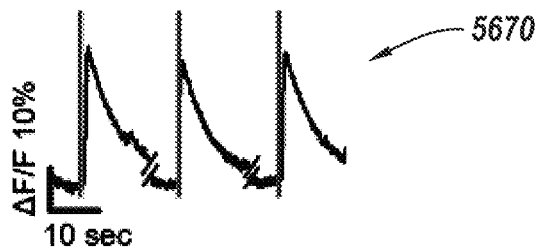
FIG. 56G
| Device | Frequency (MHz) | $I_{SPPA}$ (W/cm$^2$) | Duration (s) | Total energy (J/cm$^2$) |
|---|---|---|---|---|
| SOAP | 15 | $2.35 \times 10^5$ | $0.26 \times 10^{-6}$ | 0.06 |
| Transducer | 0.5 | $3.02 \times 10^4$ | 0.5 | $1.5 \times 10^4$ |
| Transducer[31] | 0.3 | 15 | 0.5 | 7.5 |
FIG. 57
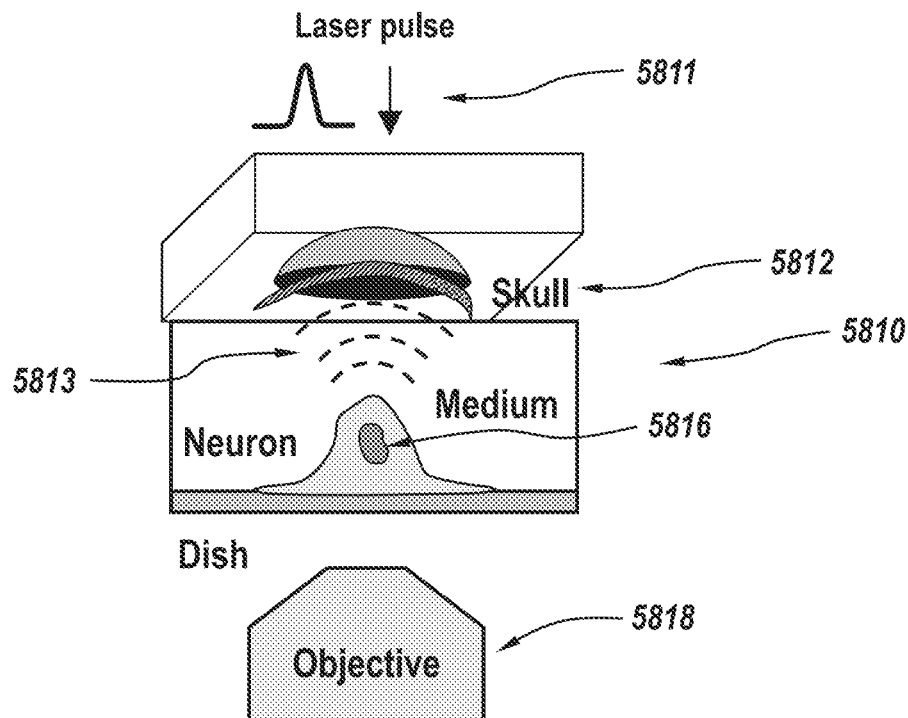
FIG. 58A

METHODS AND DEVICES FOR OPTOACOUSTIC STIMULATION

CROSS-REFERENCE TO RELATED APPLICATIONS

The present application claims the benefit of provisional application No. 63/158,566, filed Mar. 9, 2021, and provisional application No. 63/177,029, filed Apr. 20, 2021, the entire contents of which applications are incorporated herein by reference.

STATEMENT OF GOVERNMENT SUPPORT

This invention was made with Government support under Grant number NS109794 awarded by the NIH. The Government has certain rights in this invention.

BACKGROUND

1. Technical Field

The present disclosure is related to optoacoustic stimulation, in particular, to devices and methods for manipulating and administering optoacoustic stimulation for biotherapies.

2. Discussion of Related Art

Focused ultrasound has attracted great attention in minimally invasive therapeutic and mechanism studies. Frequencies below 1 MHz are preferable for high-efficiency biomodulation. However, the poor spatial confinement of several millimeters and large device diameter of ~25 mm of typical sub-MHz ultrasound technology suffers from the diffraction limit, severely hindering its further applications. Efforts have been made to fabricate miniaturized low frequency transducers, including low-frequency flex tensional resonators, tonpilz transducers, and thickness-type resonators. However, fabrication of these transducers with millimeter-scale lateral dimensions is considered challenging and expensive. In addition to its large device size, transducer-based focus ultrasound technology suffers from large diffraction limited focal volume at millimeter scale for an ultrasound of a few hundred kHz.

SUMMARY

According to one aspect, a tapered fiber optoacoustic emitter is provided. The emitter includes a nanosecond laser configured to emit laser pulses and an optic fiber. The optic fiber includes a tip with a coating configured to convert light to ultrasound. The tip coating can include a diffusion layer and a thermal expansion layer or a single thermal expansion layer. The diffusion layer includes epoxy and zinc oxide nanoparticles configured to diffuse the light while restricting localized heating. The thermal expansion layer includes graphite and Polydimethylsiloxane (PDMS), or carbon nanotubes (CNTs) and PDMS configured to convert the laser pulses to generate ultrasound. The frequency of the ultrasound is tuned with a thickness of the diffusion layer and a CNT concentration of the expansion layer.

In some exemplary embodiments, the ultrasound comprises omnidirectional acoustic waves generated locally at the tip through the optoacoustic effect when excited by the laser pulses. The omnidirectional acoustic waves are localized within a sub-100 micron distance from the tip. The omnidirectional acoustic waves are configured to activate single neurons. Further, the omnidirectional acoustic waves allow for optoacoustic stimulation and simultaneous monitoring of cell response using whole cell patch clamp recording.

In some exemplary embodiments, the device further comprises tuning the frequency to induce cell membrane sonoporation in effected cells. The frequency of the ultrasound is tuned to provide controllable frequencies in the range of 0.083 MHlz-5.500 MHz. Additionally, the coating can be a single layer nano-composite mixed from 5% to 15% (w/w) multiwall carbon nanotube in Polydimethylsiloxane.

According to another aspect, a method of operating a tapered fiber optoacoustic emitter (TFOE) includes emitting laser pulses with a nanosecond laser and guiding the laser pulses with an optic fiber having a tip, the tip coated with a diffusion layer comprising epoxy and zinc oxide and a thermal expansion layer, or a single thermal expansion layer comprising carbon nanotubes (CNTs) and Polydimethylsiloxane (PDMS). The method further includes diffusing the laser pulses while restricting localized heating, with the diffusion layer; converting the diffused light to generate ultrasound, with the thermal expansion layer; and tuning a frequency of the ultrasound with a thickness of the diffusion layer and a CNT concentration in the expansion layer.

In some exemplary embodiments, the ultrasound comprises omnidirectional acoustic waves generated locally at the tip through the optoacoustic effect when excited by the laser pulses. The omnidirectional acoustic waves are localized within a sub-100 micron distance from the tip. The omnidirectional acoustic waves are configured to activate single neurons. Further, the omnidirectional acoustic waves allow for optoacoustic stimulation and simultaneous monitoring of cell response using whole cell patch clamp recording.

In some exemplary embodiments, the device further comprises tuning the frequency to induce cell membrane sonoporation in effected cells. The frequency of the ultrasound is tuned to provide controllable frequencies in the range of 0.083 MHz-5.500 MHz. Additionally, the coating can be a single layer nano-composite mixed from 5% to 15% (w/w) multiwall carbon nanotube in Polydimethylsiloxane.

According to another aspect, a method of stimulating cells via an optoacoustic material is provided. The method includes providing the optoacoustic material, the optoacoustic material having optical absorbers and an expansion matrix configured to generate an ultrasound; embedding the optoacoustic material to a fibroin hydrogel to form an optoacoustic film, the fibroin hydrogel configured to stimulate neural growth in response to the ultrasound; and generating the ultrasound by emitting laser pulses to the optoacoustic film such that the fibroin stimulates neural growth in response to the ultrasound.

In some exemplary embodiments, the ultrasound comprises omnidirectional acoustic waves generated locally at the tip through the optoacoustic effect when excited by the laser pulses. The omnidirectional acoustic waves are localized within a sub-100 micron distance from the tip. The omnidirectional acoustic waves are configured to activate single neurons. Further, the omnidirectional acoustic waves allow for optoacoustic stimulation and simultaneous monitoring of cell response using whole cell patch clamp recording.

In some exemplary embodiments, the method further comprises generating the frequency of the ultrasound involves modifying acoustic damping and light absorption performance to further induce cell membrane sonoporation with frequency dependent efficiency. The frequency of the ultrasound is tuned to provide controllable frequencies in the range of 0.083 MHz-5.500 MHz. Additionally, the fibroin hydrogel can include silk.

According to another aspect, a method of operating a tapered fiber optoacoustic emitter (TFOE) to stimulate cells is provided. The method includes emitting laser pulses with a nanosecond laser and guiding the laser pulses with an optic fiber having a tip. The method then includes embedding CNT into a fibroin hydrogel to form an optoacoustic film, the fibroin hydrogel configured to stimulate neural growth in response to ultrasound.

In some exemplary embodiments, the ultrasound comprises omnidirectional acoustic waves generated locally at the tip through the optoacoustic effect when excited by the laser pulses. The omnidirectional acoustic waves are localized within a sub-100 micron distance from the tip. The omnidirectional acoustic waves are configured to activate single neurons. Further, the omnidirectional acoustic waves allow for optoacoustic stimulation and simultaneous monitoring of cell response using whole cell patch clamp recording.

In some exemplary embodiments, the device further comprises converting the diffused light to generate ultrasound involves modifying acoustic damping and light absorption performance to further induce cell membrane sonoporation with frequency dependent efficiency. The frequency of the ultrasound is tuned to provide controllable frequencies in the range of 0.083 MHz-5.500 MHz. Additionally, the coating can be a single layer nano-composite mixed from 5% to 15% (w/w) multiwall carbon nanotube in Polydimethylsiloxane.

In some exemplary embodiments, the device further comprises the tip being coated with a diffusion layer comprising epoxy and zinc oxide. The diffusion layer diffuses the laser pulses while restricting localized heating.

In some exemplary embodiments, the device further comprises the tip being coated with a thermal expansion layer comprising carbon nanotubes (CNTs) and Polydimethylsiloxane (PDMS). The thermal expansion layer converts the diffused light to generate ultrasound such that the fibroin stimulates neural growth in the cells in response to the ultrasound. In some exemplary embodiments, the fibroin hydrogel includes silk.

According to another aspect, a device for high-precision cellular modulation via the optoacoustic effect is presented. In some exemplary embodiments, this device comprises a tapered fiber optoacoustic emitter. The device includes a nanosecond laser which can be configured to emit laser pulses and an optic fiber with a tip. The optic fiber can be configured to guide the laser pulses and can have a coating including a thermal expansion layer. The thermal expansion layer can include carbon nanotubes (CNTs) and Polydimethylsiloxane (PDMS) configured to convert the laser pulses to generate ultrasound. Embedding CNT into a fibroin hydrogel can thereby form an optoacoustic film. The fibroin hydrogel can further be configured to stimulate neural growth in response to ultrasound. The frequency of the ultrasound can be tuned with a thickness of the CNT concentration of the expansion layer.

According to some exemplary embodiments, the device further comprises the tip including a diffusion layer. The diffusion layer can include epoxy and zinc oxide nanoparticles configured to diffuse the light while restricting localized heating. The frequency of the ultrasound can be tuned with a thickness of the diffusion layer.

According to some exemplary embodiments, the optoacoustic film of the device can be flat. According to some exemplary embodiments, the optoacoustic film of the device can be curved. According to some exemplary embodiments, the curved optoacoustic film generates a focused ultrasound for non-invasive modulation.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings.

FIG. 2A provides an illustration of the ultrasound signals in time domain from TFOEs fabricated with diffusion layer (ZnO/Epoxy) of 36-100 μm and absorption/thermal expansion layer (CNTs/PDMS) of 109±24 μm. FIG. 2B is a graph of an ultrasound produced by TFOEs in accordance with the subject technology, and FIG. 2C is another graph of the frequency domain of an ultrasound produced by TFOEs in accordance with the subject technology. FIG. 2D is a graph of peak frequency by TFOE thickness for a TFOE in accordance with the subject technology.

FIG. 4A is a graph indicating normalized frequency spectrum for TFOEs with a different thermal expansion layers. FIG. 4B is a graph of peak frequency plotted as a function of CNTs/PDMS concentration.

FIG. 5A is a schematic of the detection. FIG. 5B is a graph of the acoustic peak to peak amplitude detected at angles 0°, ±25°, ±50°, and ±75°. FIG. 5C is a graph of the angle dependence of acoustic peak-to-peak amplitude. FIG. 5D is a graph of the frequency spectra for acoustic signals detected at these angles.

FIG. 6A is a schematic of laser pulse tone bursts. FIG. 6B is a graph of temperature change at the TFOE tip during TFOE treatment. FIG. 6C is a graph of optoacoustic signals in time domain from TFOEs. FIG. 6D is a graph of averaged fluorescence intensity changing dynamics of 30 cells upon the treatment of TFOEs with varied frequencies for 10 min. FIG. 6E includes images of fluorescence imaging of TFOE treated regions. FIG. 6F includes images of fluorescence imaging of TFOE treated group and control group. FIG. 6E is a graph of a comparison of fluorescence intensity change between TFOE treated group and control group.

FIG. 21 is a schematic of photoacoustic stimulation when applied to rat dorsal root ganglion explants over time. FIG. 22 is an image of CNT/Silk light+. FIG. 23 is an image of CNT/Silk light−.

FIGS. 34A and 34B are fluorescence images and calcium traces in sparse population stimulated by TFOE with a laser duration of 50 milliseconds and 1 millisecond, respectively. FIG. 34C are max ΔF/F images of one neuron undergone repeated TFOE stimulation 3 times. FIG. 34D are images of the sequential stimulation of 3 neurons.

FIGS. 35A-C are fluorescence images of GCaMP6f expressing neurons before and after TFOE stimulation with a single pulse.

FIGS. 36A and 36B are before and after images of TFOE evoked neurites activation with calcium wave propagating along neuron network. FIG. 36C is an image of ΔF/F of calcium signal at 4 s after laser onset. FIG. 36D is a graph of calcium traces of targeted area, neuron 1 and neuron 2 and 3, as labeled in 36A. FIG. 36E is an image of multipolar neuron stimulated with a TFOE selectively targeting the axon and dendrites. FIGS. 36F-36H are images of maximum ΔF of calcium signal upon stimulation of different areas. FIG. 36I is a graph of calcium traces measured at the targeted neurites as labeled in 36E. FIG. 36J is a graph of calcium traces measured at the soma upon stimulation of different neurites.

FIGS. 37A-B are images of two photon imaging of patch clamp integrated with TFOE in a mouse brain slice targeting GAD2-tdTomato negative pyramidal neurons and GAD2-tdTomato positive inhibitory interneurons, respectively. FIGS. 37C and 37D are graphs of membrane voltage response in an excitatory pyramidal cell upon TFOE stimulation of 5 milliseconds at a distance of ~5 µm (FIG. 37C) and ~10 µm (FIG. 37D), respectively. FIGS. 37E and F are graphs of voltage response in an inhibitory interneuron upon TFOE stimulation at ~5 µm at the membrane voltages of −75 mV (FIG. 37E) and −40 mV (FIG. 37F), respectively.

FIG. 45 is a schematic of the setup dynamic for the SOAP system. FIG. 46 is a table of the human and mouse subject diameter and focal length parameters.

FIG. 54A is a schematic illustration of optoacoustic effect and geometric design of SOAP. FIG. 54B is a plot of the relationship between numerical aperture and lateral resolution. FIG. 54C is an image of the acoustic field generated by SOAP in k-wave simulation with designed geometry. FIG. 54D contains four images of material SOAP with the same geometric design. FIG. 54E is an SEM image of CS-PDMS SOAP cross-section. FIG. 54F is an image of spatial distribution of PDMS and CS in the mixture by SRS and photothermal imaging. FIG. 54G is a graph of the waveforms of 4 material SOAPs with the same laser energy input. FIG. 54H is a graph of the frequency spectrums of 4 material SOAPs.

FIG. 55A is a schematic of the experimental setup for characterizing ultrasound generated by SOAP with a needle hydrophone. FIG. 55B is a graph of the normalized acoustic waveform generated by SOAP without and with mouse skull. FIG. 55C is a graph of the lateral resolution of OFUS without and with mouse skull. FIG. 55D is a graph of the axial resolution of OFUS without and with mouse skull. FIGS. 55E-55F are images of the SOAP-generated ultrasound propagation without (55E) and with (55F) skull.

FIGS. 56A-56G illustrate cultured neurons stimulated by OFUS delivered by SOAP in vitro. FIG. 56A is a schematic of direct in vitro stimulation experimental setup. FIG. 56B is a set of images detailing neurons before and after stimulation. FIG. 56C is a graph of averaged calcium traces of a transient dynamic. FIG. 56D is a graph of averaged calcium traces of a prolonged dynamic of OFUS stimulation. FIG. 56E is a graph detailing statistics of the threshold energy of the transient and prolonged stimulation. FIG. 56F is a set of images detailing maximum ΔF/F image of repeated stimulation for safety demonstration. FIG. 56G is a graph detailing calcium traces of repeated stimulation in 56E.

FIG. 57 is a table including the experimental conditions and total energy to evoke similar amplitude of neuron response.

FIGS. 58A-58D illustrate transcranial stimulation by OFUS delivered by SOAP in vitro. FIG. 58A is a schematic of transcranial in vitro stimulation experimental setup. FIG. 58B is a set of images of neurons before and after transcranial stimulation. FIG. 58C is a graph of averaged calcium response trace of transcranial OFUS stimulation. FIG. 58D is a graph detailing statistics of threshold energy of direct and transcranial stimulation with single pulse.

FIG. 59A is a schematic of experimental setup of OFUS stimulation in vivo. FIG. 59B is a set of images of c-Fos and DAPI staining within the stimulation and control area. FIG. 59C is a graph with statistical analysis for percentage of c-Fos positive neurons. FIG. 59D is a representative EMG recording of 2 s OFUS stimulation and no light control group. FIG. 59E is a representative EMG signal after band-pass filter and full-wave rectifier and envelope. FIG. 59F is a set of images detailing histology results after stimulation in vivo for safety evaluation.

DETAILED DESCRIPTION

Figure 1A:
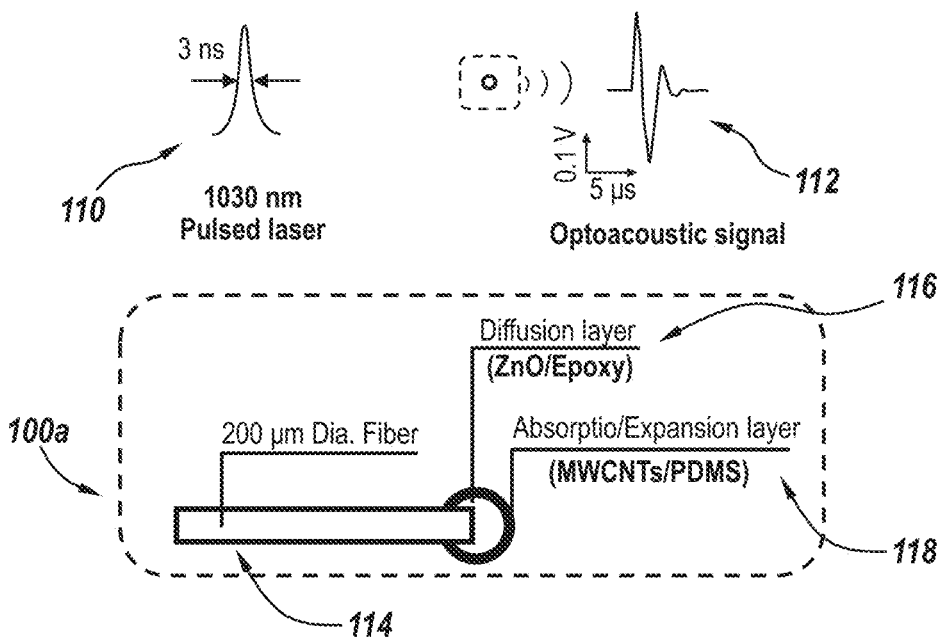
FIG. 1A is a schematic diagram of optoacoustic effect and the design of a two layer fiber-based optoacoustic emitter (TFOE, or TFOE).

According to the device and method of the present disclosure, an optoacoustic emitter with a controllable frequency spectrum targeting the frequency range of sub-MHz is provided.

As an emerging technology, transcranial focused ultrasound has been demonstrated to successfully evoke motor responses in mice, rabbits, and sensory/motor responses in humans. Yet, the spatial resolution of ultrasound does not allow for high-precision stimulation. The present disclosure presents a TFOE for optoacoustic stimulation of neurons with an unprecedented spatial resolution of 20 microns, enabling selective activation of single neurons or subcellular structures, such as axons and dendrites. A single acoustic pulse of 1 microsecond converted by the TFOE from a single laser pulse of 3 nanoseconds is shown as the shortest acoustic stimuli so far for successful neuron activation. The highly localized ultrasound generated by the TFOE made it possible to integrate the optoacoustic stimulation and highly stable patch clamp recording on single neurons. Direct measurements of electrical response of single neurons to acoustic stimulation, which is difficult for conventional ultrasound stimulation, have been demonstrated for the first time. By coupling TFOE with ex vivo brain slice electrophysiology, the present disclosure unveils cell-type-specific response of excitatory and inhibitory neurons to acoustic stimulation. These results demonstrate that TFOE is a non-genetic single-cell and sub-cellular modulation technology, which could shed new insights into the mechanism of neurostimulation.

Neuromodulation at high spatial resolution poses great significance in advancing fundamental knowledge in the field of neuroscience, as firing of a small population or even single neurons can specifically alter animal behavior or brain state. Clinically, precise neural stimulation lays the foundation for procedures such as retinal stimulation and selective dorsal rhizotomy, where selective activation of a small population or single neurons and axon fibers is desired. Historically, electrical stimulation has been the most important technique for neuromodulation. Deep brain stimulation, as the most prescribed neuromodulation method clinically, has been used for treating neurological and psychiatric disorders, such as Parkinson's Disease, depression, and epilepsy. However, the spatial resolution of electrical stimulation is limited by the spread of the electric current, which could distribute over several millimeters and outside of the area of targeting. Providing high spatial precision and cell specificity, optogenetics has been shown as a powerful method of modulating population neural activities in rodents. Yet, the requirement of viral infection makes it challenging to be applied in humans. Toward non-genetic stimulation, photothermal neural stimulations based on light absorption of water has been reported, and it has attracted increasing interest in basic science and translational application. In infrared photothermal neural stimulation (INS), near-infrared light between 1.5 and 2 μm in wavelength is delivered through a fiber and converted into temperature increase in water with sub-millimeter precision, where the associated heating raises a significant concern of tissue damage. As a rapidly growing modality, focused ultrasound has been harnessed in a myriad of brain neuromodulation applications, given its non-invasive nature with a deep penetration depth. However, ultrasound, with a focus limited by the acoustic wave diffraction, offers a limited spatial resolution at the level of several millimeters, which hinders the study of specific brain regions. Additionally, since the ultrasound field easily disrupts the gigaOhm seals, it is challenging to integrate ultrasound stimulation with whole-cell patch-clamp electrophysiology, which is the gold standard technique for high-fidelity analysis of the biophysical mechanisms of neural membrane and ion channels.

The fiber-based optoacoustic converter of the present disclosure exploits the optoacoustic effect, absorbing pulsed light and producing an ultrasound wave, and achieves neural stimulation in vitro and in vivo at submillimeter spatial resolution. The miniaturized tapered fiber optoacoustic emitter (TFOE) is capable of generating >57 kPa pressure with a spatial confinement around 20 μm, which offers an unprecedented high spatial resolution for ultrasound stimulation. The significant advancement of TFOE in both spatial resolution and optoacoustic conversion efficacy are achieved based on the following innovative designs. First, instead of using a commercial multimode fiber with a diameter of 200 microns as in earlier work, the present disclosure provides a developed controlled tapering strategy and reproducibly tapered the fibers to a tip diameter as small as 20 μm. Second, a new deposition method was developed to achieve uniform and controllable coating thickness of ~10 micron on the small 20-micron fiber tip. Third, instead of using graphite powder in epoxy as a converter, the methods and devices of the present disclosure apply carbon nanotubes (CNT) embedded in a Polydimethylsiloxane (PDMS) matrix with improved solubility, which allows highly efficient optoacoustic signal generation from the tapered fiber tip with an increase in the conversion efficiency by one order of magnitude and prevents light leak from the thin 20 micron coating.

According to the embodiments of the present disclosure, using TFOE pushes spatial and temporal resolution of neuron stimulation. Specifically, single cell stimulations and subcellular stimulation of axons and dendrites is demonstrated. Single acoustic pulse with duration of 1 microsecond achieved neuron stimulation, which was found as the shortest duration of acoustic stimuli. Importantly, the near field acoustic wave generated by TFOE allowed optoacoustic stimulation with simultaneously monitoring cell response using whole cell patch clamp recording, which had been reported as a challenge for traditional ultrasound. The present disclosure reveals cell-type specific response to acoustic stimulation for excitatory and inhibitory neurons. This disclosure shows the exciting potential of TFOE as a platform technology for non-genetic high-precision stimulation of the neural system, and as a tool for investigations into the mechanisms of acoustic neural stimulation and MRI compatible clinical application.

As introduced, optoacoustic stimulation, in which a pulsed excitation light is absorbed by materials of interest, resulting in transient heating, material compression and expansion, and subsequently pressure change, is a novel way to generate ultrasound. Notably, designing and coating the fiber tip with two distinct functional layers: an optical diffusion layer and a thermal expansion layer, permits the delivery of sufficient ultrasound intensity and control of the peak frequency and bandwidth needed for cell modulation. By integrating the frequency control ability of both the diffusion layer and the absorption/thermal expansion layer, the present disclosure achieves fine tuning of the frequency within the sub-MHz range as well as frequency beyond 1 MHz.

In this way, the TFOE delivers sub-millimeter high special precision ultrasound with adjustable frequency (for example, 0.083 MHz-5.500 MHz) to deliver membrane impermeable small molecules into living cells via a sonoporation effect. With a greater deliver efficiency of Sytox performed under sub-MHz frequency compared to frequency above 1 MHz, the present disclosure successfully compromises between sub-MHz frequency and sub-millimeter precision to provide broad biomedical applications, such as, region-specific drug delivery, gene transfection, and localized neuron stimulation.

Figure 1B:
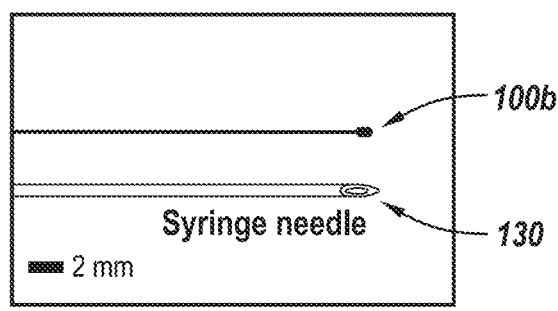
FIG. 1B is a side view of a fiber-based emitter and a syringe needle.
Figure 1C:
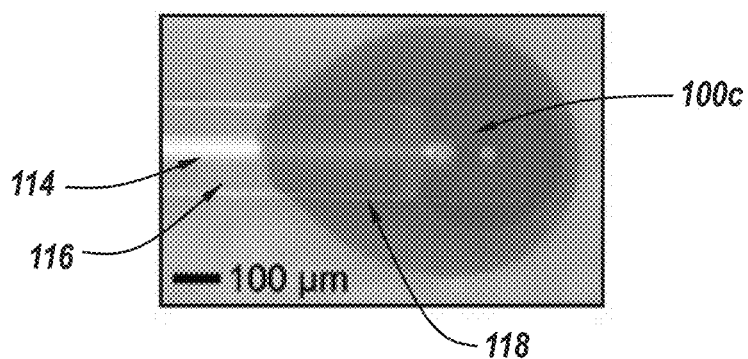
FIG. 1C is a side view of a fabricated TFOE.
Figure 1D:
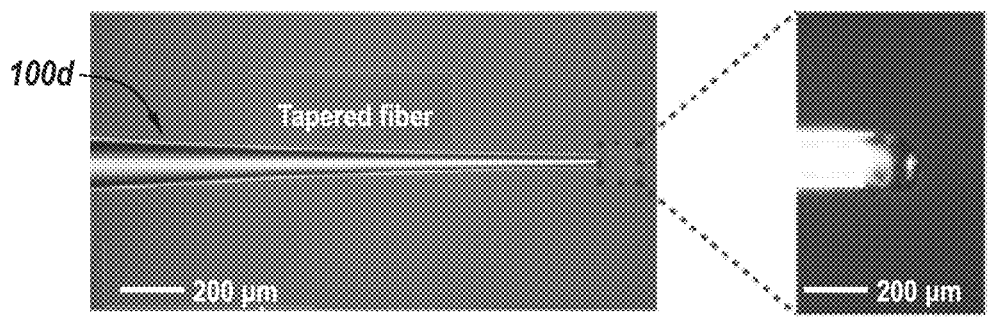
FIG. 1D illustrates a multiwall CNT/PDMS mixture as coating material casted on a metal mesh followed by a punch-through method to coat the tapered fiber.
Figure 1E:
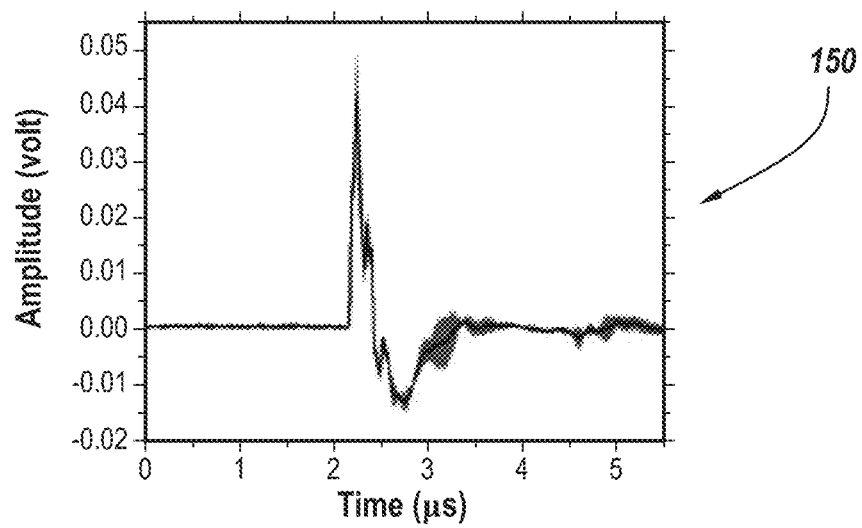
FIGS. 1E and 1F illustrate representative acoustic signal generated by a TFOE in time domain, and frequency domain, respectively, with the shaded area in 1E indicating standard deviation taken from three measurements from the same TFOE.
Figure 1F:
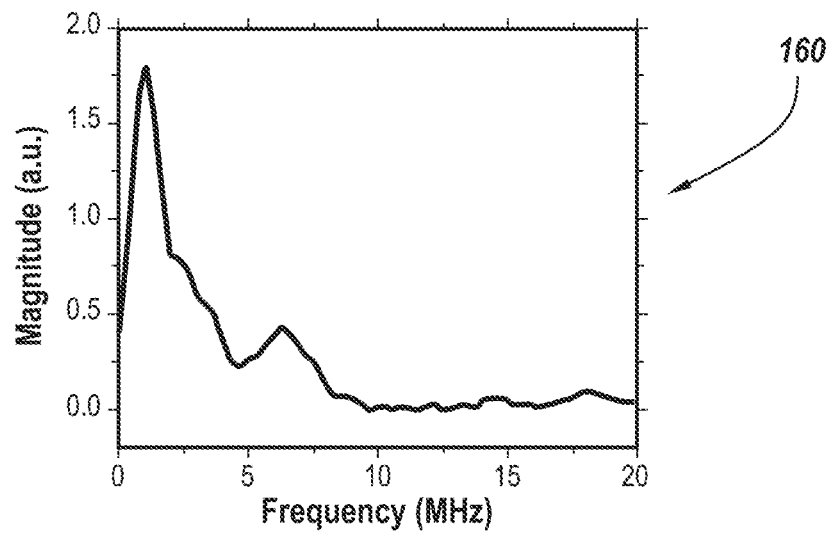
Figure 1G:
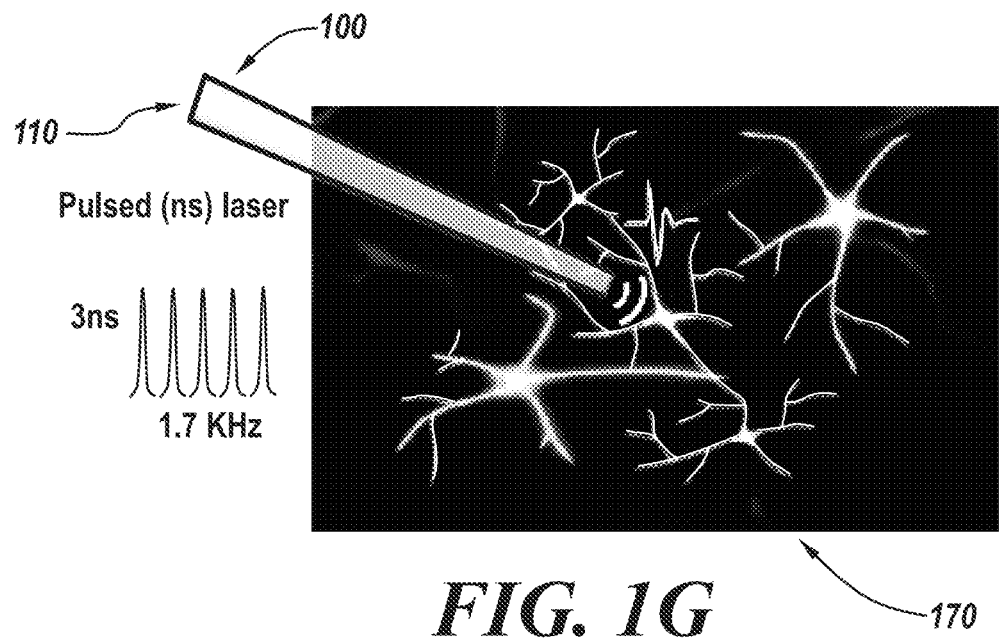
FIG. 1G illustrates a schematic of a TFOE enabling single neuron stimulation in accordance with the teachings herein.

In FIG. 1A, a schematic of the optoacoustic effect, comprising pulsed laser 110 and optoacoustic signal 112, is presented. The design and structure of the FOE 100a, (FOE with a two-layered coating) with fiber 114, diffusion layer 116, and absorption/expansion layer 118, is also presented in this illustrative embodiment. For reference, FIG. 1B provides a dimensional comparison between the fiber-based emitter and a syringe needle (130) using optical fibers for the laser transmission (20 G, ID 0.6 mm, OD 0.91 mm). It should be noted that FOE 100a, 100b, 100c, etc. refer to FOE 100 in FIGS. 1A, 1B, 1C, etc. Further, FIG. 1C presents a side view of the fabricated FOE 100, as the image transparency was adjusted to visualize the inner diffusion layer 116 and the outer absorption/expansion layer 118, with a white dash line outlining the fiber distal end. The diffusion layer 116 was introduced to prevent localized heating and subsequent damage of the expansion layer due to the difference of thermally induced strain within the layer. FIG. 1G presents an additional schematic 170 of FOE 100 enabling single-neuron stimulation via pulsed laser 110.

According to another aspect of the present disclosure, tapered FOE (TFOE) 100 is introduced as an illustrative embodiment. In FIG. 1D, towards single-cell modulation, the TFOE 100 is presented, which only has one layer coating. TFOE 100 may possesses a 20 micron tip diameter as a miniaturized low-frequency ultrasound source. The present disclosure took several innovative steps to overcome the challenges associated with the small 20 micron fiber tip. For control of tapering an optical fiber reproducibly, a multimode fiber 114 was gradually pulled from the full diameter of 225 microns to 20 microns via a thermal tapering technique. To convert the light energy into acoustic waves with maximum efficiency, the present disclosure can optimize the absorption/thermal expansion layer 118, which composes multi-wall carbon nanotubes (CNTs) with strong light absorption embedded in PDMS with a high thermal expansion coefficient. To increase optoacoustic conversion efficiency in the tapered fiber and assure minimum light leakage, the optoacoustic CNT/PDMS coating can be prepared with a large CNT concentration of 15%, by introducing isopropyl alcohol (IPA) to form IPA-coated CNTs with hydroxyl groups. To overcome the reduced viscosity of PDMS induced by high CNT concentration and IPA, as well as to achieve a uniform and controlled coating thickness on the 20 micron cross-section of the tapered end, a punch-through method can be deployed. The coating thickness can be controlled by changing the matrix viscosity via IPA evaporation. The tapered fiber optoacoustic emitter can be further confirmed by microscope imaging to have a CNT/PDMS coating of a thickness of 9.5 micron and an overall diameter of 19.8 microns, meeting the needs of single-cell targeting, again illustrated in FIG. 1D.

According to embodiments of the present disclosure, next, a 1030 nm nanosecond pulsed laser can be delivered to the TFOE 100 to generate optoacoustic signals 112. FIG. 1E shows the average trace of acoustic waveform, given by graph line 150. The near field ultrasound pressure was 56.7 kPa, measured by a needle hydrophone. Radio frequency spectrum of the acoustic waveform after Fast Fourier Transform (FFT) exhibits a broadband acoustic frequency from 0 to 10 MHz with a peak frequency at 1.0 MHz, given by graph line 160 of FIG. 1F, which is within the most frequently used range for transcranial in vivo neuromodulation as well as other biomedical applications. Alternatively, the motions of fluorescent Polymethylmethacrylate (PMMA) beads (Dia. 9 μm) dispersed in Phosphate-buffered saline (PBS) under the application of the TFOE 100 can be used to visualize the distribution of acoustic field. Under a laser burst duration of 50 milliseconds and laser power of 7.8 mW with repetition rate of 1.7 kHz, two beads close to the TFOE 100 tip (less than 1 μm) showed a displacement of 5 μm, while other beads ~20 μm away from the TFOE tip remained stationary upon the TFOE treatment, indicating that the acoustic field generated by the TFOE is localized within a distance of 20 μm.

Figure 1H:
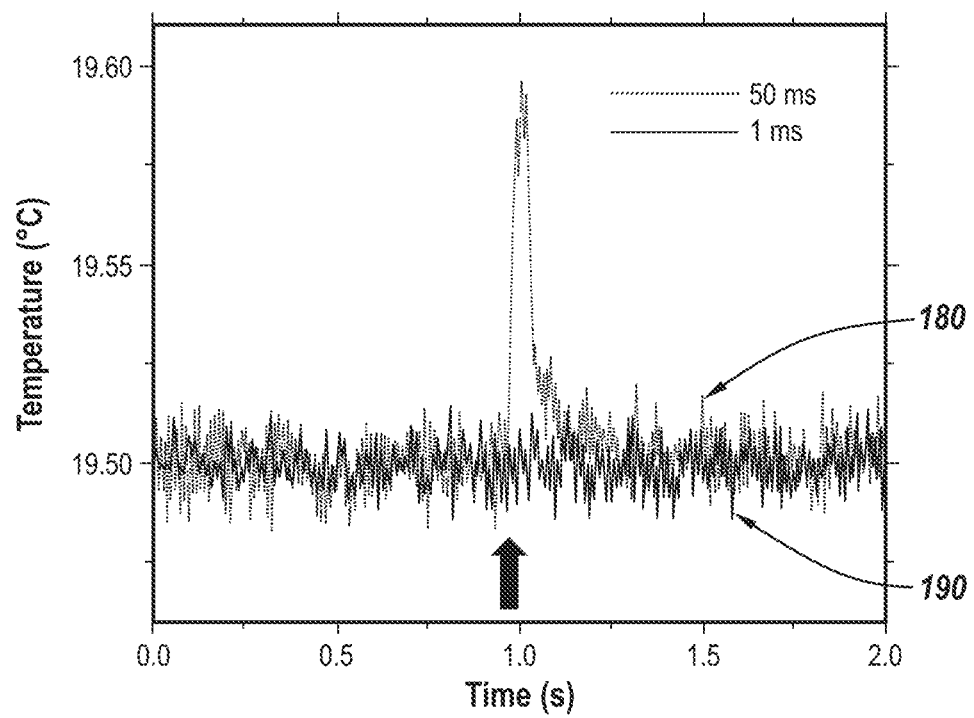
FIG. 1H is a graph of surface temperature of a TFOE tip during laser excitation of 50 milliseconds and 1 millisecond, respectively.

According to embodiments of the present disclosure, to characterize the thermal profile generated by TFOE in water during acoustic generation, temperature on the fiber tip was measured by a miniaturized ultrafast thermal sensor (DI-245, DataQ, OH, USA) directly in contact with the TFOE 100 tip surface. In, FIG. 1H, two exemplary test conditions can be used for successful neuron stimulation: first, a laser pulse train of 50 milliseconds at graph line 180, laser power at 7.8 mW and a repetition rate of 1.7 kHz; second, a laser pulse train of 1 millisecond at graph line 190, a laser power at 11.4 mW and a repetition rate of 1.7 kHz. In this way, the tip surface temperature increases by only 0.093±0.004° C. under the first condition and increase was not detectable under the second condition. This temperature increase is far below the threshold of thermal induced neuron modulation (ΔT≥5° C.). Collectively, these results demonstrate that TFOE 100 with a tip diameter of 20 microns fabricated serves as a point ultrasound source, producing ultrasound fields that are highly localized to around 20 microns from the tip. It is envisioned that this unprecedented spatial confinement will enable high precision stimulation at single neuron level while minimizing thermal damage and undesired mechanical disruptions.

According to another aspect of the present disclosure, this diffusion layer 116 of TFOE 100 comprises a mixture of polymer (Epoxy) and 100-nm diameter zinc oxide (ZnO) nanoparticles, which diffuse the high-energy laser pulse into a Cauchy distribution due to its high optical transparency in the near infrared region and high refractive index. The diameter of ZnO nanoparticles (i.e. 100 nm) is much smaller than the laser wavelength (1030 nm) used, enabling Raleigh scattering in all directions. Then, to convert the light energy into acoustic waves, an absorption/thermal expansion layer 118 can be subsequently added as the second coating. It is composed of nanoparticles with high light absorption coefficient as the absorber (multi-wall carbon nanotubes, MWCNTs) and polymer with high thermal expansion coefficient for the purpose of expansion and compression (PDMS) to maximize the optoacoustic conversion efficiency.

According to the present disclosure, these specially designed nano-polymer composite layers 116 and 118 at the fiber distal end of the TFOE 100, upon the pulsed laser excitation, effectively generate an acoustic wave from the fiber tip of the TFOE 100 through the optoacoustic effect and detected via transducer. Moreover, to achieve a tunable acoustic pressure, according to the optoacoustic theory, the pressure is proportional to the incident laser fluence. Thus, the amplitude and frequency spectrum of TFOE with varied laser fluence is also characterized, indicating the flexibility of the pressure for different applications.

It should be noted that to realize the controllability of the ultrasound frequency of TFOE 100, the two-layer coating comprising 116 and 118 can be designed to mimic the structure of a typical transducer. A transducer (not pictured) is composed of three layers: a backing layer to match the specific acoustic impedance between the active layer and the back connector; an active layer (piezo-electric materials to generate ultrasound upon applied voltage) and a matching layer to match the specific acoustic impedance between medium and the active layer (since the specific acoustic impedance of PDMS (1.1-1.5 Pa s/m3) is close to water (1.48 Pa·s/m3), the third layer-matching layer can be spared in the TFOE 100). In a transducer, the frequency is determined by two factors. First, the frequency and bandwidth are controlled by the damping effect of the backing layer. Second, the frequency is reversely proportional to the thickness of the active layer. In this way, by modifying acoustic damping of the first layer 116 and light absorption thickness of the second layer 118 in the TFOE 100, frequency can be controlled precisely.

According to embodiments of the present disclosure, ultrasound frequency can be controlled via modification of the diffusion layer 116. For example, controlling frequency can involve modification of the diffusion layer 116 of a FOE 100 corresponding to the backing layer of a transducer. The epoxy (specific acoustic impedance: 2.5-3.5 Pa·s/m$^3$) in the diffusion layer 116 acts as the backing layer matrix to match the specific acoustic impedance between the fiber 114 (silica, specific acoustic impedance:13.1 Pa·s/m$^3$) and the active layer 118 (PDMS, specific acoustic impedance: 1.1-1.5 Pa·s/m$^3$). The damping effect of the backing layer in a typical transducer impacts on the frequency produced, permitting the expectation that the change of the thickness of the diffusion layer 116, acting as the backing layer, will control the output frequency of TFOE 100. Continuing with the illustrative example, fabricated FOEs 100 with ZnO/Epoxy diffusion layer 116 thickness can consist of 36, 42, 53, 62, 79, 100 μm, respectively, with absorption/thermal expansion layers 118 of CNTs/PDMS with a thickness of 109±24 μm. It should be noted that the variation of the thermal expansion layer 118 thickness does not change the ultrasound frequency since they are all beyond the light penetration depth.

Figure 2A:
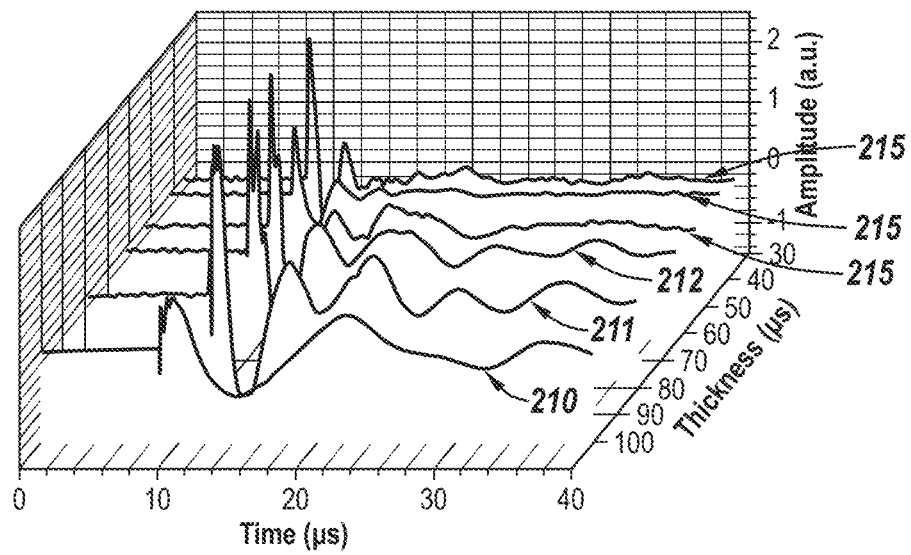
FIGS. 2A-D illustrate controlling the ultrasound frequency via modifying the diffusion layer 116.
Figure 2B:
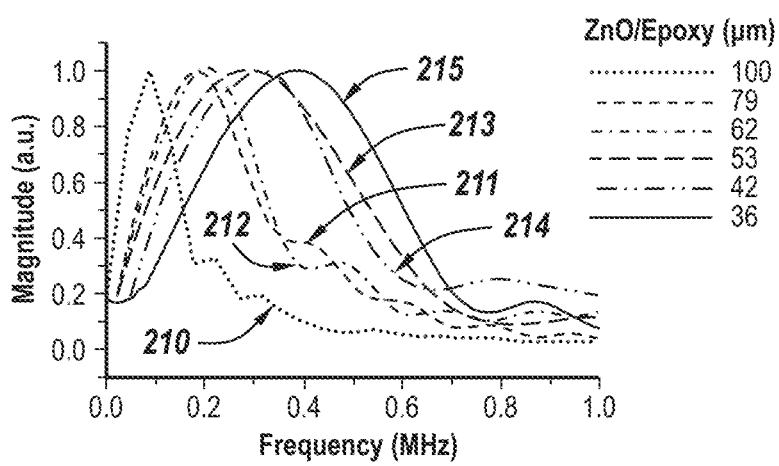

FIGS. 2A-2D provide graphs relating to controlling the ultrasound frequency via modifying the diffusion layer 116. In FIG. 2A, the ultrasound signals in time domain from FOEs 100 fabricated with diffusion layer 116 (ZnO/Epoxy) of 36-100 μm and absorption/thermal expansion layer 118 (CNTs/PDMS) of 109±24 μm are presented at graph lines 210 (100 μm), 211 (79 μm), 212 (62 μm), 213 (53 μm), 214 (42 μm), and 215 (36 μm) as a function of time, thickness, and amplitude, respectively. FIG. 2B illustrates the frequency domain within 0-1.0 MHz of the ultrasound. The peak frequency was shown at graph 220 to be controlled in the range of 0.384 to 0.083 MHz through varying the diffusion layer 116 thickness from 36 to 100 μm, suggesting a significant decrease in frequency while increasing the diffusion layer 116 thickness.

Figure 2C:
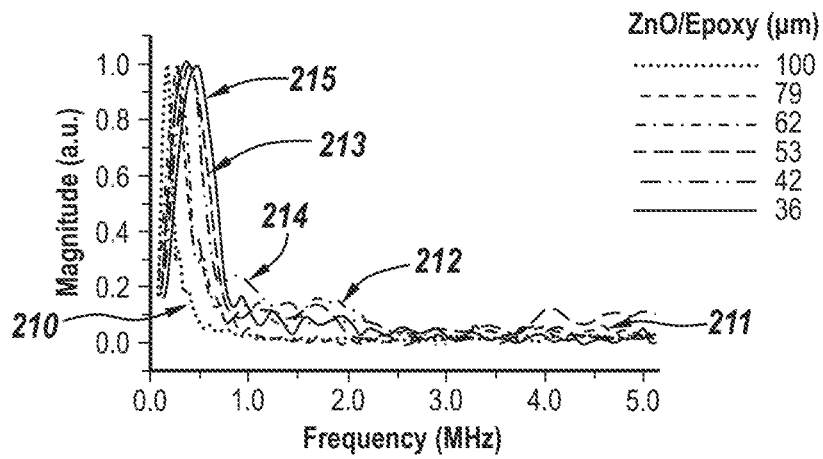
Figure 2D:
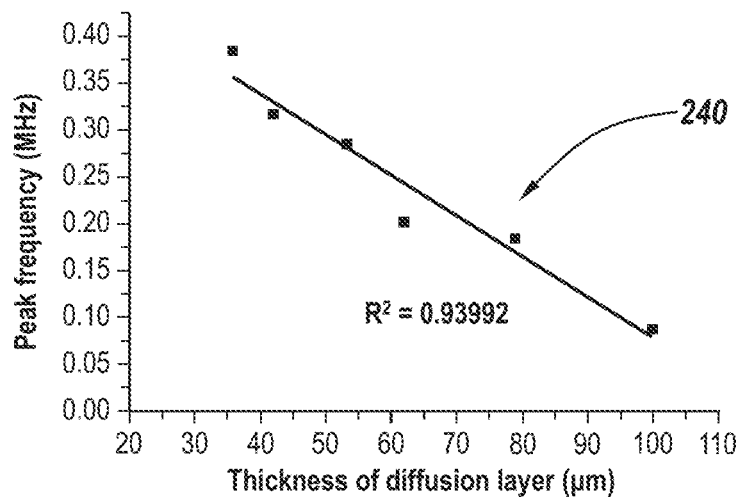

Continuing to FIG. 2C, a graph of peak ultrasound frequency at graph 230 by thickness of diffusion layer 116 is shown, the peak ultrasound frequency being tunable via a change in thickness of the diffusion layer. By examining the frequency range of 0-10 MHz at lines 210 (100 μm), 211 (79 μm), 212 (62 μm), 213 (53 μm), 214 (42 μm), and 215 (36

µm), the distribution of frequencies exhibited a clustering at sub-MHz region. In addition, the linear relationship of the frequency and diffusion layer 116 thickness shows an R2 of 0.93992 with a function of y=0.51086-0.00431x in graph 240 of FIG. 2D. Controlling the frequency through changing the diffusion layer 116 can be further rationalized by the fact that the peak frequency of the optoacoustic spectrum could be modulated by the mass of the diffusion layer 116. The optoacoustic effect can be described by the thermal expansion equation, which is a derivative of the generalized Hooke's law and the equation of motion that is deduced from Newton's second law. During the optoacoustic conversion process, the TFOE 100 tip can be regarded as a harmonic oscillator, in which the oscillating motion comes from the initial force given by the thermal expansion effect. In Hooke's law, the amplitude of the oscillation remains constant, and its frequency is independent of its amplitude, but determined by the mass and the stiffness of the oscillator. To this end, the frequency range of 0.083-0.384 MHz is achieved via modifying the Epoxy/ZnO diffusion layer 116.

Moreover, for typical transducers, the bandwidth is defined by the ratio between the difference of the frequencies at which the spectrum intensity decays to 50% of its maximum value ($f_{upper}-f_{lower}$) and the central frequency $f_{central}$:

$$\text{Bandwidth} = \frac{f_u - f_l}{f_c} * 100\% \quad (1)$$

The bandwidths for the FOE 100 with central frequencies of 0.083-0.384 MHz were obtained from eq. 1, with an average bandwidth of 67.8±6.8%. These results show that the ultrasound bandwidths generated by FOE 100 are comparable to bandwidths produced by commercial transducers for corresponding frequencies, e.g. 67.09% for 5 MHz, V326, Olympus; 56.00% for 10 MHz, XMS310, Olympus. Notably, in commercial transducer, it was found that varying the central frequency via changing the backing layer thickness does not change the bandwidth significantly, which is coincident with the FOE 100 bandwidth showing an insignificant frequency dependence.

According to embodiments of the present disclosure, ultrasound frequency can also be tuned or controlled via altering the CNT concentration in the expansion layer. An illustrative embodiment of the present disclosure to manipulate frequency involves changing the effective thickness of the active layer (i.e. the absorption/thermal expansion layer 118). According to the optoacoustic generation theory, the waveform of optoacoustic is also depending on the light absorption profile of the optoacoustic source, which is T+1/ca (r is the laser pulse width, a is the light absorption coefficient of the absorber). The effective thickness of the absorber is determined by the light penetration depth. In this way, the optoacoustic signal waveform consequentially changes with the effective absorber thickness, and, as absorber thickness is smaller than the light penetration depth, the frequency is determined by the absorber thickness. When the absorber thickness is larger than the light penetration depth, the frequency will remain constant and the extra thickness only induces acoustic attenuation.

Figure 3A:
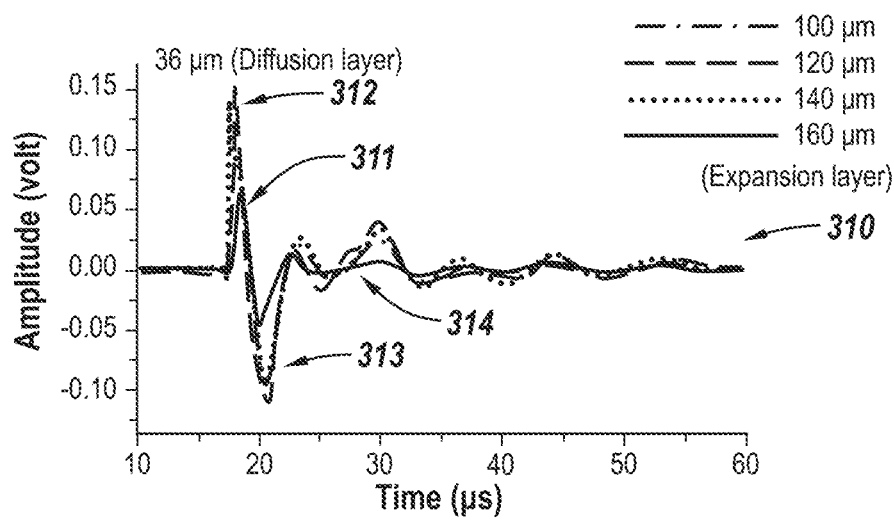
FIGS. 3A and 3B are graphs of the effect of physical thickness of expansion layer on frequency with TFOE diffusion layer coatings of 36 and 100 μm respectively.
Figure 3B:
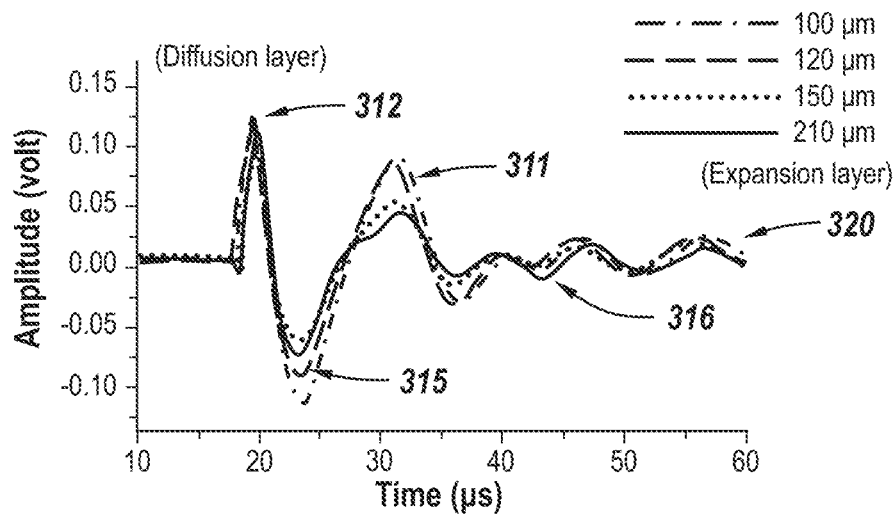

FIGS. 3A-3B illustrate a characterization of the effect of physical thickness of the expansion layer on frequency. According to this aspect of the present disclosure, two groups of TFOEs 100 were fabricated with ZnO/Epoxy diffusion layer 116 with 36 µm and 100 µm, respectively. FIG. 3A is a graph 310 of expansion layers of 100 microns (graph line 311), 120 microns (graph line 312), 140 microns (graph line 313), and 160 microns (graph line 314). FIG. 3B is a graph 320 of expansion layers of 100 microns (graph line 311), 120 microns (graph line 312), 150 microns (graph line 315), and 210 microns (graph line 316). For each group, 4 TFOEs were made with CNT/PDMS expansion layers varied from 100 µm to 210 µm as indicated by the legend in FIG. 3, which illustrates the time domain of ultrasound from TFOEs. The waveform remained as similar functions with respect to time while the amplitude was dropping with the increasing of the expansion layer thickness. As a result, when the absorber layer 118 thickness is beyond the light penetration depth, the frequency is not sensitive to the change of the additional physical thickness of expansion layer in the tested range, while the amplitude changing could result from the acoustic attenuation by the extra thickness of the thermal expansion layer.

It should be noted that while the additional physical thickness (beyond light penetration depth) is not a controlling factor for the frequency, it is contemplated that the frequency can be varied by changing the effective absorber thickness. This can be achieved through modifying the spatial absorption profile of the expansion layer via changing the absorber concentration. Since the effective thickness is primarily determined by the light absorption profile but not the physical thickness, in this way, the influence of fluctuation in the physical thickness and geometric structures would be minimized, improving the robustness of the TFOE 100 fabrication.

Figure 4A:
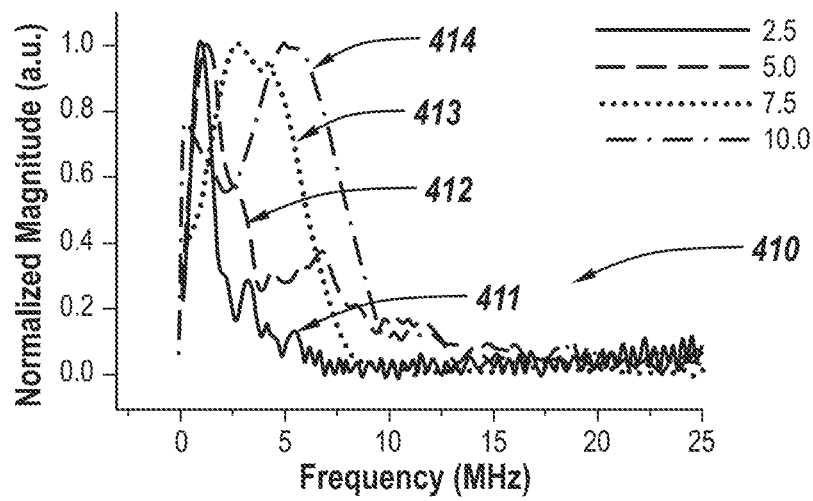
FIGS. 4A-4B illustrate optoacoustic signal frequency as a function of effective absorption/expansion layer thickness.
Figure 4B:
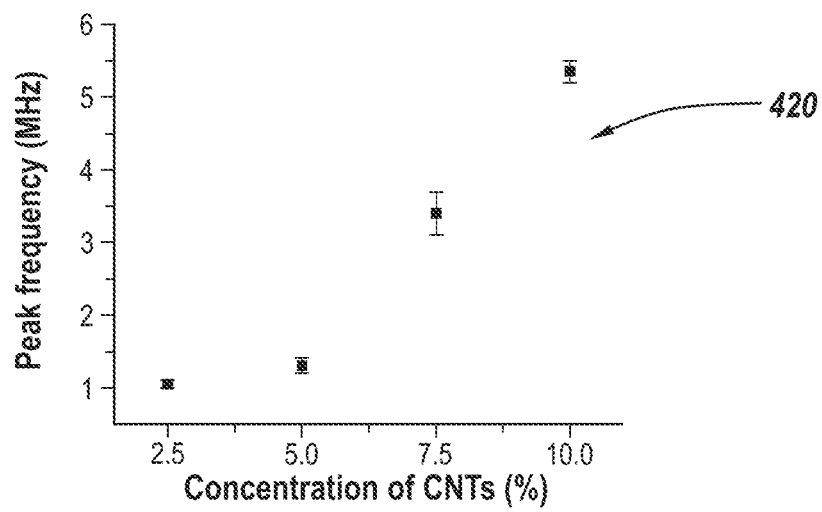

To verify how the absorber concentration can be modified to fine-tune the ultrasound frequency, FOEs 100 were coated only with the CNTs/PDMS expansion layers without the diffusion layers 116. Different concentrations of CNTs (2.5%, 5.0%, 7.5%, 10.0% by weight) were used in the mixture. The thickness of the overall coating was kept in the same range. FIG. 4A provides an illustration of optoacoustic signal frequency as a function of effective absorption/expansion layer 118 thickness. Graph lines 411, 412, 413, and 414 at graph 410 illustrate absorption/expansion layer 118 thickness at 2.5, 5.0, 7.5, and 10.0% concentrations, respectively. FIG. 4B illustrates peak frequency plotted as a function of CNTs/PDMS concentration, with each data point in 4B as the average value of two identical FOEs for each concentration and error bars are the standard deviation. Thereby, the present disclosure provides that CNT concentration dependent frequency change permits that the controllable peak frequency of optoacoustic can also be achieved by modifying the light absorption profile of the absorption/expansion layer 118 via graph 420.

Figure 5A:
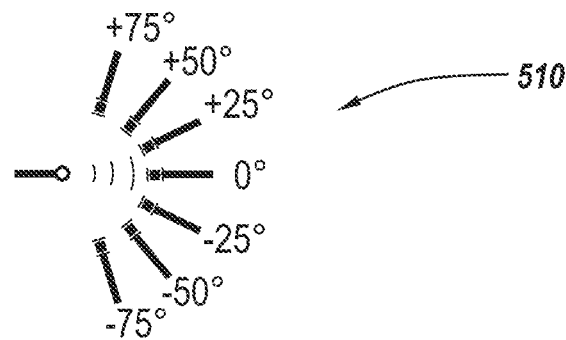
FIGS. 5A-5D illustrate the characterization of acoustic angular distribution.
Figure 5B:
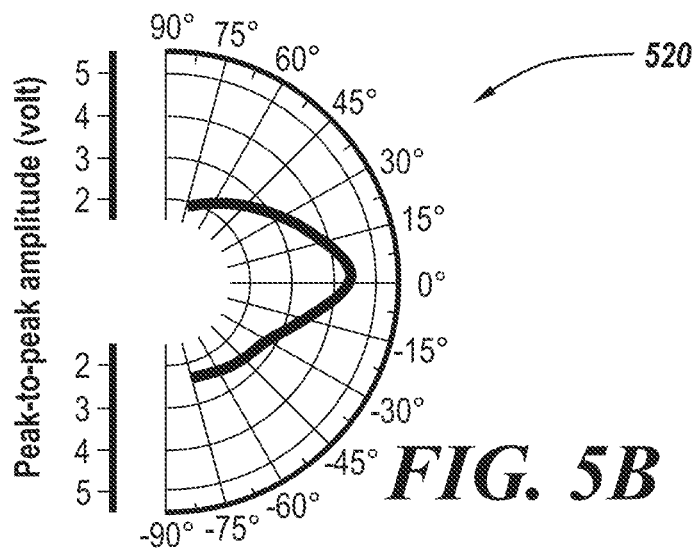
Figure 5C:
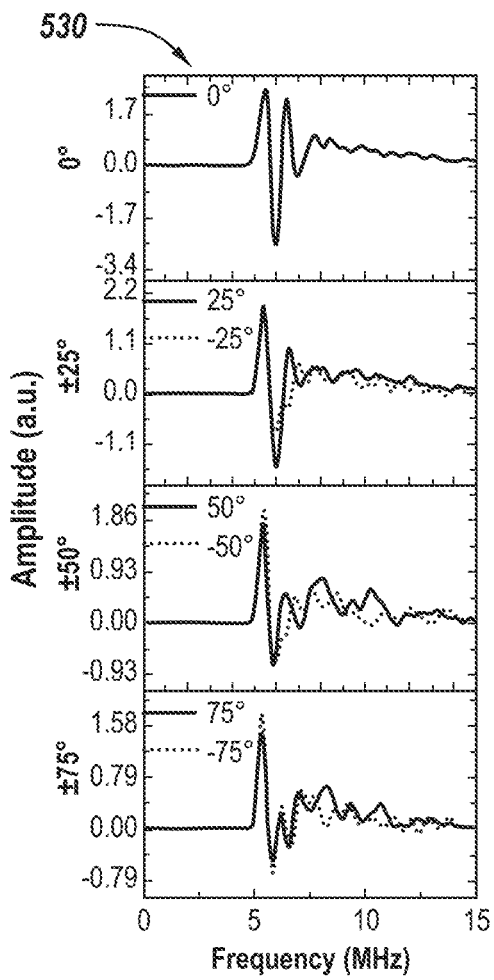
Figure 5D:
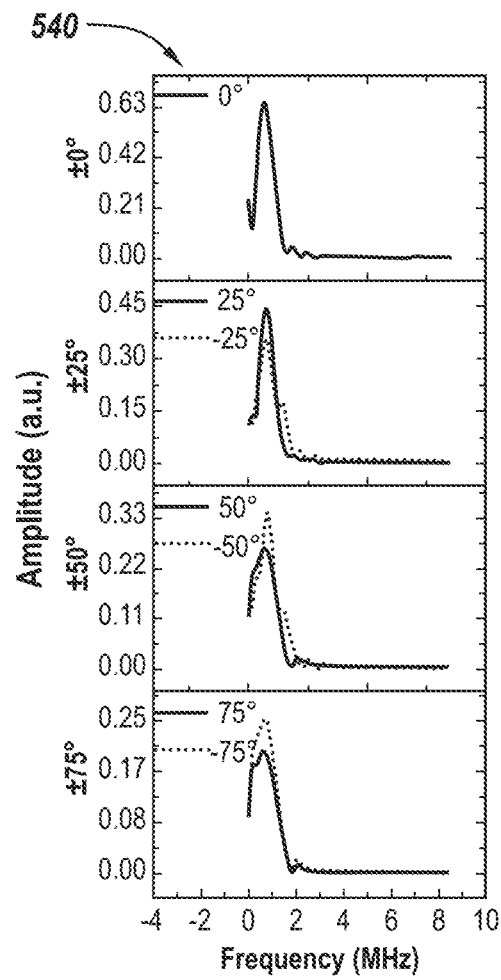

According to the exemplary embodiments described herein by the present disclosure, the angular distribution of the acoustic wave in terms of amplitude and frequency spectra can be further characterized. To do so, a FOE 100 can be composed of a diffusion layer 116 (ZnO/Epoxy, 40 µm thick) and an expansion layer 118 (CNTs/PDMS, 120 µm thick). The acoustic radiation from the FOE 100 can be determined by measuring the output voltage on the oscilloscope at a constant light input of 127 mJ/cm2. The angle of the transducer detector relative to the fiber axis can be varied by a controllable 360° rotation stage (for example, Thorlabs, Inc., NJ, USA) with an accuracy of ±1°. Optoacoustic signals can be acquired at angles of 0°, ±25°, ±50° and ±75°, respectively, as illustrated in graph 510 of FIG. 5A. In this way, FIGS. 5B and 5C show the measured acoustic amplitudes at 520 and 530 respectively. The peak-to-peak photoacoustic amplitude in FIG. 5C can be found to decrease from 5.2 (at 0°) to 1.6 (at ±75°), respectively, which indicates that the larger the angle, the weaker the acoustic amplitude it has, with the maximum amplitude in the front direction. The PA amplitude anisotropy is expected to result from the light intensity anisotropy. Specifically, the angular distribution of light intensity with one layer of ZnO/Epoxy (15% by weight) was previously measured, angular light intensity distribution was measured using a photodiode mounted on a controllable 360° rotation stage. The light intensity at 50° was approximately 41% of the light intensity at 0°. In FIG. 5C, the acoustic amplitude at 50° was 37% of the amplitude at 0° (1.9 V vs. 5.2 V). Thereby, the acoustic amplitude distribution is consistent with the light intensity distribution data. FIG. 5D shows at 540 that the peak frequency can be relatively constant (0.7-0.8 MHz) when varying the angle from 0° to ±75°. This is because that majority of the laser pulse energy was delivered along the laser forward direction, despite the effect of diffusion layer 116, little light propagates laterally, making the lateral optoacoustic induced vibration negligible. Other factors, including the dispersion by the diffusion layer 116, the curvature radius of the spherical coating, the discrepancy of density and sound speed between PDMS and water, could also contribute to the amplitude anisotropy.

Figure 6A:
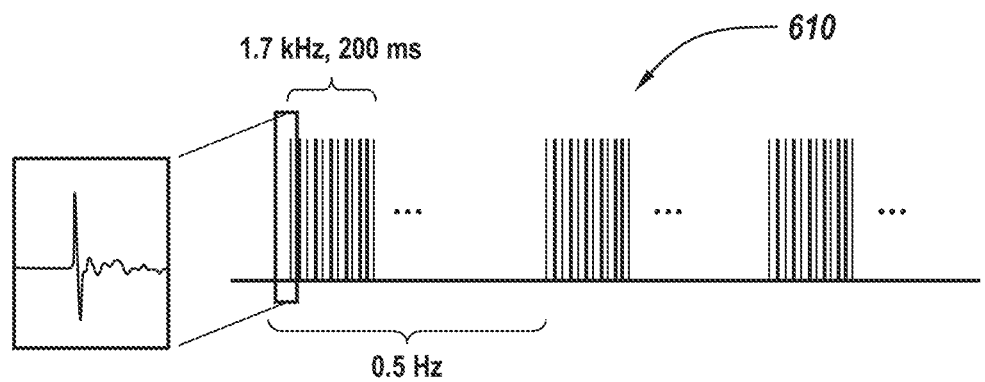
FIGS. 6A-6G illustrate frequency dependence of cellular sonoporation induced by TFOEs.

According to another aspect of the present disclosure, the FOE 100 mediated molecule delivery is frequency dependent and shows a spatial confinement of 0.2 mm². According to an illustrative embodiment, cellular uptake of cell membrane impermeable fluorescence molecules during sonoporation mediated by FOEs 100 with varied frequency can demonstrate the superior performance of sub-MHz ultrasound as well as elucidate the spatial confinement of the FOE. A high-affinity intercalating nucleic acid stain-SYTOX Green, which only penetrates into cells through a compromised plasma membrane and displays fluorescence enhancement upon binding to nucleic acids, can be chosen to visualize the sonoporation process. Ultrasound bursts of 200 ms duration can thereby be generated using a pulsed laser with 39 mJ/cm2 at a 1.7 kHz pulse repetition rate, which corresponds to approximately 340 acoustic pulses per burst, as seen in the schematic 610 of FIG. 6A. The optoacoustic treatment can be performed at a burst repetition rate of 0.5 Hz in a total period of 10 min. FOEs can be placed approximately 100 μm above the cells in culture medium.

Figure 6B:
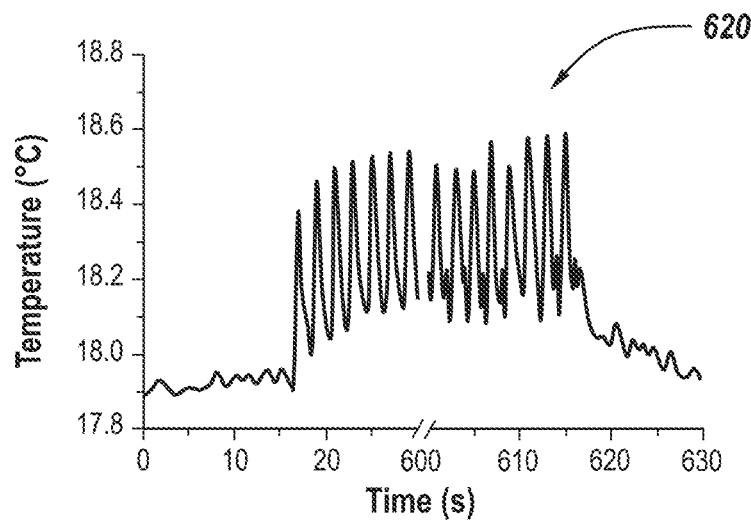

First, to exclude the thermal induced cell membrane permeabilization, the temperature increase at the fiber tip during the FOE treatment can be measured using a miniaturized ultrafast thermal probe (100 μm in diameter) placed in contact with the fiber tip. It is envisioned that the temperature rise can be found to be 0.6° C. within a total duration of 10 min, as illustrated in graph line 620 of FIG. 6B. At such small temperature increase, thermal-induced membrane depolarization is negligible. Therefore, the Sytox uptake results are attributed to mechanical disruption induced by the optoacoustic wave from the TFOE.

Figure 6C:
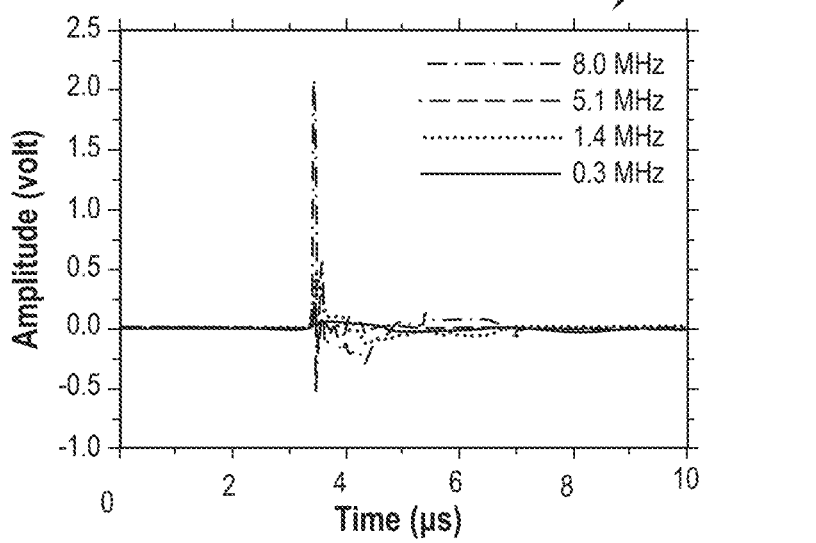
Figure 6D:
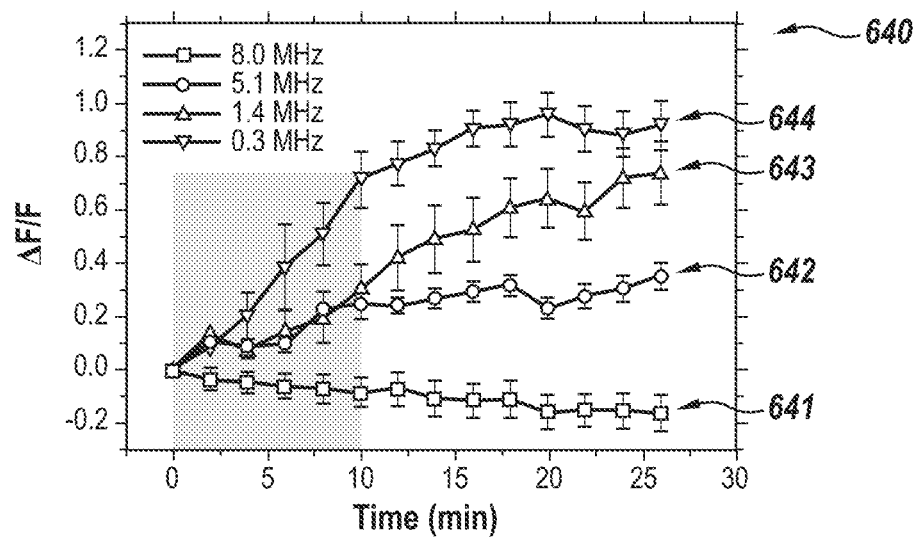
Figure 6E:
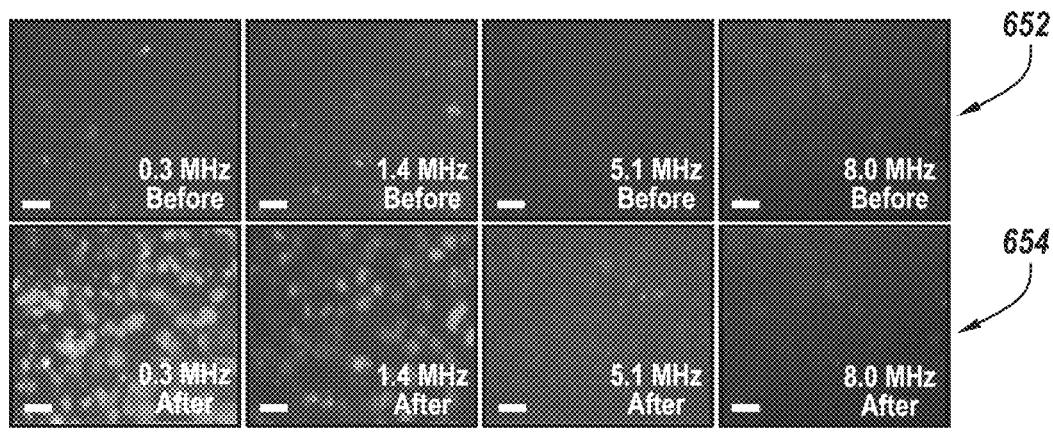

To study the ultrasound frequency dependence of Sytox uptake efficiency, TFOEs with peak frequency of 8.0, 5.1, 1.4 and 0.3 MHz can be utilized (8.0 MHz: 15% CNT/PDMS; 5.1 MHz: 10% CNT/PDMS; 1.4 MHz: 5% CNT/PDMS; 0.3 MHz: 15% ZnO/Epoxy+10% CNT/PDMS). The ultrasound with varied frequencies is shown in time domain 630 of FIG. 6C. The laser fluence should be kept constant to assure identical energy input. The 8.0 MHz signal should thereby exhibit the highest amplitude (2.650 V) while the 0.3 MHz signal had the lowest amplitude (0.087 V), which could be partially attributed to the non-uniformity of transducer sensitivity. FIG. 6E shows the fluorescence images of the cell culture before at 652 (0 min, upper panels) and after at 654 (26 min, lower panels) the TFOE treatment. When cells are treated with the TFOE, cellular uptake of Sytox is significantly increased, indicated by the elevated fluorescence signals. Specifically, 0.3 MHz ultrasound, although with the lowest acoustic intensity, exhibited the highest fluorescence increase after the TFOE treatment indicating the highest sonoporation efficiency compared to 1.4 MHz and 5.1 MHz. In comparison, the group treated with 8.0 MHz ultrasound showed negligible Sytox uptake. Overall, the sonoporation efficiency exhibited frequency dependence: the lower the frequency, the higher the cellular uptake efficiency. This conclusion can be further demonstrated statistically. In FIG. 6D, the average fluorescence intensity from 30 individual cells treated by varied frequencies are plotted as a function of time in graph 640. TFOE produced graph lines 5.1 (642), 1.4 (643) and 0.3 (644) MHz ultrasound all show increased Sytox fluorescence as a function of time after the treatment, confirming the capability of facilitating Sytox uptake. FIG. 6D also shows a plateau of fluorescence at around 25 min after the treatments indicated that the membrane pores were resealing. The dynamic is consistent with the previous study reported, in which focused ultrasound facilitated the Sytox uptake on the time scale of tens of minutes. Specifically, the curve of the 0.3 MHz group shows the highest slope, meaning that the graph line 644 of 0.3 MHz facilitated the Sytox uptake much faster than others. The final reading also demonstrates that the graph line 644 of 0.3 MHz shows the highest $\Delta F/F$ of 0.92 after the TFOE treatment indicating the highest sonoporation efficiency compared to graph line 643 of 1.4 MHz ($\Delta F/F=0.74$) and graph line 642 of 5.1 MHz ($\Delta F/F=0.35$). Thereby, the total amount of uptaken Sytox is frequency dependence: the lower the frequency, the more the molecules pass through the compromised cell membrane within a given period. Furthermore, the graph line 641 of 8.0 MHz group does not exhibit significant fluorescence increase but a slight fluorescence decrease. Taking account of the potential influence from photo bleach of Sytox, the reason for overall decline of fluorescence could be that the Sytox uptake induced fluorescence increase was too weak compared to the photo bleach effect. It is conceivable that further increasing the incident laser power to 8.0 MHz ultrasound treatment could eventually result in sonoporation and delivery comparable to the 0.3 MHz group, at the cost of thermal and/or photodamage to the cells. Collectively, the TFOE induced sonoporation shows a frequency dependence in which the low frequency performs higher efficiency than high frequency.

To quantify the sonoporation efficiency, the cells can be counted with $\Delta F/F \geq 50\%$ as Sytox positive cells and calculated the percentage of Sytox positive cells in the illuminated area. This percentage is taken as a measure of the FOE sonoporation efficiency. For TFOEs with frequency of 5.1, 1.4 and 0.3 MHz under the same laser energy and duration, the efficiency obtained from fluorescence imaging at 26 min is found to be 0%, 72.7% and 83.3%, suggesting the lower frequency has substantial higher sonoporation efficiency than the higher frequency ultrasound. The higher efficiency of low frequency ultrasound can be explained by the intramembrane cavitation theory that ultrasound induces bilayer membrane motion, which does not require preexistence of air voids in the tissue. Since the maximum area strain is inversely proportional to the square root of the frequency, the low frequency ultrasound has a lower cavitation threshold, resulting in the improved sonoporation efficacy. In the work of ultrasound induced Sytox uptake with the assistance of microbubbles, the maximum percentages of MDA-MB-468 cells with uptake were less than 20% following sonication for 15 ms (150 cycles with pulse duration of 100 μs) with 400, 500 and 600 kPa, respectively (threshold of ΔF/F unknown). In the present disclosure, TFOE provides pressure around 40 kPa with effective sonication duration of 1.1 ms (340 pulses, pulse duration less than 3.3 s), and enables sonoporation efficiency of 72.7% and 83.3% for low frequency. Thus, the low frequency localized optoacoustic wave generated by TFOE shows comparable performance although the test cells are different.

Figure 6F:
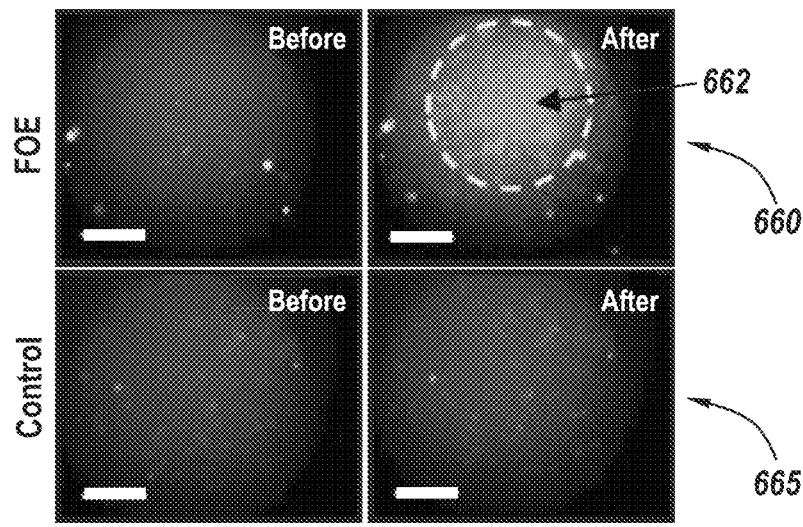
Figure 6G:
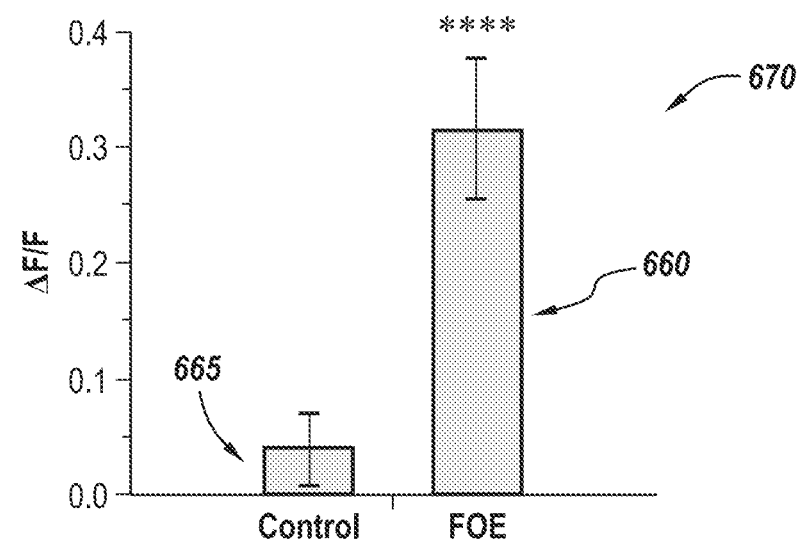

To validate that the TFOE provides a unique strategy to enable localized regional cell modulation through the localized delivery of specific molecules to cells by the confinement of the sonoporation, compared to typical the whole cell dish modulation, fluorescence increase of cell cultures were examined with a 10× field. The localized delivery can be seen in FIGS. 6F and 6G. FIG. 6F provides fluorescence images of the TFOE treated group 660 and control group 665 taken with 10× objective. The white dash circle indicates the region of significant fluorescence intensity change observed, which is right beneath the position of the TFOE at a distance of 100 μm above the cells. After the TFOE treatment, the treated region 662 with an area of 0.2 mm2 exhibits significant fluorescence increase of 32%, indicating a spatial confinement of 0.2 mm2 laterally. To further validate the localization, since the conventional transducer array is diffraction limited in the sub-MHz range, the FOE induced cell modulation in tissue using two-photon imaging would reveal the spatial confinement via 3-dimensional visualization. Next, to test the bio-safety of TFOE, using 2 μg/mL Propidium Iodide staining (from, for example, Thermo Fisher Scientific, Waltham, Mass., USA), the cell viability after FOE treatment can be found as 99.55±0.03%, indicating the superior biocompatibility of TFOE treatment. FIG. 6G is a graph 670 of a comparison of fluorescence intensity change between TFOE treated group 660 and control group 665, **** P<0.0001. Collectively, the TFOE used as a novel ultrasound source for small molecule delivery into cells exhibited frequency dependence, indicating the significance of sub-MHz ultrasound. The localized fluorescence change is indicative of the 0.2 mm$^2$ spatial confinement of the TFOE, holding promise for cell modulation with high spatial precision, including neuron stimulation as well as localized gene transfection for gene-protein studies.

According to exemplary embodiments provided herein, fiber based photoacoustic emitters 100 composed of nanoparticle polymer matrix with superior optical and mechanical properties are designed and fabricated. The two-layer coating design, including a diffusion layer 116 and an expansion layer 118, provides precise controllability in amplitude and frequency of the ultrasound generated. Localized acoustic wave generation with high amplitude and tunable frequency in the sub-MHz range is achieved. In some embodiments, by characterizing the optoacoustic signal profile in amplitude and frequency spectrum, a matrix of CNTs/PDMS is demonstrated to be a preferable candidate to achieve high amplitudes. Two effective strategies to control the acoustic frequency, can be demonstrated. First, the frequency can be varied by the thickness of the diffusion layer 116, which act as damping material via the acoustic impedance mismatch. Second, the acoustic frequency is also controlled by the depth of light penetration through the active absorber/expansion layer 118, which can be indirectly controlled by changing the absorber concentration. By using the TFOEs with varied frequency ranging from 0.3 MHz to 8.0 MHz for small molecules delivery into cell membrane, sub-MHz ultrasound exhibits superior efficiency compared to high frequency. A lateral spatial confinement of 0.2 mm2 can also be confirmed by the sonoporation effective area. Thus, a sub-MHz frequency acoustic with sub-millimeter confinement was produced using the miniaturized TFOE 100, overcoming the limitation of other typical ultrasound sources. It is envisioned that such TFOE 100 device design holds promise for a wide range of cellular applications, including but not limited to, cell membrane sonoporation, and offers new tools for localized drug delivery, neuron stimulation and gene transfection with high efficacy and minimized safety issue.

By achieving the high miniaturization levels demonstrated, the tunable optoacoustic emitters are promising for minimally invasive medical applications, where the fiber based optoacoustic devices presented herein via the present disclosure could be inserted, for example, in syringe needles or catheters in close proximity to a focal lesion, thus overcoming the problem of reduced precision and amplitude induced by traditional focused ultrasound. It is envisioned that further embodiments can improve the performance. For example, the laser beam can be coupled to the fiber using higher order modes for optimum optoacoustic signal generation. Second, the shape of TFOE tip can provide opportunity to focus the wave via concave structure. Third, further validating the localization of the sub-millimeter is challenging, since the conventional transducer array is diffraction limited in the sub-MHz range. The TFOE induced cell modulation in tissue using two-photon imaging would reveal the spatial confinement via 3-dimensional visualization. Under a broader context, this technique offers the potential to generate stable and reversible sonoporation at each focal target through modification of the ultrasound parameters, enabling precise control for biomedical ultrasound application, which is not available with existing technologies, especially for drug delivery and gene transfer. Additionally, this TFOE 100 is immune to electromagnetic interference and hence is compatible with magnetic resonance imaging (MRI). These flexibilities, along with its unprecedentedly miniaturization, and amenability to be readily repeated, make the methods and devices of the present disclosure a transformative technology.

According to another aspect of the present disclosure, the two-layer fabrication of TFOE 100 is composed of two steps. First, for the diffusion layer 116, the Epoxy or PDMS matrix can be prepared via cross linking process. Epoxy was made by mixing polyepoxides solution (for example, Devcon Inc, Alberta, Canada) with polyfunctional curatives in a ratio of 1:1 by volume. For PDMS, the silicone elastomer (for example, Sylgard 184, Dow Corning Corporation, USA) can be dispensed directly into the container carefully to minimize air entrapment, followed by mixing with the curing agent in a ratio of 10:1 by weight. Subsequently, ZnO nanoparticles serving as diffuser (for example, ~100 nm, Sigma-Aldrich, Inc., MO, USA) can be added into the matrix at a concentration of 15% by weight otherwise specified. A multimode optical fiber with 200 μm core diameter (for example, FT200EMT, Thorlabs, Inc., NJ, USA) and a polished distal end was carefully dipped about 100 μm below the surface of the mixture solution and then quickly pulled up, using a micro manipulator. According to the present disclosure, by placing vertically at room temperature, the polymer crosslinked and the matrix formed the coating. It is envisioned that the diffusion layer 116 made of Epoxy can be subsequently coated with the absorption/thermal expansion 118 layer of Epoxy.

In this way, the specific acoustic impedance mismatch can be minimized, providing the maximized optoacoustic conversion efficiency. Graphite powder (for example, Dick Blick Holdings, Inc., IL, USA) can be mixed with the matrix at a concentration of 30% by weight. MWCNTs, (for example, <8 nm OD, 2-5 nm ID, Length 0.5-2 μm, VWR, Inc., NY, USA) can be used at a concentration of 0-10% by weight, approaching the solubility upper limit owing to its low density (1.65 g/cm2). Similarly, the TFOEs made of PDMS matrix can be fabricated. In an illustrative embodiment of TFOE generating sub-MHz frequencies, the structure can be modified as ZnO/Epoxy (the diffusion layer 116) and CNTs/PDMS (the absorption/thermal expansion layer 118), in which Epoxy and PDMS realized specific acoustic impedance mismatch. In this way, the pressure can be compromised while still meeting the frequency need for cell modulation. By making a mark near the fiber tip with thermal resist ink, the thickness after coating can be measured by aligning the mark on the before-and-after micrograph. Notably, light leak can generate acoustic response on the detecting transducer due to the pulsed laser induced shockwave in water and transducer probe, and potentially cause damage of the detector. A power meter can be used to measure light transmittance to evaluate the light leak. Thereby, the design and fabrication of the present disclosure discussed above can eliminate the light leak of TFOEs 100.

According to embodiments of the present disclosure, the design and fabrication of fiber based photoacoustic emitters composed of nanoparticle polymer matrix with superior optical and mechanical properties is disclosed. It is contemplated that the two-layer coating design, including a diffusion layer 116 and an expansion layer 118, provides precise controllability in amplitude and frequency of the ultrasound generated. Localized acoustic wave generation with high amplitude and tunable frequency in the sub-MHz range were achieved. By characterizing the optoacoustic signal profile in amplitude and frequency spectrum, a matrix of CNTs/PDMS can be demonstrated as a preferable candidate to achieve high amplitudes.

According to the present disclosure, two effective strategies to tune (i.e. control) the acoustic frequency are provided. First, the frequency can be varied by the thickness of the diffusion layer 116, which acted as damping material via the acoustic impedance mismatch. Second, the acoustic frequency can also controlled by the depth of light penetration through the active absorber/expansion layer 118, which has been indirectly controlled by changing the absorber concentration. By using the TFOEs 100 with varied frequency ranging from 0.3 MHz to 8.0 MHz for small molecules delivery into cell membrane, sub-MHz ultrasound exhibited superior efficiency compared to high frequency. A lateral spatial confinement of 0.2 $mm^2$ can also be confirmed by the sonoporation effective area. Thereby, a sub-MHz frequency acoustic with sub-millimeter confinement can be produced using the miniaturized TFOE, overcoming the limitation of other typical ultrasound sources. This TFOE device design holds promise for a wide range of cellular applications and other illustrative applications, including cell membrane sonoporation, while also offering new tools for localized drug delivery, neuron stimulation and gene transfection with high efficacy and minimized safety issue.

Figures 34A, 34B:
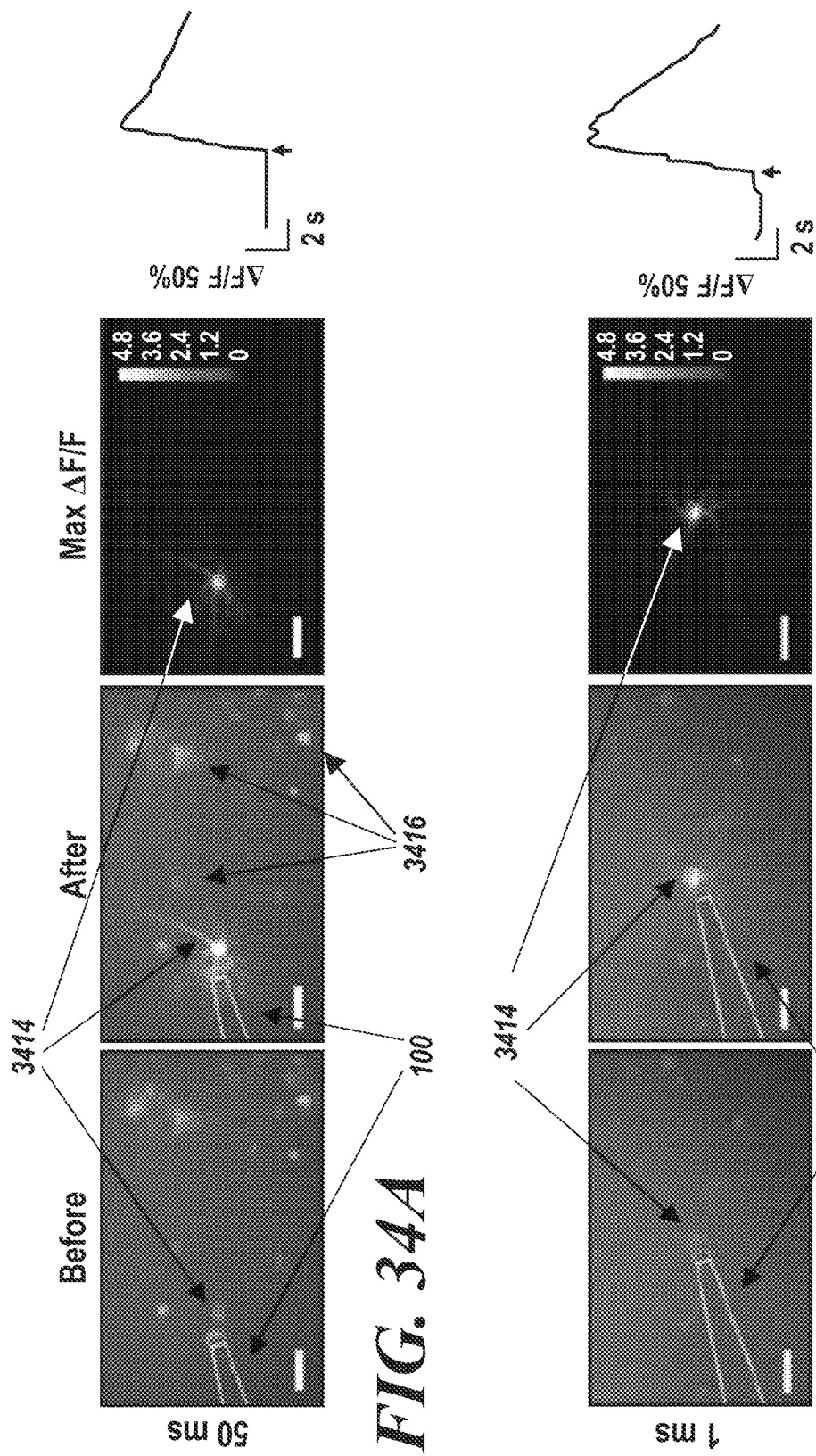
FIGS. 34A-34D illustrate fluorescence images of GCaMP6f-expressing neurons in response to TFOE stimulation.

According to the embodiments herein, TFOE stimulation of primary neurons with single cell precision can be produced by the devices and methods of the present disclosure. To test whether the TFOE 100 provides sufficient spatial precision when modulating a single neuron in culture, an illustrative examples involves preparing primary rat cortical neurons expressing GCaMP6f and performing calcium imaging using an inverted wide field fluorescence microscope. FIGS. 34A and 34B are fluorescence images and calcium traces in sparse population stimulated by TFOE with a laser duration of 50 milliseconds and 1 millisecond, respectively (fluorescence images with peak intensity after stimulation are shown as "after"; arrows: laser onset). Controlled by a micromanipulator, a TFOE 100 can placed approximately 5 microns away from a targeted neuron 3414. A 3-nanosecond pulsed laser at 1030 nm and 1.7 kHz repetition rate can be used to deliver laser pulses of 50 milliseconds duration at an average power of 7.8 mW, corresponding to 85 pulses. Thereby, calcium transients can be observed immediately after laser onset for the targeted neurons, while other neurons 3416 approximately 50 μm to 70 μm away from the tip remained unaffected, illustrated in FIG. 34A, indicating high spatial resolution of TFOE stimulation. The calcium transient with max ΔF/F of 135%±83% (N=6 from 3 cultures, data in mean±SD) indicates successful activation of the targeted neuron likely through firing of multiple action potentials evoked by TFOE stimulation. To further improve the temporal resolution, a laser pulse train of 1 millisecond (2 pulses) at 11.4 mW power can be delivered to the TFOE 100. Successful activation of single neurons 3414 can also be observed with a max ΔF/F of 106% 61% (N=8 cells from 3 cultures, data in mean±SD), illustrated in FIG. 34B.

According to the present disclosure, the TFOE 100 can thereby serve as a miniaturized ultrasound point source, with sub-millimeter confinement, composed of an optical diffusion layer 116 and an expansion layer 118 on an optical fiber. By modifying acoustic damping and light absorption performance, controllable frequencies in the range of 0.083 MHz-5.500 MHz are achieved and can further induce cell membrane sonoporation with frequency dependent efficiency. By solving the problem of compromise between sub-MHz frequency and sub-millimeter precision via breaking the diffraction limit, it is envisioned that the TFOE 100 can provide region-specific drug delivery, gene transfection and neurostimulation. Further, it is contemplated that the control group of 1 millisecond TFOE 100 with 3 μM tetrodotoxin (TTX) will show no activation, confirming that the calcium increase which may be observed in experimental groups resulted from Na+channel-dependent action potentials. According to the embodiments herein, the laser only group with a pulse train of 1.0 s and 11.4 mW power using a tapered fiber without the coating will show no activation, therefore, the effect of the laser on the neuron activity can be excluded.

Figure 34C:
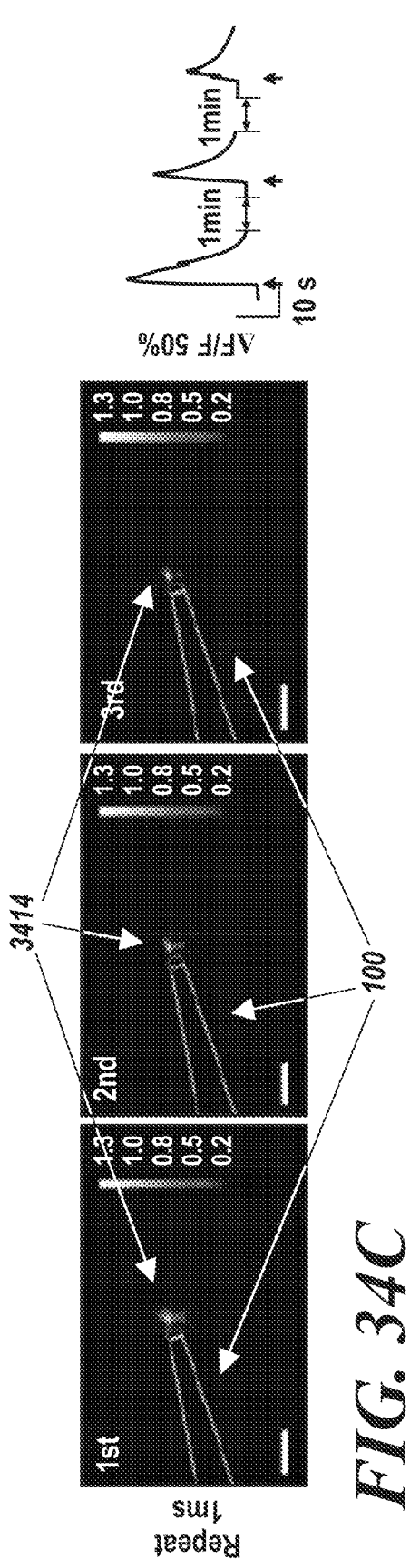
Figure 34D:
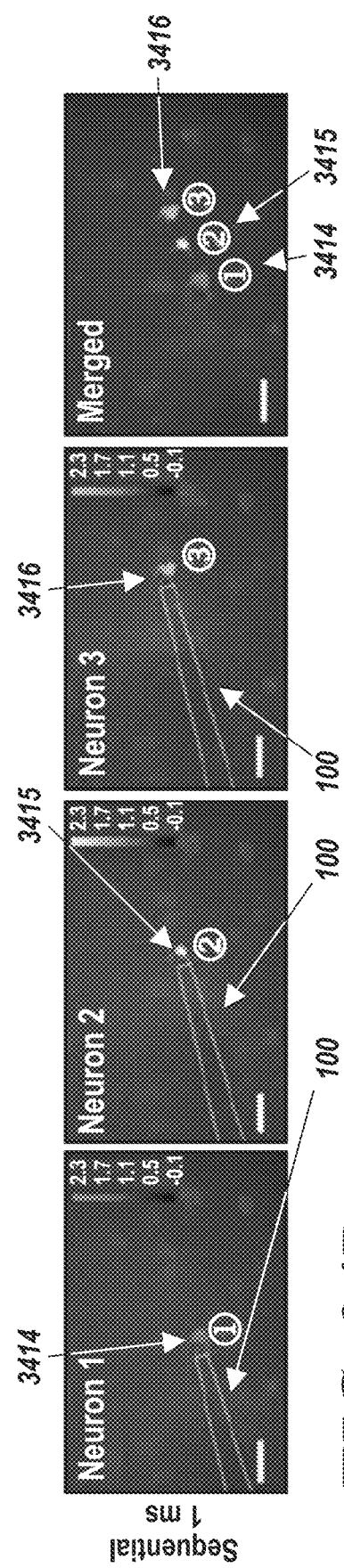

According to the embodiments of the present disclosure, TFOE 100 can trigger neural activation reliably and repeatedly. FIG. 34C shows the fluorescence intensity of the same neuron 3414 upon repeated TFOE 100 stimulation for three times. It is envisioned that 1 millisecond laser duration is utilized for each stimulation with an interval of 1 min between each recording period. Successful activation was achieved for each stimulation on the same neuron 3414, which can confirm the neuron's 3414 viability after TFOE 100 stimulation. A decrease in max ΔF/F for each sequential stimulation was observed, which can be attributed to calcium depletion or spike frequency adaptation. In addition, in FIG. 34D, the spatial precision of the TFOE 100 stimulation using three neurons selectively targeted by the TFOE 100 can be demonstrated. These three neurons 3414, 3415, and 3416, have an edge-to-edge spacing of 25±2 microns. The TFOE 100 can be sequentially placed about 5 microns away from each of the three targeted neurons 3414, 3415, and 3416. The maximum fluorescence intensity change (ΔF/F) can be labeled for each neuron 3414, 3415, and 3416, respectively, as illustrated in FIG. 34D. Importantly, fluorescence increase can be observed only for the selectively targeted neuron without simultaneous activation of the other two neurons, indicating that TFOE stimulation provides a spatial resolution of less than 25 µm. These results collectively confirm that TFOE 100 can stimulate single neurons reliably and repeatability.

Figure 35A:
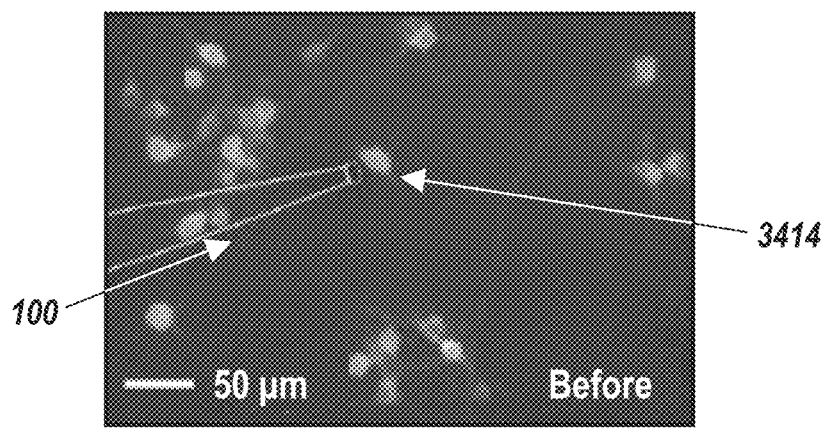
FIGS. 35A-35C are images of pulse energy dependence of TFOE stimulation.
Figure 35B:
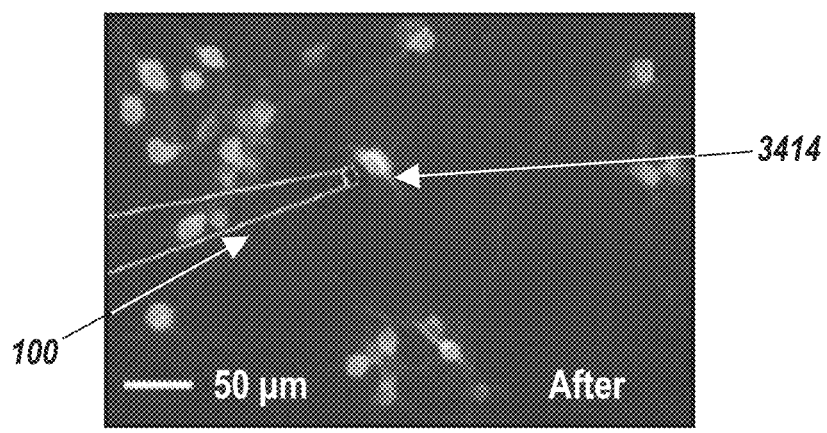
Figure 35C:
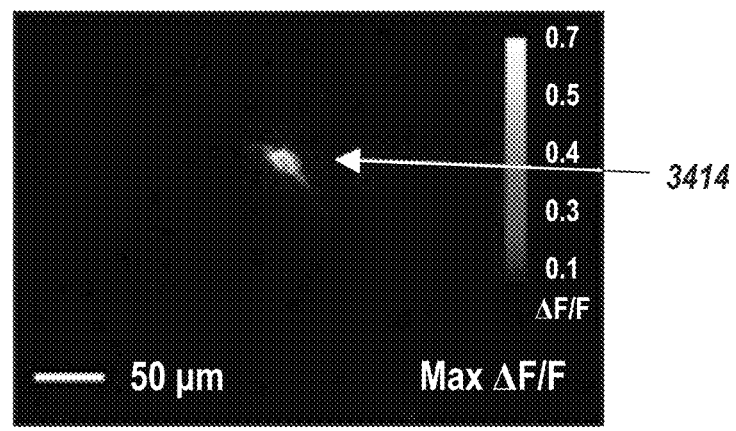
Figure 35D:
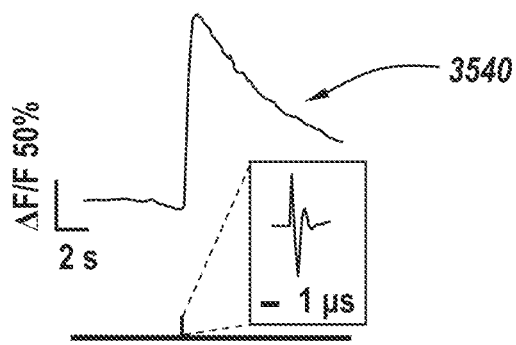
FIG. 35D is a graph of calcium trace of the targeted neuron which has undergone single pulse stimulation.
Figure 35E:
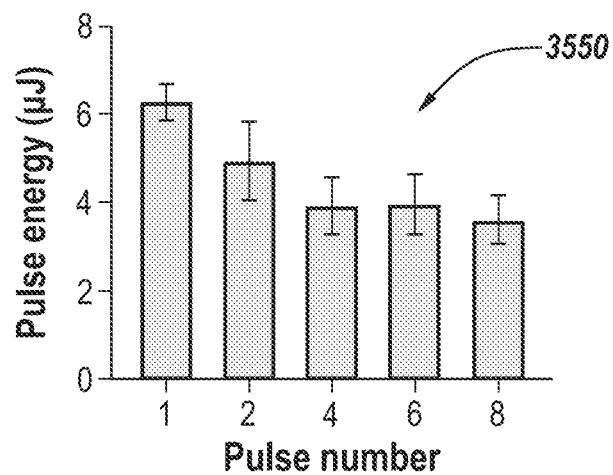
FIG. 35E is a graph of the pulse energy threshold for successful neuron stimulation as a function of pulse number.

According to the embodiments herein, the stimulation effect of single optoacoustic pulse on neurons can also be manipulated. In this way, the same nanosecond pulsed laser can be used to deliver a single laser pulse to the TFOE. TFOE stimulation of the GCaMP6f expressing primary cortical neuron with different laser pulse energy can be performed under the single pulse condition. FIGS. 35A-35C are images of pulse energy dependence of TFOE stimulation at, for example, 50 microns. Thereby, FIGS. 35A-C provide fluorescence images of GCaMP6f expressing neurons 3414 before (FIG. 35A) and after (35B) TFOE 100 stimulation with a single pulse, and also visualize max ΔF/F (35C). FIG. 35D is a graph of calcium trace 3540 of the targeted neuron 3414 which has undergone single pulse stimulation (line: onset of optoacoustic stimulation with zoom-in showing a representative optoacoustic waveform). No calcium transient can be observed until the pulse energy reached 6 µJ/pulse. It is envisioned that the width of the optoacoustic wave is approximately 1 microsecond. This capability could potentially enable acoustic control of neural circuits with unprecedented temporal precision required to mimic natural neural coding. FIG. 35E is a graph 3550 of the pulse energy threshold for successful neuron 3414 stimulation as a function of pulse number (N=5-7).

The present disclosure further contemplates the required laser energy for a given pulse number for successful neuron stimulation. In previous ultrasound studies, continuous wave and pulsed ultrasound with varied intensities and durations has been applied for neuron stimulation. The relationship between temporal-averaged US intensity and response amplitude or success rate was found to be negative or positive. Given these studies, the present disclosure pursues a statistical investigation of the behavior of neurons in response to acoustic stimulation across multiple intensities and durations. Continuing with this application, first, the threshold of pulse energy for successful stimulation is defined as the laser pulse energy sufficient to induce a maximum fluorescence intensity change (Max ΔF/F) greater than 20%, since Max ΔF/F of 20% GCaMP6f can be identified to correspond to ≥1 action potential. It is envisioned that the threshold energy shows a monotonic decrease from 6.3 µJ, 4.9 µJ to 3.9 µJ when increasing the pulse number from 1, 2 to 4, respectively, and it remains relatively constant at 3.9 µJ and 3.6 µJ when the pulse number increases to 6 and 8, respectively. These results demonstrate the following: first, the decrease of the energy threshold when the laser pulse number increases in the range of 1 to 4 shows that under the small pulse energy condition, subthreshold depolarizations accumulate with increasing pulse numbers. Second, the flattening trend of the threshold energy from 4 to 8 pulses implies a presence of an energy threshold at around 4 µJ/pulse, below which the action potential can hardly be evoked with even further elongation of the pulse train.

Figure 36A:
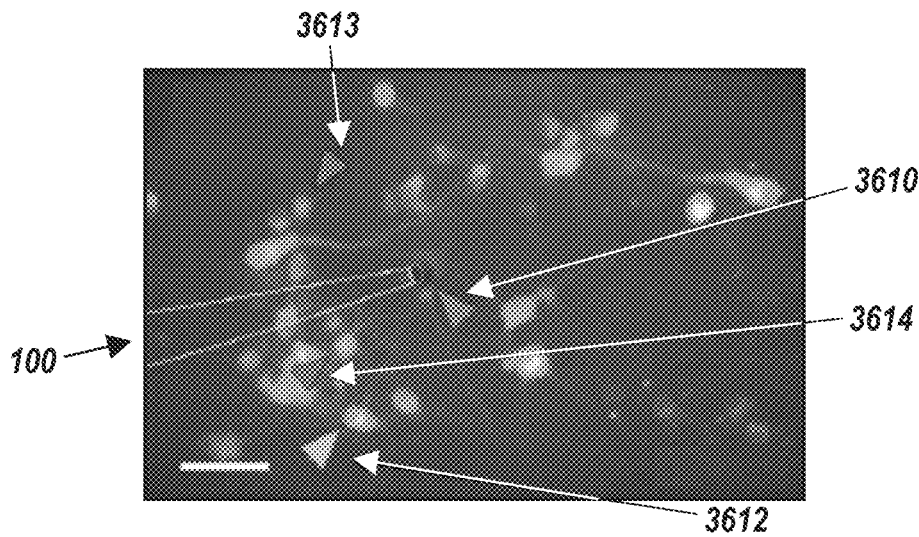
FIGS. 36A-36J include images and graphs of TFOE evoked sub-cellular stimulation on neurites.
Figure 36B:
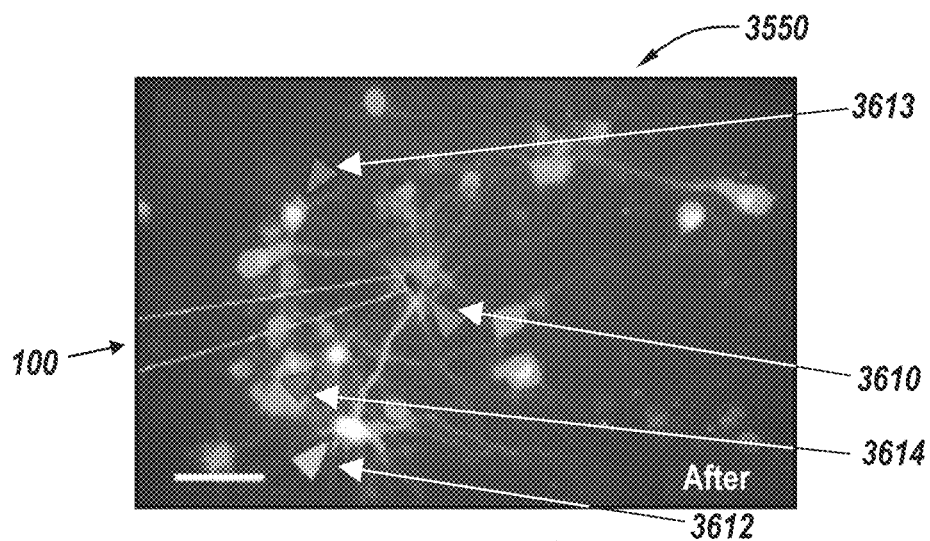
Figure 36C:
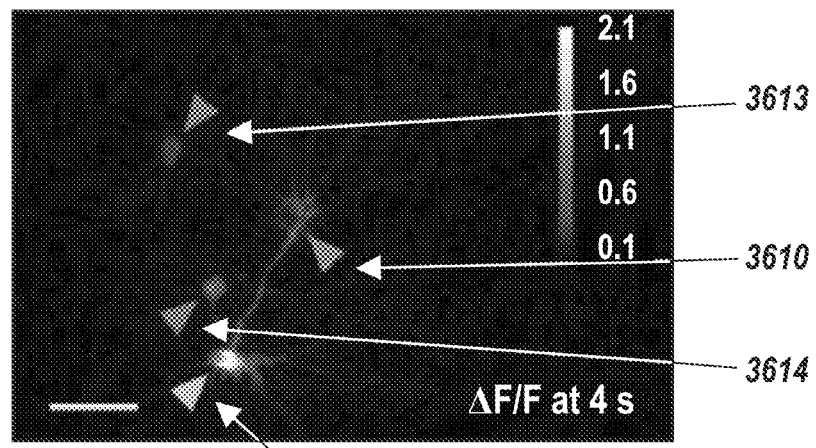
Figure 36D:
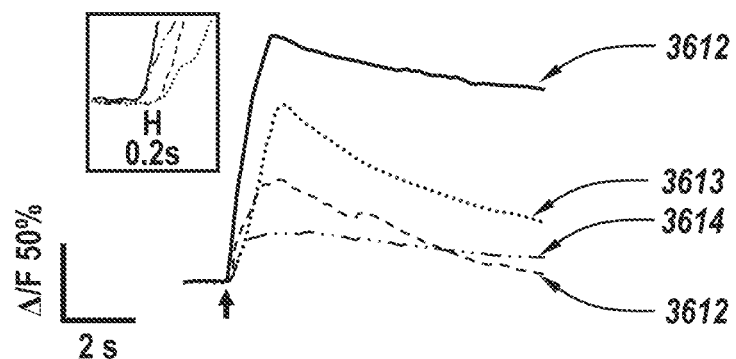

Upon successful stimulation of cultured primary neurons, the present disclosure further contemplates whether the TFOE 100 can target subcellular structures. To this end, the TFOE 100 can first carefully be placed above the targeted area where axons and dendrites densely populate without the presence of somas. It is envisioned that a 1030-nm laser pulse train with a duration of 1 millisecond, a laser power of 11.4 mW and a repetition rate of 1.7 kHz can be delivered to the TFOE 100. An increase in fluorescence intensity at the targeted area can be clearly observed after laser onset, indicating successful TFOE stimulation of targeted neurites and as illustrated in FIGS. 36A-D. FIGS. 36A and 36B respectively are images of before and after TFOE 100 evoked neurites activation with calcium wave propagating along neuron network (arrows: targeted area 3610, neuron 1 (3612) and neuron 2, 3 (3613 and 3614 respectively). FIG. 36C is an image of ΔF/F of calcium signal at 4 s after laser onset (scale bars: 50 µm). FIG. 36D is a graph of calcium traces of targeted area (3610), neuron 1 (3612) and neuron 2 and 3 (3613 and 3614 respectively), as labeled in 36A (inset: zoom-in of calcium signals immediately after the laser onset; black arrow: laser onset). Three different calcium dynamics can be captured through imaging throughout the field of view. First, a slow propagation of calcium wave initiating from the targeted region in the neural network can be observed after TFOE stimulation. It is envisioned that the speed of the calcium wave propagation can be calculated to be 75.2 µm/s, which is in agreement with the propagation speed of dendritic calcium wave induced by synaptic activity or by activity of metabotropic glutamate receptors (mGluRs) and backpropagating action potentials, which generated a speed of ~70 µm/s42. Second, 4 sites in the field of view will show elevated fluorescence signals prior to the spreading of calcium wave, as illustrated in FIG. 36C. The neurites in the targeted region (3610 in FIGS. 36A-C) and a specific neuron 1 (labeled 3612 in FIGS. 36A-C) with axon directly connecting to neurites in the targeted region showed fast calcium transients immediately after laser onset (FIG. 36D), which resembles backpropagation of action potentials. Considering that an unmyelinated axon would conduct action potential spikes at a speed of 500 µm/milliseconds to synapses, the propagation from neurites to neuron 1 (3612 in FIGS. 36A-C) over a distance of approximately 100 µm only requires 0.2 milliseconds. Therefore, the difference in the calcium transient onset for neuron 1 (3612 in FIG. 36D) and the targeted area (3610 in FIG. 36D) will be non-detectable by the camera with a sampling interval 50 milliseconds. Third, neuron 2 and 3 (labeled 3613 and 3614 respectively in FIGS. 36A-C) in the vicinity but without axons connecting to the targeted area showed an activation delay of ~0.2 s (FIG. 36D, inset) with similar temporal dynamics. This signaling can be likely attributed to action potential evoked through synaptic transmission, since it showed a faster propagation speed than the calcium wave.

Figure 36E:
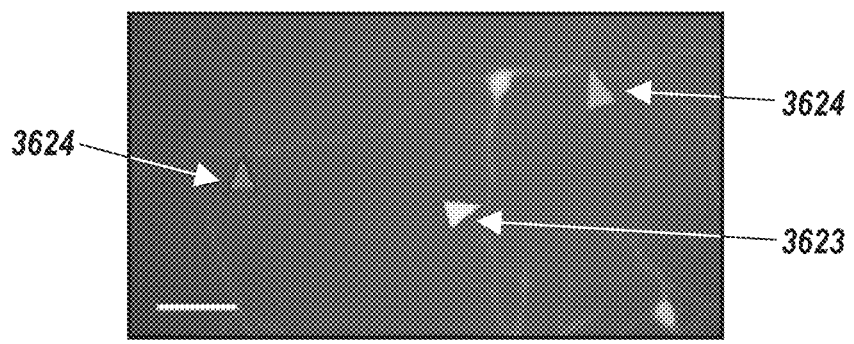
Figure 36F:
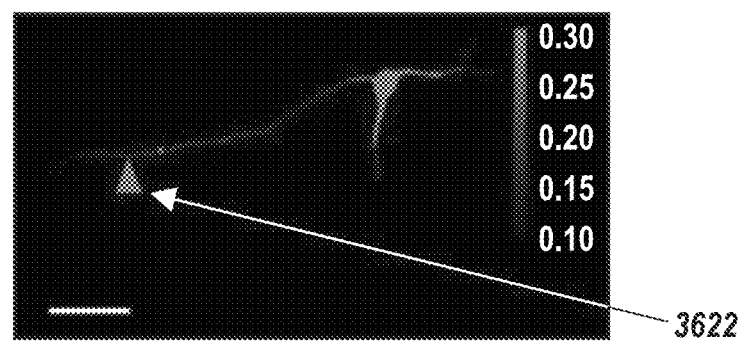
Figure 36G:
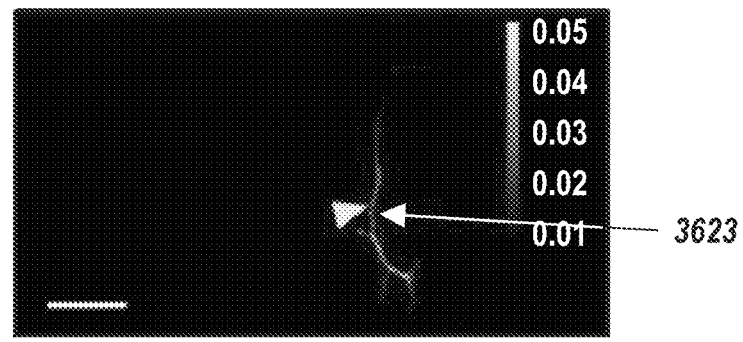
Figure 36H:
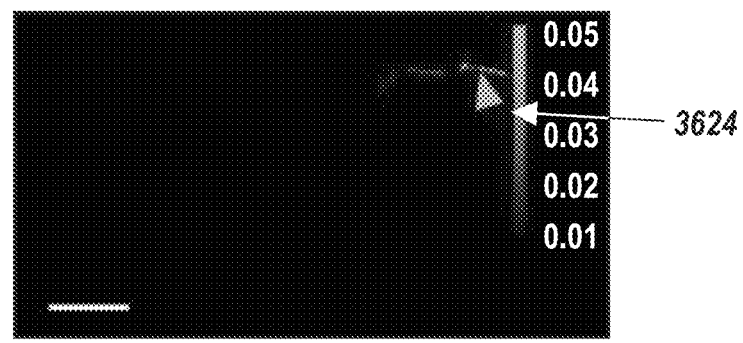
Figure 36I:
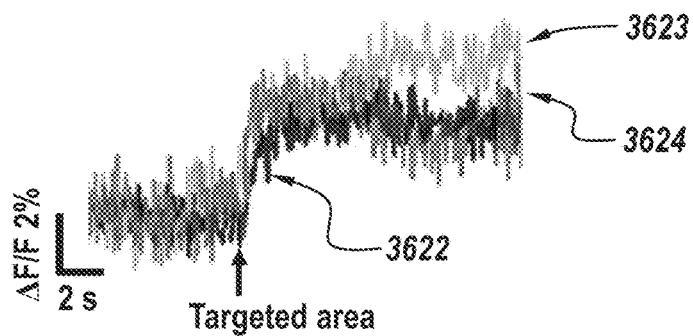
Figure 36J:
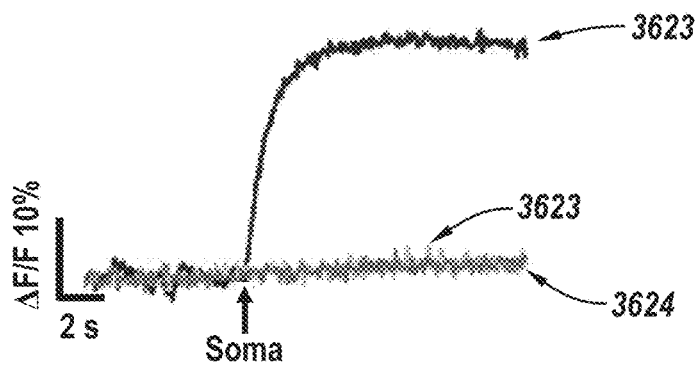

This capability of TFOE induced stimulation on subcellular structures, specifically on axons and dendrites, can then utilized to elucidate whether axons and dendrite have distinct response profiles to optoacoustic stimulation. In FIG. 36E, three neurites in a multipolar neuron were targeted selectively by the TFOE 100. Targeted TFOE stimulation 100 on one of the neurites (3622 in FIGS. 36E and F) induced strong calcium activation at the soma with no delay (FIGS. 36F and J). Thus, this neurite 3622 is identified as an axon, since such propagating activation resembles backpropagation of action potentials in an axon. Distinctively, targeted TFOE 100 stimulation of the other two neurites (3623 and 3624 in FIGS. 36E, G, and H) did not induce any activation at the soma (FIG. 36G-J). Thus, they can be identified as dendrites. FIGS. 36F-H illustrate maximum ΔF of calcium signal upon stimulation of different areas. Neuronal dendrites are known to integrate synaptic inputs from upstream neurons, which involves summation of stimuli that arrive in rapid succession, entailing the aggregation of inputs from separate branches. In the present case, the forward propagation of a single dendrite may be found to be insufficient to evoke action potentials at the soma. The differences between responses of the axon and dendrites upon acoustic stimulation at the single cell level are shown to be repeatable across multiple neurons. FIG. 36I is a graph of calcium traces measured at the targeted neurites as labeled in 36E by 3622, 3623 and 3624 arrows, respectively. FIG. 36J is a graph of calcium traces measured at the soma upon stimulation of different neurites (arrows in 36I-J: laser onset). Collectively, these data reveal differential response dynamics of axons and dendrites to optoacoustic stimulation for the first time, enabled by subcellular targeting capability of TFOE 100.

According to the present disclosure, a key advantage of single-neuron TFOE 100 stimulation is the compatibility with intracellular patch clamp recordings. While the calcium response to the stimulation has limited temporal resolution, direct recordings using intracellular patch clamp recordings stand as the golden standard to study sub- and supra-threshold neuron activity. Conventional ultrasound easily disrupts the patch attachment between the glass and membranes, so intracellular patch clamp recordings have been challenging during conventional ultrasound stimulation. The optoacoustic stimulation methods and devices of the present disclosure has the advantage of the localized optoacoustic field with a minimized mechanical disruption; therefore, it can be recorded with patching, providing a new testing system to gain insights towards mechanical modulation of neural systems.

Figure 37A:
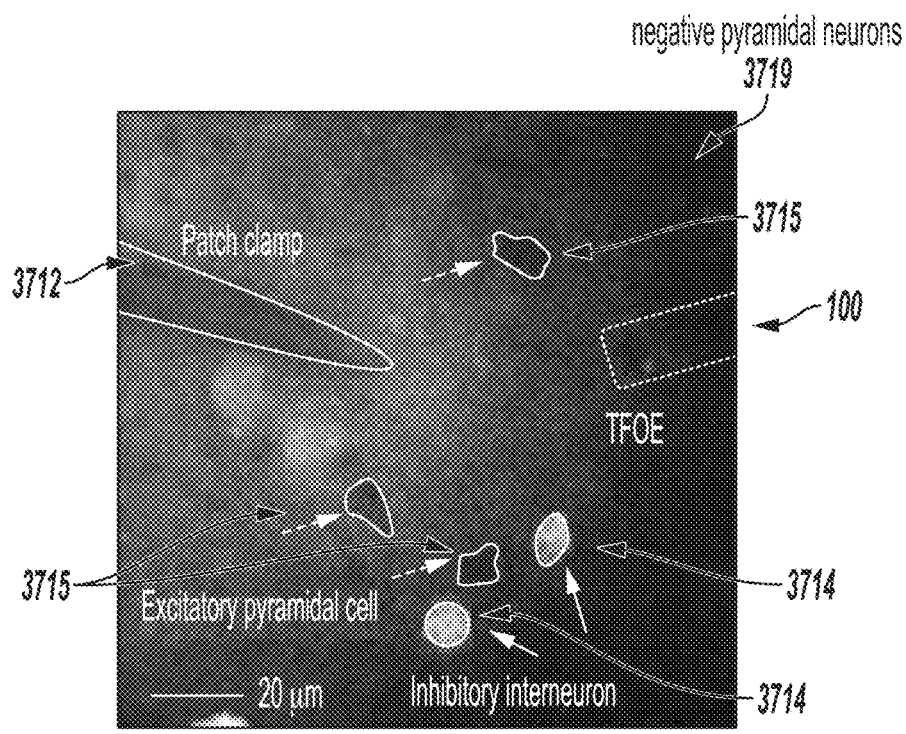
FIG. 37A-37F are images and graphical depictions of single neuron patch clamp with TFOE stimulation.
Figure 37B:
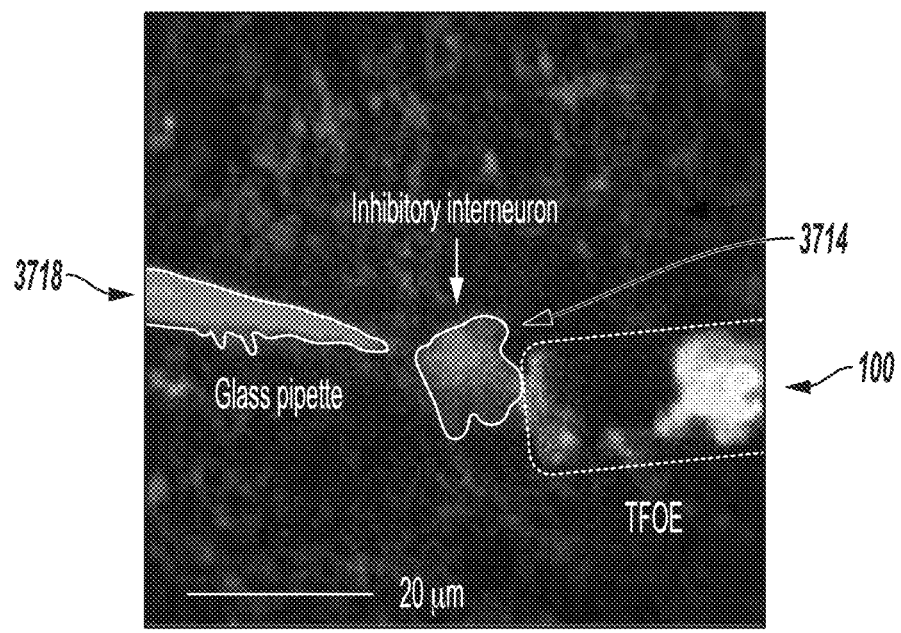

In this way, the present disclosure integrates TFOE 100 stimulation with patch clamp 3712 recording on single neurons. As an illustrative example, this can be conducted on mouse cortical slices to detect the direct electrical response to optoacoustic single neuron stimulation. FIGS. 37A-B provide two photon images of a patch clamp 3710 integrated with TFOE 100 in a mouse brain slice targeting GAD2-tdTomato negative pyramidal neurons 3719 and GAD2-tdTomato positive inhibitory interneurons 3714 (the patch pipette 3718 is visualized in FIG. 37B using the fluorescent dye Alexa Fluor 488 in the intracellular electrode solution). As shown in FIG. 37A, brain slices from mice expressing tdTomato in GAD2 interneurons to assist in visualization of specific cell types is presented. Thus, GAD2-tdTomato positive inhibitory interneurons 3714 and GAD2-tdTomato negative pyramidal neurons 3719 can be selectively targeted. TFOE 100 can be integrated with the patch pipette 3718 to induce depolarization leading to action potential generation in the targeted neurons.

Figure 37C:
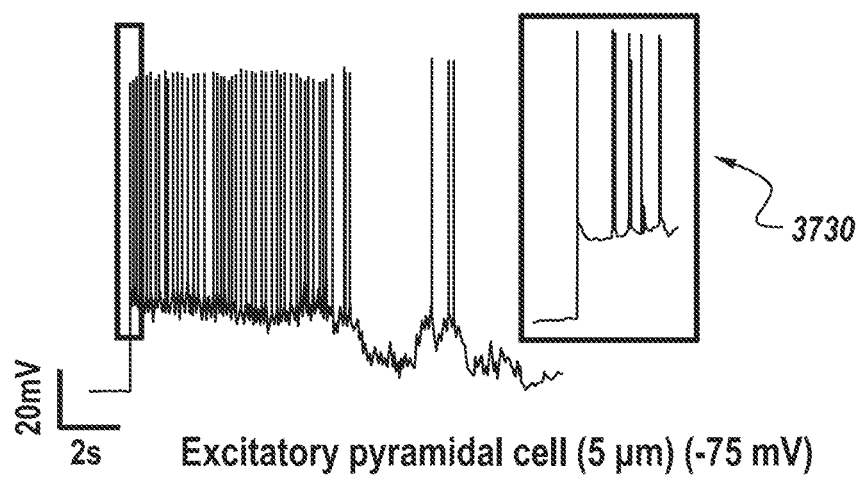
Figure 37D:
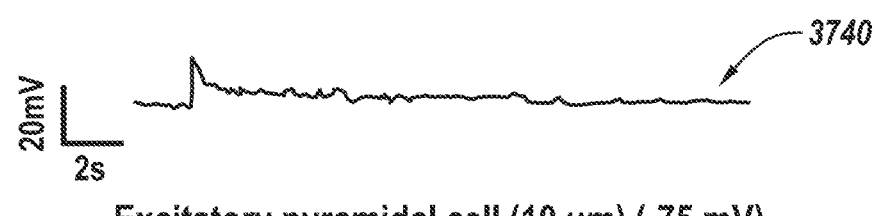

Also indicated in FIGS. 37C-F, the neuron membrane voltage can be measured precisely with an unprecedented stability upon TFOE 100 stimulation. According to embodiment of the present disclosure, for excitatory pyramidal cells 3715 under the current clamp 3712 mode, a train of action potential can be observed immediately after TFOE stimulation at 5 μm (as illustrated in FIG. 37C). FIGS. 37C and D are graphs of membrane voltage response in an excitatory pyramidal cell upon TFOE stimulation (5 milliseconds) at a distance of ~5 μm (graph line 3730 in FIG. 37C) and ~10 μm (graph line 3740 in FIG. 37D). This result is consistent with previous calcium imaging with ΔF/F greater than 100% in fluorescence change as presented in FIGS. 34A-B and 35D. When the TFOE was moved from 5 to 10 μm away from the neurons 3714 and 3715 (FIGS. 37C and D), it is contemplated that the action potentials give way to a subthreshold depolarization, indicating a high confinement of the acoustic field in the tissue.

Figure 37E:
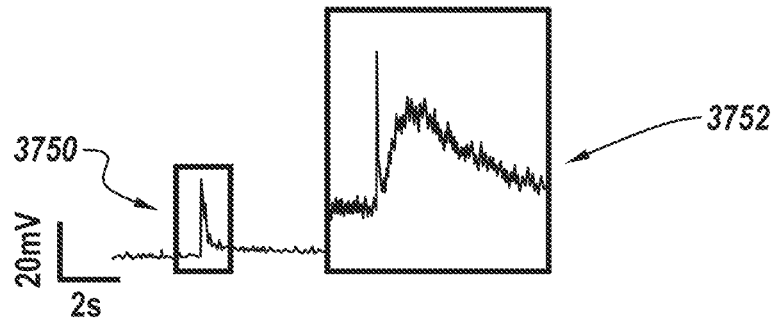
Figure 37F:
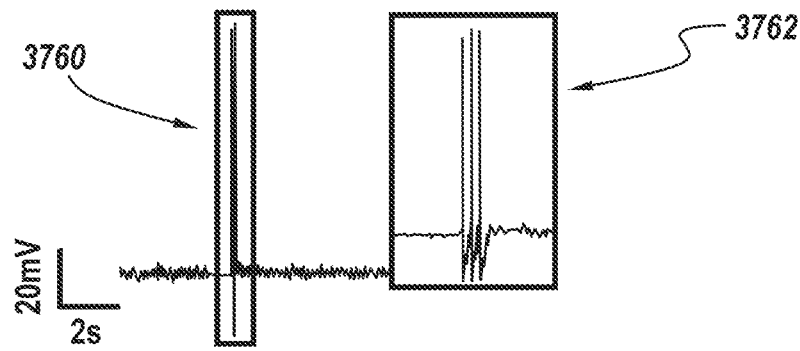

Next, the present disclosure involves targeting tdTomato positive interneurons. FIGS. 37E and F are graphs of voltage response in an inhibitory interneuron upon TFOE stimulation at ~5 μm at the membrane voltages of −75 mV (graph lines 3750 and 3752 of FIG. 37E) and −40 mV (graph lines 3760 and 3762 of FIG. 37F) (laser: 11.4 mW, 1.7 kHz, 5 milliseconds duration). TFOE induced subthreshold depolarization in inhibitory interneurons held at −75 mV, and the electrical response over time after stimulation showed two components (3750 of FIG. 37E). The first sharp peak 3750 in FIG. 37E could be due to the direct interruption of the membrane integrity by the acoustic wave, and the following broad peak 3752 is likely due to an inward channel current, thus indicating the possible involvement of ion channels. With the membrane depolarized via injecting positive currents to near −40 mV, a short train 3762 of three action potentials was observed upon TFOE stimulation (FIG. 37F). The distinct response of excitatory pyramidal neuron and inhibitory interneurons to acoustic stimulation is likely contributed by multiple factors including a unique intrinsic action potential threshold of these two cell types, as well as distribution of mechanosensitive ion channels that have different response dynamics to acoustic radiation force. Thereby, the TFOE 100 provides an unprecedented stable ultrasound source compatible with patch clamp 3712 recordings, holding promise to shed light on the mechanism of acoustic induced neuron stimulation.

The tapered fiber optoacoustic emitter, or TFOE, is comprised of a nanosecond laser, an optic fiber with the tip engineered, an optoacoustic coating and a set of operating parameters to minimize and eliminate photothermal effects. It is envisioned that when excited by laser pulses, the coated tip can generate omnidirectional acoustic wave locally at the fiber tip through the optoacoustic effect. The acoustic wave generated is highly localized within a sub-100 micron distance from the TFOE tip, and can be utilized to activate neurons with single neuron precision. Additionally, the fiber tip can be engineered to offer a range of resolutions from single neuron to sub-millimeter resolution, and can operate together with electrophysiology recording of single neuron activation through a patch clamp.

Notably, the TFOE 100 is novel in its ability to deliver neuromodulation with sub-100 micron precision. It is envisioned that the fiber optoacoustic generator of the present disclosure can produce effective ultrasound with much less heat generated than other fiber optoacoustic generators. Additionally, the TFOE produces a local ultrasound field confined within a sub-100 micron distance away from the fiber tip, which is tighter than other fiber-based optoacoustic devices. Together with the omnidirectional acoustic propagation feature allowing the acoustic intensity to attenuate fast over the distance, the TFOE can more effectively and efficiently produce neural activation at high spatial precision.

According to the present disclosure, the TFOE can be comprised of a compact 1030-nm, 3-nanosecond laser, a 200-μm diameter, 0.22 NA multimodal fiber with a tip tapered, and a layer coating at the tapered fiber tip giving an overall coated tip diameter in the range of 10 to 100 micron in thickness. Through the optoacoustic process, the pulsed laser energy can be converted into acoustic waves generated at the TFOE tip, and subsequently, the acoustic waves excite neurons in the proximity to the tip. It is envisioned that the TFOE coating can be a single layer nano-composite mixed from 5% to 15% (w/w) multiwall carbon nanotube in Polydimethylsiloxane (PDMS).

It is contemplated by the present disclosure that with its high optical absorption and thermal conduction efficiency, carbon nanotubes comprising the TFOE can completely absorb the laser and convert it into heat. The heat can then be transferred to surrounding PDMS and generate optoacoustic waves that propagate in an omnidirectional manner. In this way, the TFOE exploits the optoacoustic effect and generates acoustic wave with a spatial confinement around m, offering an unprecedentedly high spatial resolution for ultrasound source.

Further, the TFOE of the present disclosure provides improvements in both spatial resolution and optoacoustic conversion efficacy, achieved by fiber engineering, material modification and a novel deposition method. According to the present disclosure, the optoacoustic wave generated by TFOE can directly activate individual cultured neurons and generate intracellular Calcium transients. Thereby, the TFOE activates neurons within a radius of m around the fiber tip, delivering single neuron resolution over conventional piezo-based low-frequency transducers and previous TFOE devices.

In this way, the TFOE can provide acoustic stimulation of single cells and subcellular structures, such as axons and dendrites. Temporally, single acoustic pulse with duration of 1 microsecond can achieve desired neuron stimulation, or the shortest known duration of acoustic stimuli for successful neuromodulation. Importantly, the near field acoustic wave generated by TFOE can allow optoacoustic stimulation with simultaneously monitoring cell response using whole cell patch clamp recording, while inducing negligible photothermal effects. Additionally, it is contemplated that the TFOE tip coating structures, geometry and material can be altered to achieve various ultrasound spatial propagation pattern, different ultrasound intensity and frequencies.

According to embodiments of the present disclosure, electrical, ultrasound, and optogenetic stimulation treatment can promote neurite outgrowth by way of delivering optoacoustic frequency by way of the TFOE 100. This is a key process for the functional repair of nervous tissue in the event of injury. In this way, the photoacoustic process of the present disclosure allows a non-genetic temporally and spatially precise stimulation of neural activity. According to embodiments of the present disclosure, the fiber-based photoacoustic emitter 100 (TFOE, or TFOE) demonstrates the feasibility of using photoacoustic effect in neural stimulation both in vitro and in vivo. Neurons 3910 of FIG. 39 indicate that results via an vitro calcium response, where the primary neurons are stained. TFOE 3800, like TFOE 100, measured via 3846 in FIG. 40A indicates likewise at 4020 of FIG. 40B when optoacoustic stimulation is applied for an in vivo LFP response. For both, neural stimulation can be applied reliably and repeatedly via the photoacoustic process of the present disclosure to promote neurite outgrowth and subsequent repair of nervous tissue.

Notably, it is envisioned that the TFOE 100 is thereby able to convert pulsed light energy into ultrasound pulses for cell modulation and regeneration purpose. It is contemplated that this optoacoustic material can be comprised of optical absorbers in an expansion matrix and can be used in different designs, such as films and 3D structures. The generated ultrasound can stimulate cells, such as different types of neurons placed near the TFOE material, or stimulate neurons inside a tissue if the material is designed to generate a focused ultrasound.

According to embodiments of the present disclosure, a hydrogel scaffold is integrated with the photoacoustic function through a nanocomposite approach to enable neuron regeneration. Hydrogel supports neural growth with silk fibroin when used for neuron culture, and also provides a controllable rate of biodegradation, tunable drug loading capability, optical transparency, and a tunable mechanical property. Further, carbon nanotubes can serve as an efficient photoacoustic agent. Carbon nanotubes, when used for neural stimulation, can provide high light-to-sound conversion efficiency. Additionally, broadband optical absorption allows for flexibility in choosing a laser system in future applications. Carbon nanotubes have minimal toxicity and are useful for confirmation in applications of living photoacoustic imaging.

Figure 7:
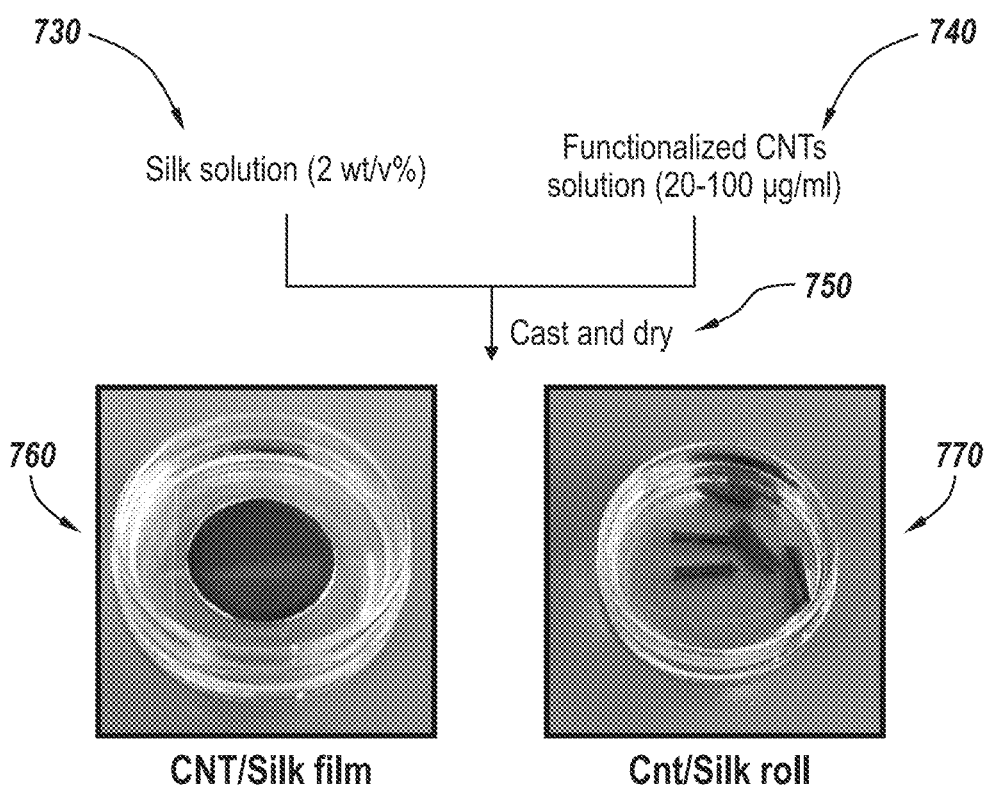
FIG. 7 is a diagram of the casting and drying of silk solution with functionalized CNTs solution to produce CNT/Silk film and/or roll.
Figure 8:
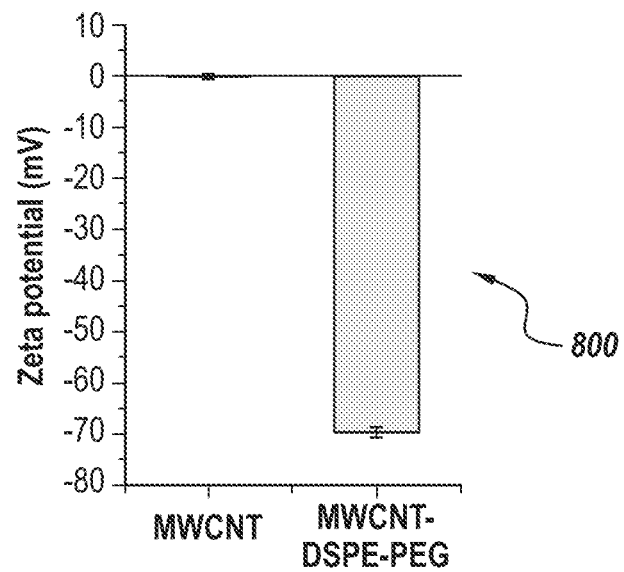
FIG. 8 is a graph of the zeta potential confirming the success of surface functionalization from the produced CNT/Silk film and/or roll.

According to embodiments of the present disclosure, PEG-functionalization enabled an all aqueous fabrication method 700 for the CNT/silk fibroin film that comprises the fiber-based photoacoustic emitter 100. Silk fibroin 710 was extracted into aqueous solution 720 by joining silk solution 730 (2 wt/v %) with functionalized CNTs solution 740 (20-100 μg/ml), and subsequently casting and drying the product at 750 to produce CNT/Silk film 760 or CNT/Silk roll respectively, as illustrated in FIG. 7, depending upon the mold. PEG-functionalization made CNT water dispersible and reduced toxicity. The surface functionalization results can be successfully confirmed with Zeta potential 800 in FIG. 8.

Figure 9:
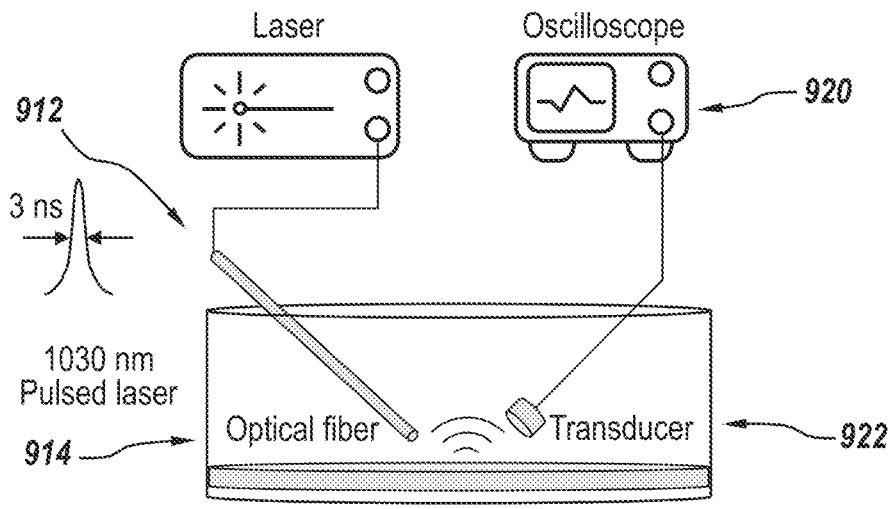
FIG. 9 is a schematic of acoustic measurement relating to the broadband acoustic wave generated by the CNT/Silk film.
Figure 10A:
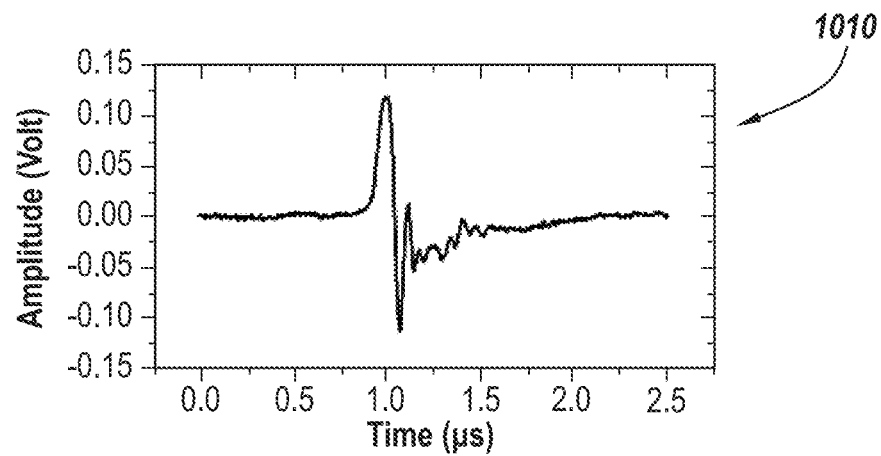
FIG. 10A and FIG. 10B are graphs depicting the resulting photoacoustic waves generated by FIG. 9.
Figure 10B:
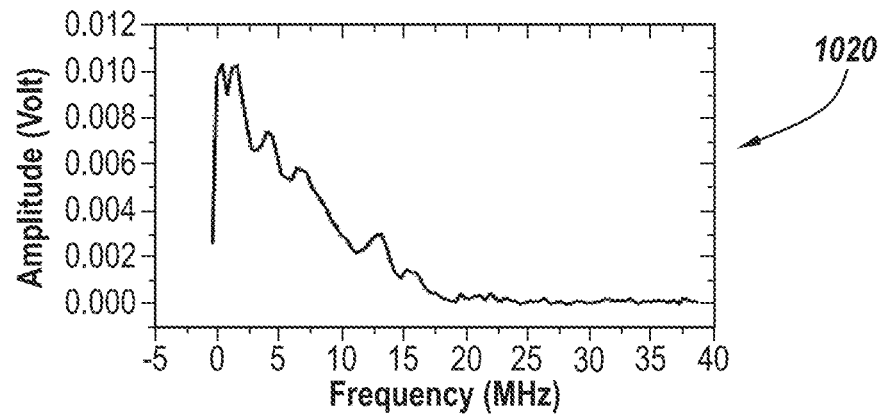
Figure 11:
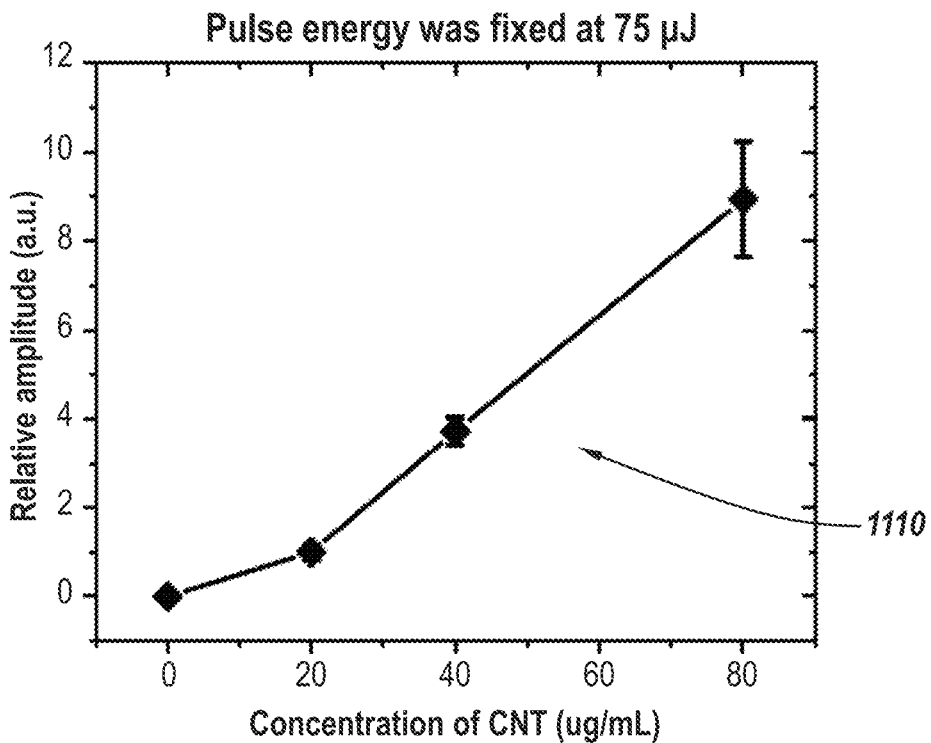
FIG. 11 is a graph of pulse energy fixed at 75 µJ when photoacoustic stimulation is manipulated by laser power.
Figure 12:
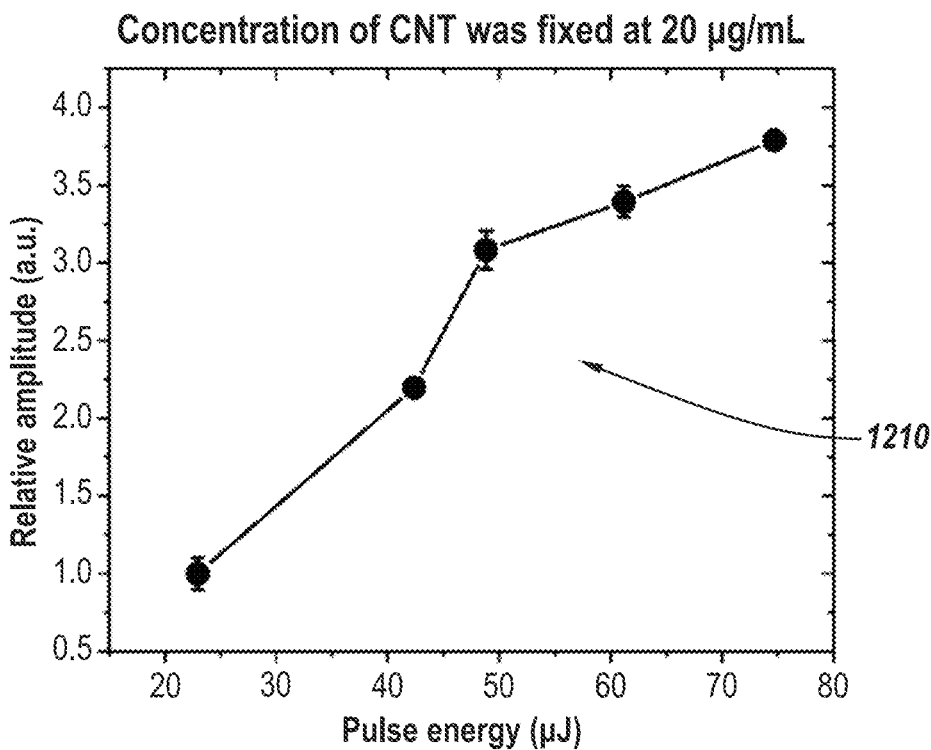
FIG. 12 is a graph of the concentration of CNT fixed at 20 µg/mL when photoacoustic stimulation is manipulated by the concentration of embedded CNT.

According to another aspect of the present disclosure, broadband acoustic waves can be generated by the CNT/silk fibroin film. For example, FIG. 9 illustrates a 1030 nm laser 910 with pulse width of 3 ns delivered to the CNT/Silk film though a multimode optical fiber 914 via a pulsed laser 910, with an illumination area of about 0.05 mm². The acoustic wave 912 was characterized using a 10 MHz transducer and recorded by the oscilloscope 920. As a result, a photoacoustic wave 912 was generated with a 1 us acoustic pulse width, broadband central frequency at 1.2 MHz, and pressure of 0.26 MPa at the pulse energy of 14.7 μJ, as illustrated in graph line 1010 in FIG. 10A and graph lines 1020 in FIG. 10B, as functions of time and frequency, respectively. It should be noted that photoacoustic stimulation requires appropriate pressure, which can be controlled by manipulating the concentration of embedded CNT and laser power. For the purposes of measuring this, $$P_0 = \Gamma \cdot A \cdot \frac{F}{l}$$

is calculated, where $\Gamma = \beta v^2/C_{p,}$ is characteristic length, A is light absorption coefficient, F is the laser fluence, 3 is the volumetric thermal-expansion coefficient, v is sound speed, and Cp is the specific heat capacity. As a light absorption material, a higher concentration of embedded CNT results in stronger acoustic waves due to its higher absorption coefficient, as seen in graph line 1110 in FIG. 11 (pulse energy fixed at 75 μJ as a function of CNT concentration μg/mL) and graph line 1210 in FIG. 12 (CNT concentration fixed at 20 μg/mL as a function of pulse energy μJ).

Figure 13A:
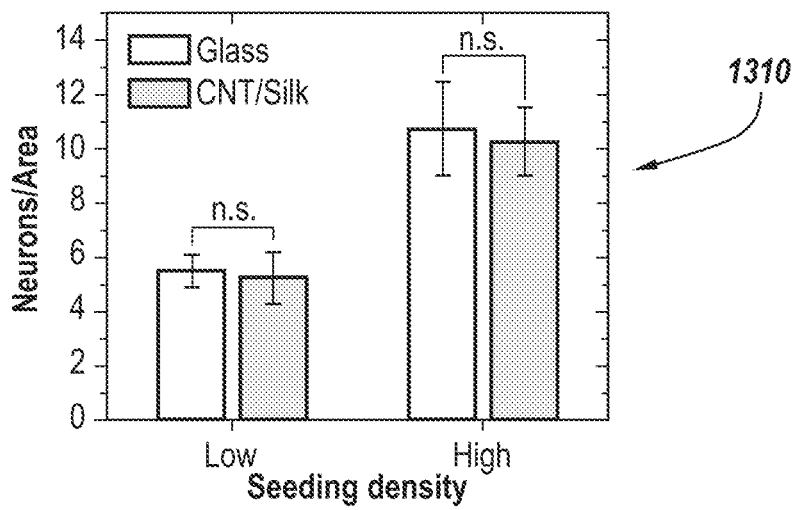
FIG. 13A is a graph confirming in vitro morphology as a function of neurons/area.
Figure 13B:
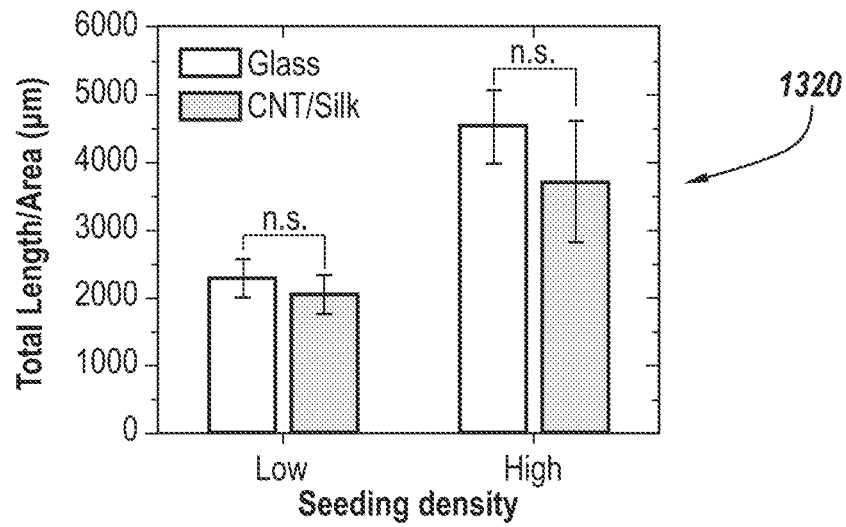
FIG. 13B is a graph confirming in vitro morphology as a function of total length/area.
Figure 13C:
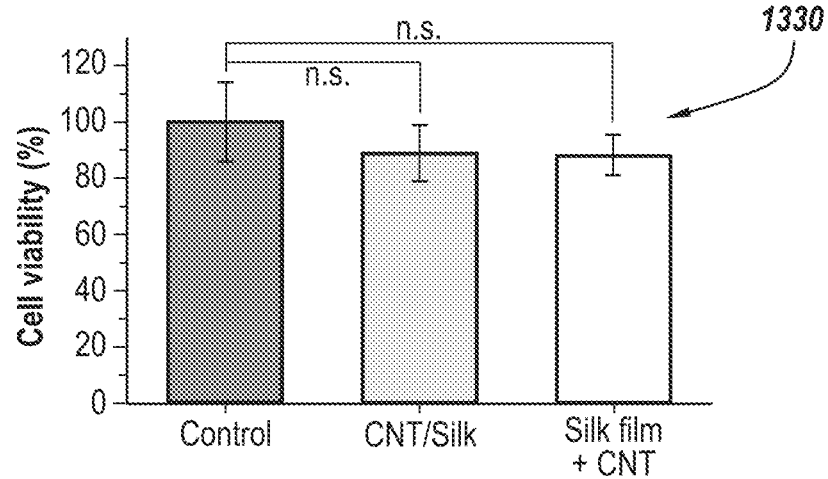
FIG. 13C is a graph confirming cell viability for control, CNT/Silk, and Silk film+CNT groups, respectively.

According to embodiments of the present disclosure, biocompatibility and negligible thermal effect can be confirmed via photoacoustic stimulation of nervous tissue. FIG. 13A is a graph 1310 confirming in vitro morphology as a function of neurons/area when comparing the produced CNT/Silk roll or film alongside a glass control group. FIG. 13B is a graph 1320 confirming in vitro morphology as a function of total length/area when comparing the produced CNT/Silk roll or film alongside a glass control group. FIG.

13C is a graph 1330 confirming cell viability for control, CNT/Silk, and Silk film+CNT groups, respectively.

Figure 14:
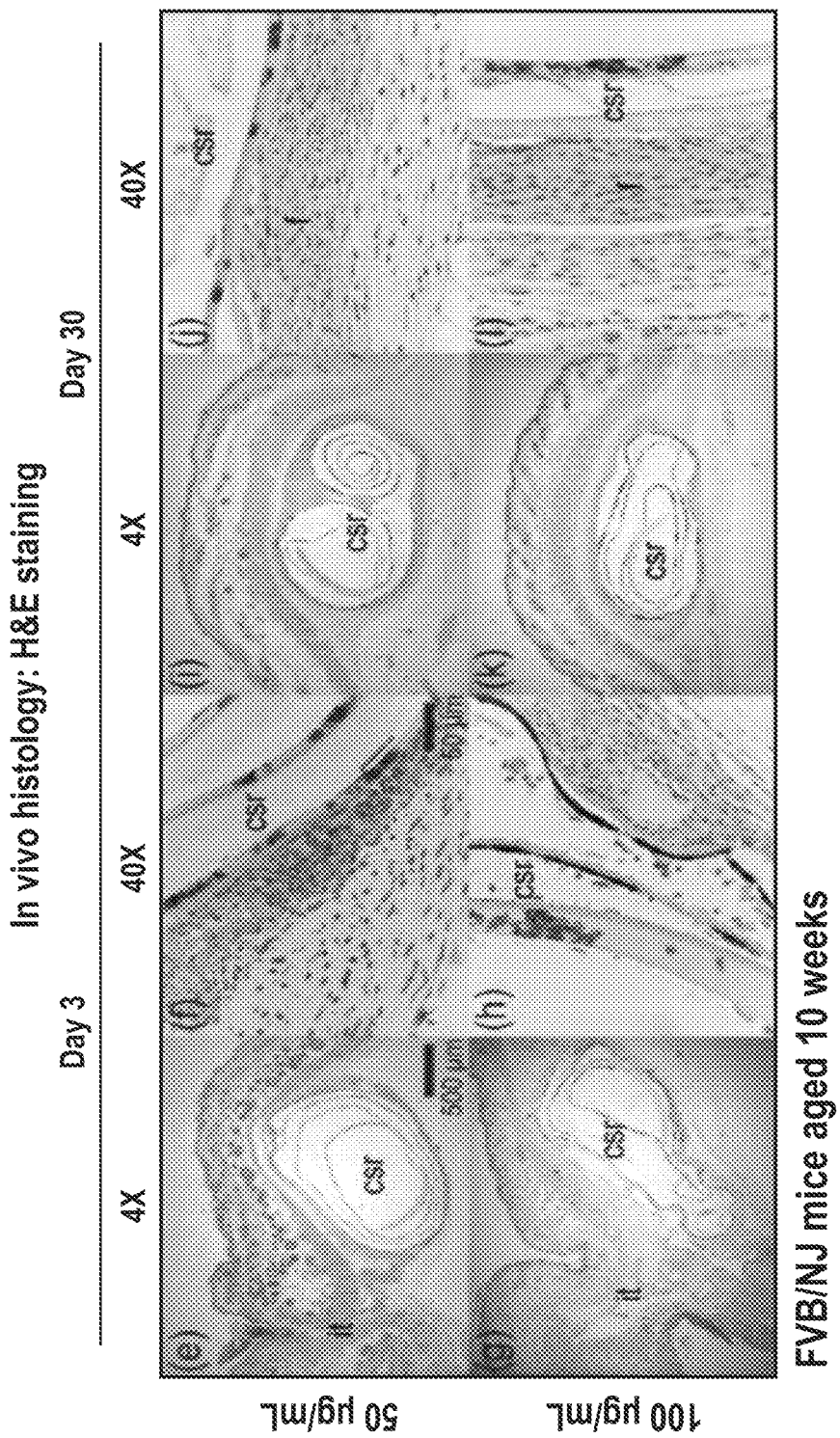
FIG. 14 includes images depicting in vivo histology in mice aged 10 weeks with H&E staining.
Figure 15:
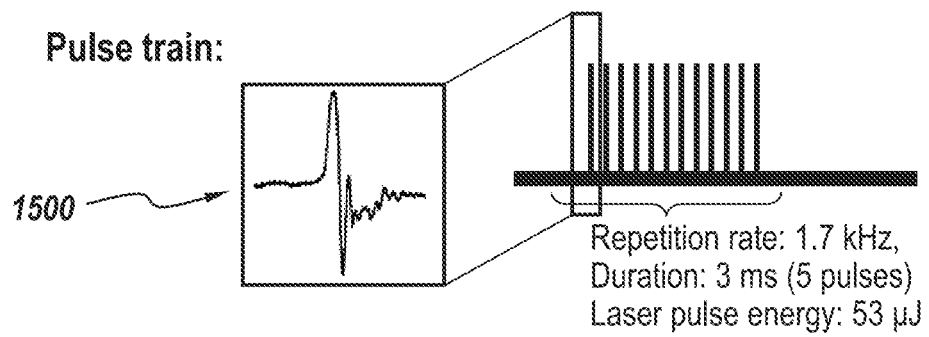
FIG. 15 provides a schematic depicting the pulse train confirming biocompatibility and a negligible thermal effect.
Figure 16:
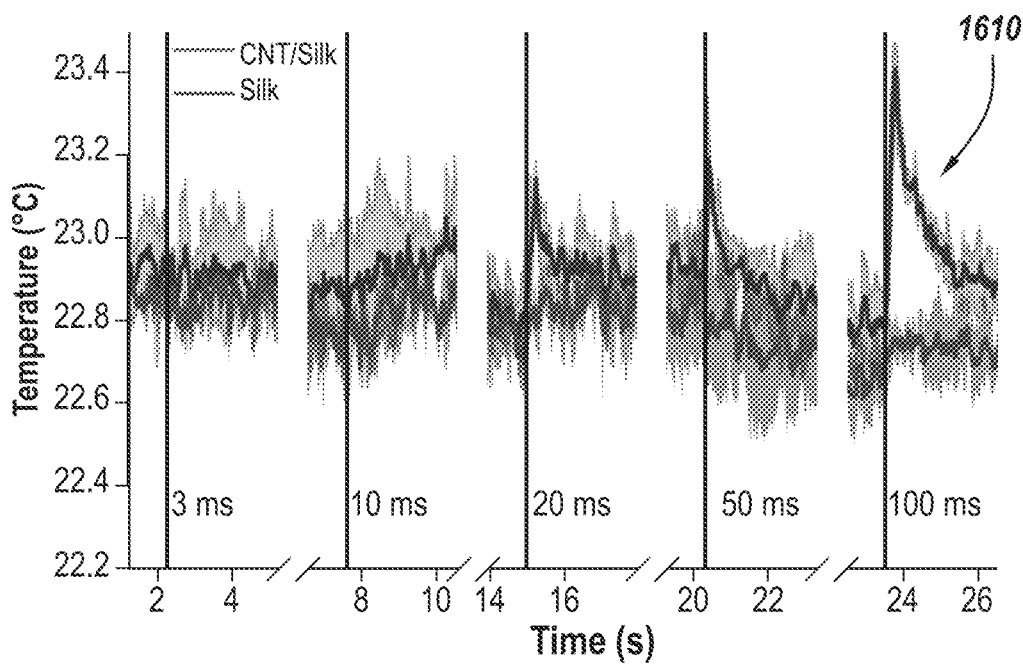
FIG. 16 is a graph depicting the performance of CNT/Silk vs. isolated silk as a function of temperature over time.

FIG. 14 includes images 1400 confirming biocompatibility and negligible thermal effects via photoacoustic stimulation of nervous tissue in vivo histology for mice aged 10 weeks with H&E staining. At 4× and 40× magnification levels, when exposed to 50 µg/mL and 100 µg/mL respectively, results were recorded at Day 3 and Day 30 intervals. Further, FIG. 15 provides a schematic depicting the pulse train confirming the biocompatibility and a negligible thermal effect at 1500. The repetition rate is set at 1.7 kHz, the duration 3 ms/5 pulses, and laser pulse energy at 53 µJ. FIG. 16 is a graph depicting the performance of CNT/Silk at graph line 1610 vs. isolated silk at graph line 1612 as a function of temperature over time, further confirming the improved photoacoustic capabilities of the CNT/Silk combination.

Figure 17:
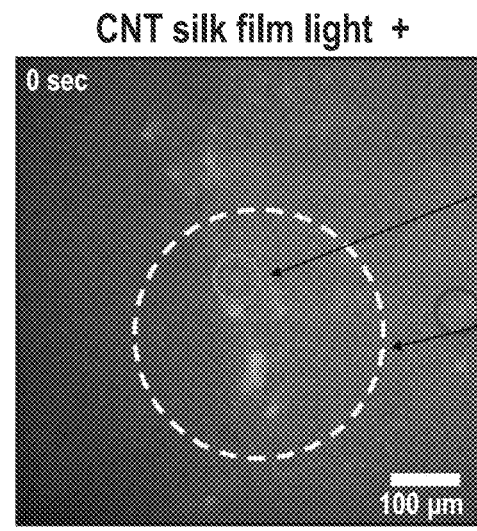
FIG. 17 is an image of the performance of CNT/Silk film when subjected to light with light illumination determining the region of activation.
Figure 18:
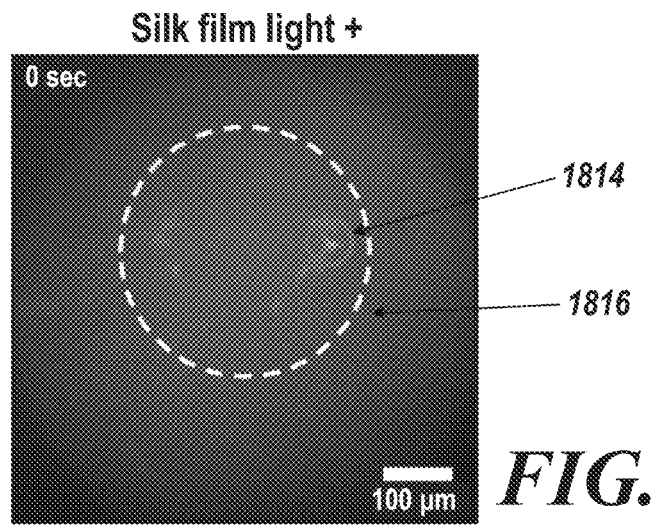
FIG. 18 is an image of the performance of silk film when subjected to light with light illumination determining the region of activation.
Figure 19:
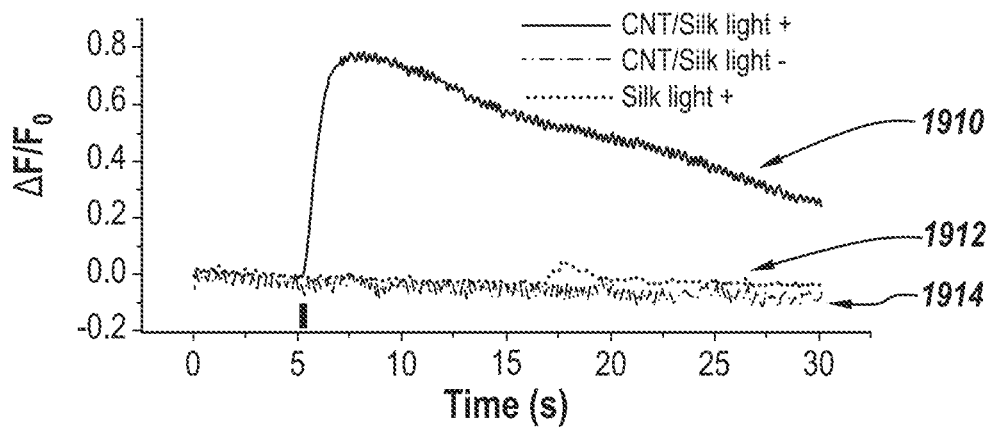
FIGS. 19 and 20 are graphs further depicting the performance of CNT/Silk when subjected to light, CNT/Silk when not subject to light, and silk film when subjected to light as a function of $\Delta F/F_0$ overtime.
Figure 20:
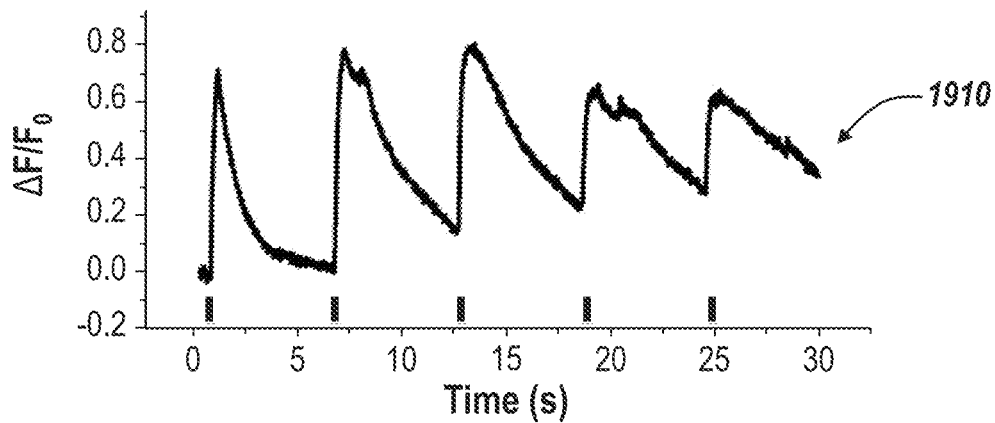

According to the exemplary embodiments herein, photoacoustic waves generated by CNT/Silk film stimulated neuronal activities reliably and repeatedly. To do so, laser pulse energy of 14.7 µJ (29.4 mJ/cm2) at 5 ms (8 pulses) can be applied to primary cortical neurons GCaMP6f transfected at day 4, as illustrated in FIGS. 17-20. FIG. 17 is an image at 100 microns of the performance of CNT/Silk film 1610 when subjected to light (CNT/Silk light+), with light illumination determining the region of activation 1710 (with the dash line 1712 indicating the laser illumination area). FIG. 18 is an image at 100 microns of the performance of silk film 1612 when subjected to light (Silk light+), with light illumination determining the region of activation 1814 (with the dash line indicating the laser illumination area 1816). To further illustrate this, FIGS. 19 and 20 are graphs depicting the performance of CNT/Silk when subjected to light at graph line 1910, CNT/Silk when not subject to light (CNT/Silk light−) at graph line 1912, and silk film when subjected to light as a function of $\Delta F/F0$ overtime at graph line 1914. Thereby, it can be confirmed that photoacoustic stimulation can reliably and repeatedly induce neural activation, and can also confirm the absence of damage to neural functions.

Figure 24:
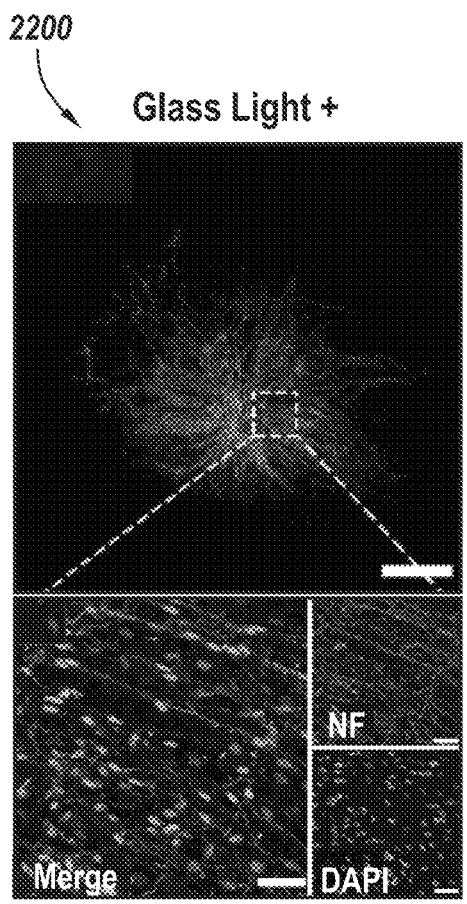
FIG. 24 is an image of glass light control group when subjected to light illumination.
Figure 25:
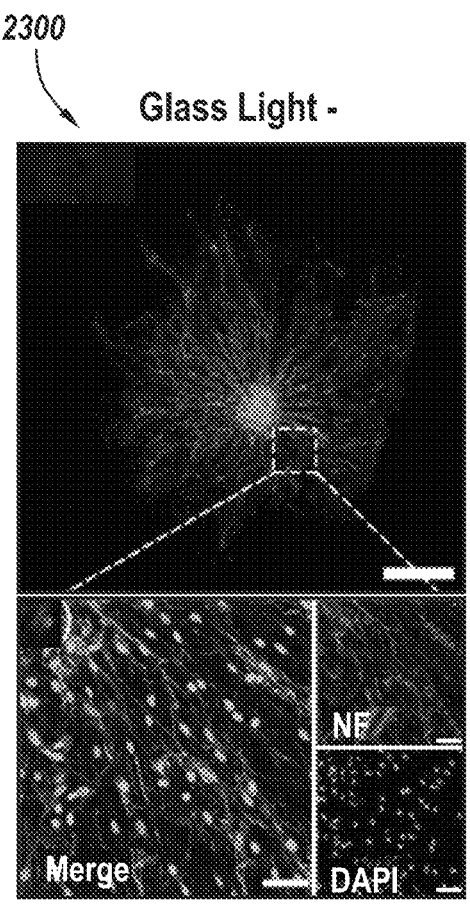
FIG. 25 is an image of glass light control group when not subjected to light illumination.

According to another aspect of the present disclosure, photoacoustic stimulation can promote neurite outgrowth. An illustrative embodiment can be observed via rat dorsal root ganglion (DRG) explants, as illustrated in FIGS. 21-26. FIG. 21 includes a schematic 2100 of photoacoustic stimulation when applied to rat dorsal root ganglion explants over time at parameters of 1.7 kHz and 5 ms, with pulse trains are applied every 2 minutes for one hour. FIG. 22 includes traditional and inset images of CNT/Silk light+ with NF, DAPI, and merged perspectives, respectively. FIG. 23 includes traditional and inset images of CNT/Silk light− with NF, DAPI, and merged perspectives, respectively. FIG. 24 includes traditional and inset images of the glass light control group with NF, DAPI, and merged perspectives, respectively, when subjected to light illumination. FIG. 25 includes traditional and inset images of the glass light control group with NF, DAPI, and merged perspectives, respectively, when not subjected to light illumination.

Figure 26:
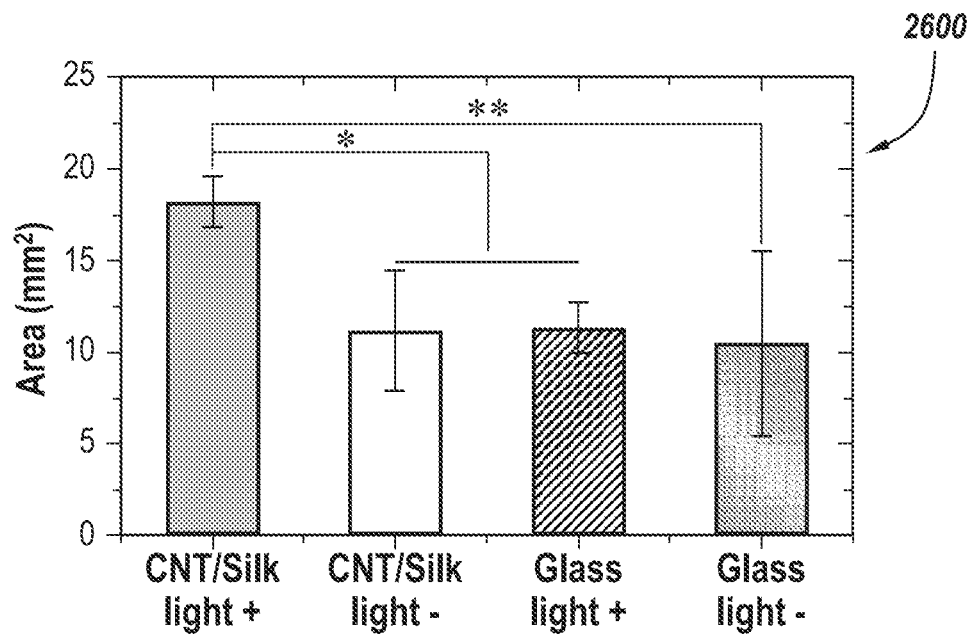
FIG. 26 is a graph of FIGS. 22-25 as a function of area.
Figure 27:
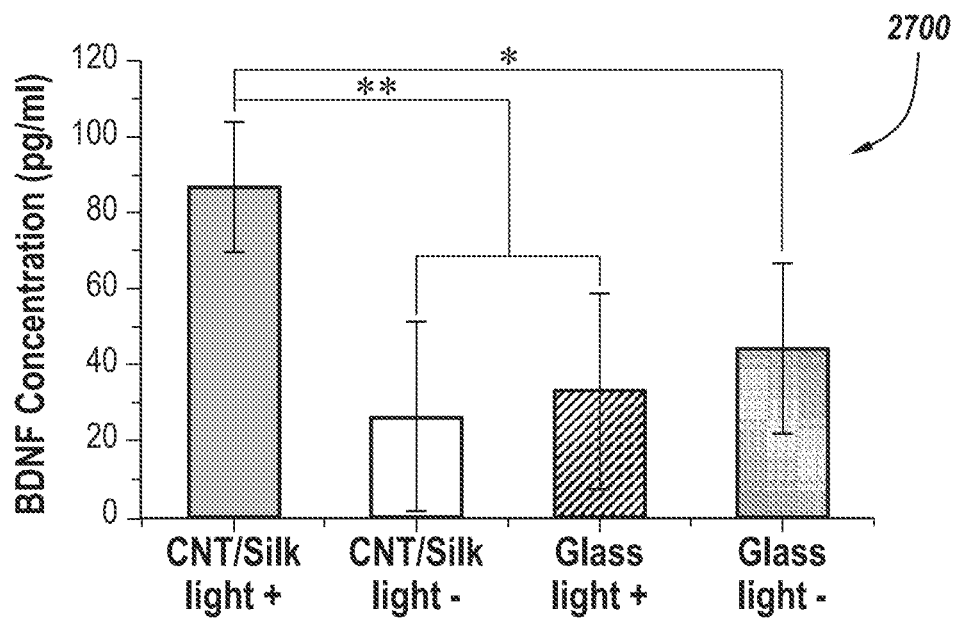
FIG. 27 is a graph of FIGS. 22-25 as a function of BDNF concentration.
Figure 28:
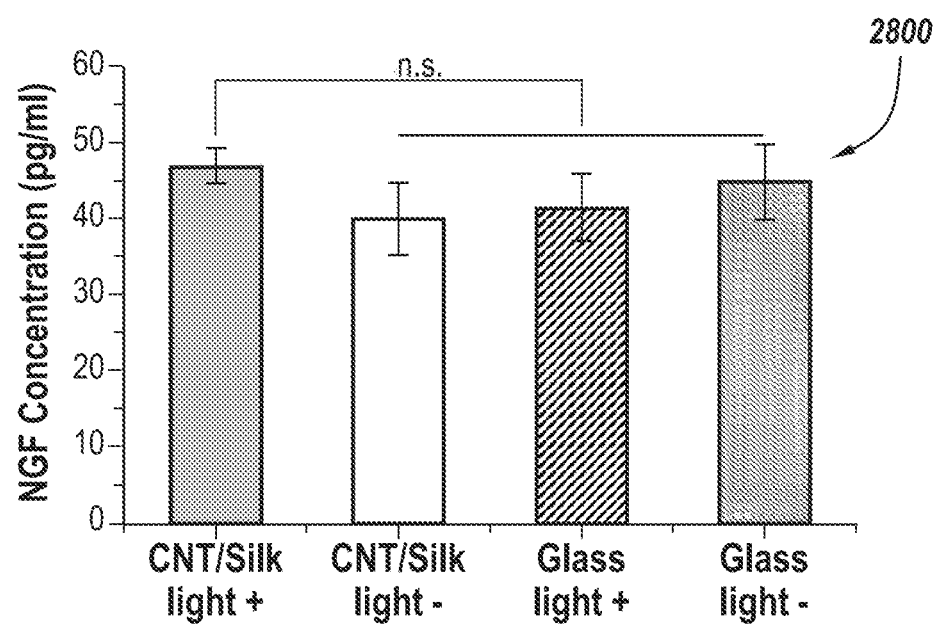
FIG. 28 is a graph of FIGS. 22-25 as a function of NGF Concentration.

Continuing with the illustrative example, FIG. 26 is a graph of FIGS. 22-25 as a function of area. When applied, photoacoustic stimulated DRGs (18.19±1.37 mm2) show a 1.74-fold increase on coverage area compared with a glass control group (10.48±5.067 mm2). Additionally, photoacoustic stimulation can enhance the expression of brain-derived neurotrophic factor (BDNF). As an illustrative embodiment, 24 hours after photoacoustic stimulation, two neurotrophic factors, BDNF and NGF, were measured by ELISA (enzyme-linked immunosorbent assay), as illustrated in FIGS. 27 and 28, respectively. As a result, BDNF concentration of photoacoustic stimulated DRGs (86.52±17.07 pg/ml) exhibited a 1.96-fold increase compared with glass control group (44.20±22.31 pg/ml). No significant difference was observed on the expression level of NGF. In this way, the action potentials and following calcium influx induced by photoacoustic stimulation impacts the BDNF pathway and thus promotes neurite outgrowth.

Figure 29:
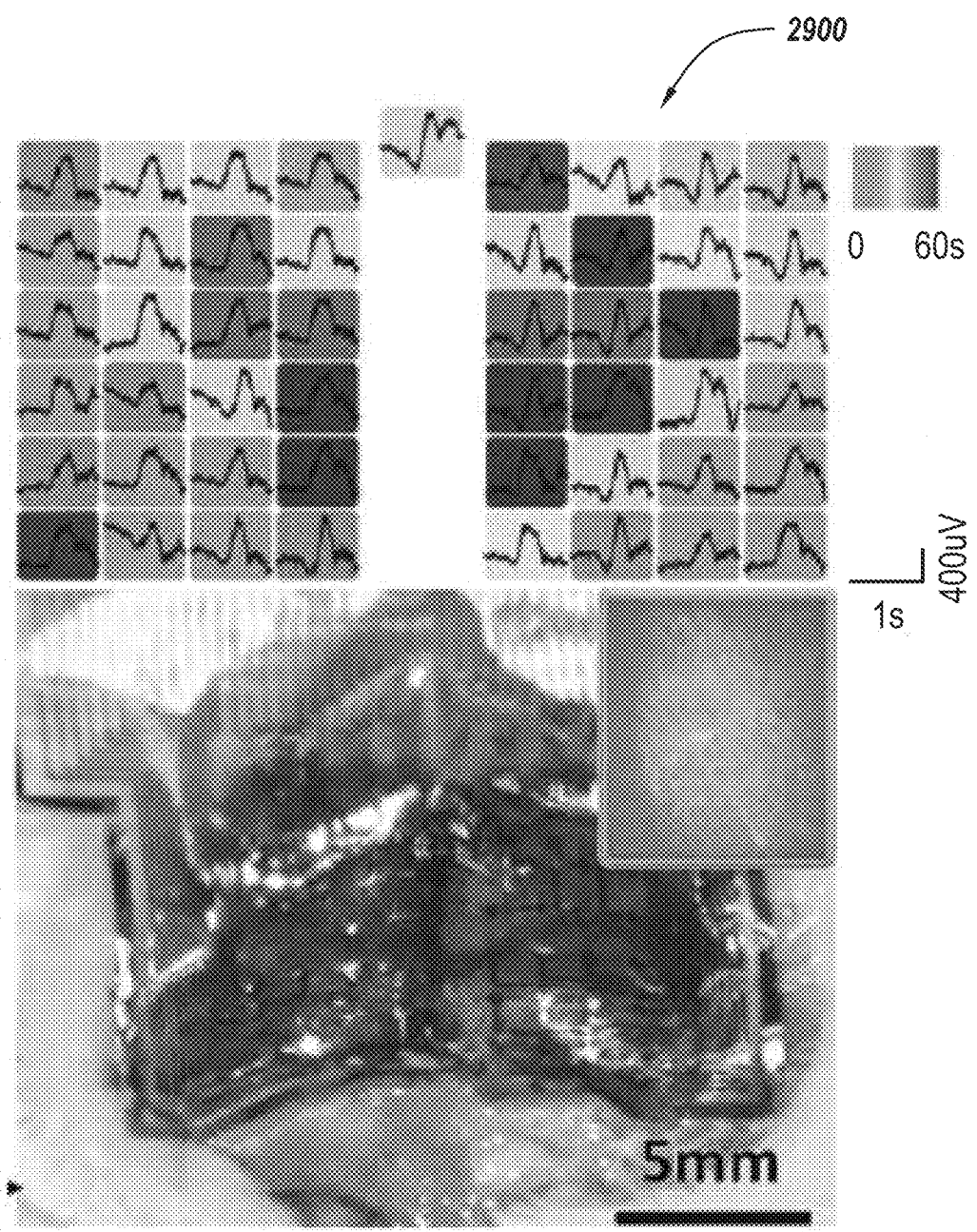
FIG. 29 is an image of a multifunctional neural interface enabling spatiotemporal encoding and decoding when used to treat the brain of a specimen using photoacoustic stimulation from a computer.
Figure 30:
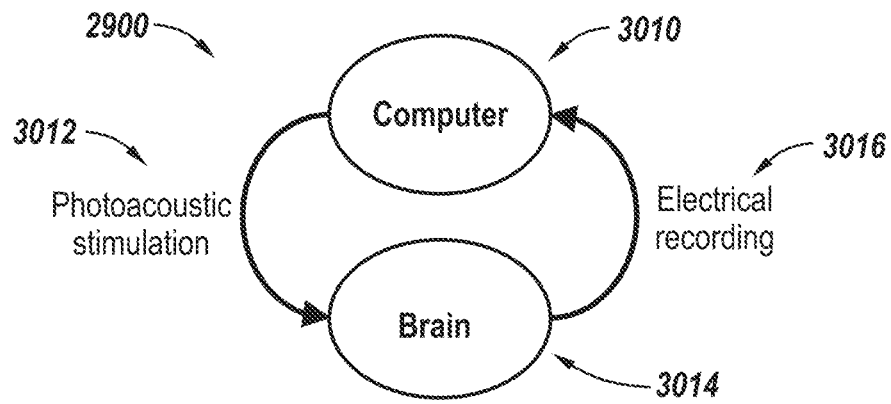
FIG. 30 is an illustration of this dynamic.
Figure 31A:
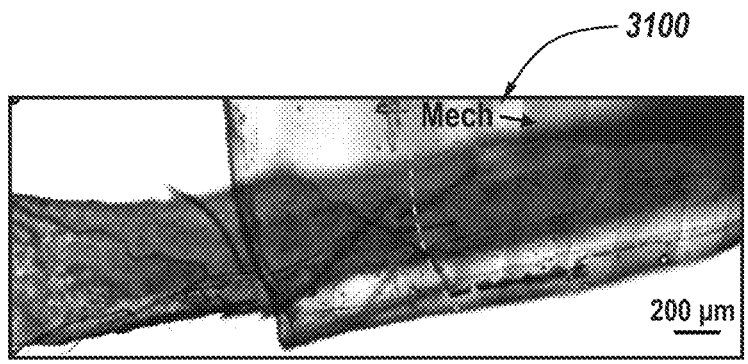
FIGS. 31A and 31B are example images of an implantable cuff for light mediated low invasive PNS stimulation.
Figure 31B:
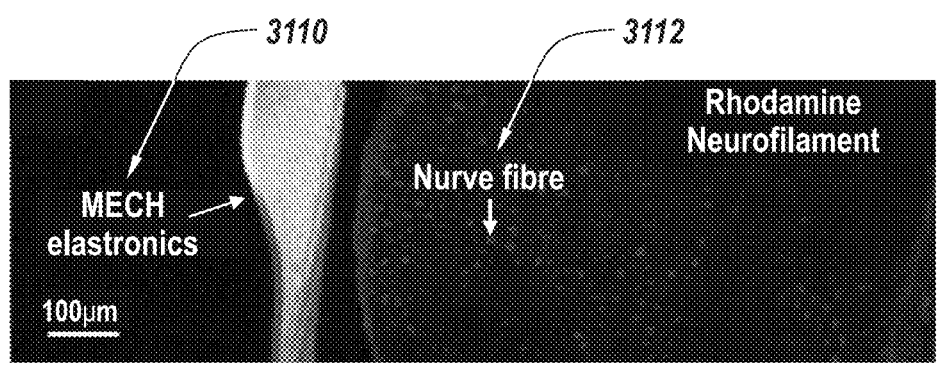
Figure 33:
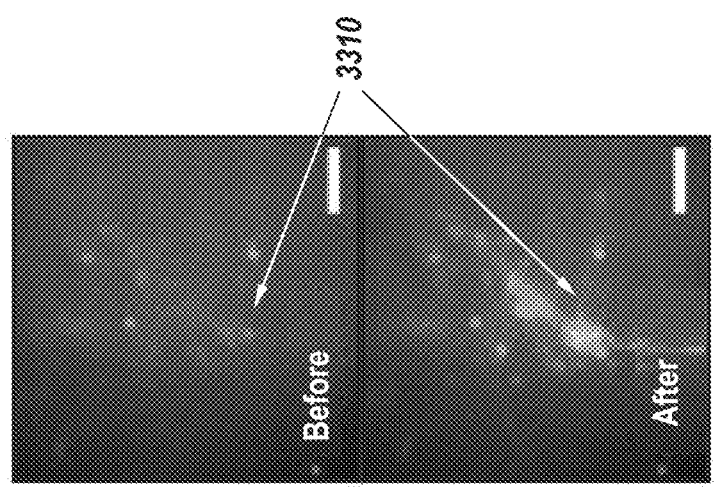
FIG. 33 includes before and after images demonstrating the reliable and repeatable neural stimulation enabled by the photoacoustic process of the present disclosure.
Figure 32:
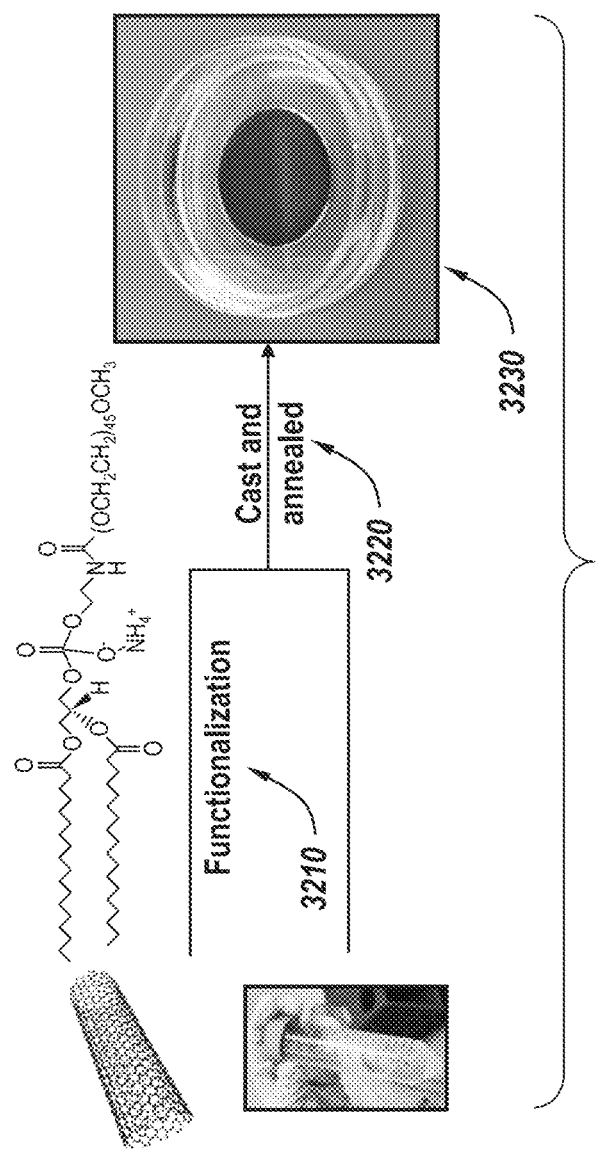
FIG. 32 is a diagram of the hydrogel scaffold integrated with the photoacoustic function through the nanocomposite approach of FIG. 8.

According to the present disclosure, by achieving the high miniaturization levels demonstrated, the tunable optoacoustic emitters can be deployed in minimally invasive medical applications. For example, the aforementioned fiber based optoacoustic devices 100 could be inserted in syringe needles or catheters in close proximity to a focal lesion, thus overcoming the problem of reduced precision and amplitude induced by traditional focused ultrasound. Additionally, it is envisioned that the shape of the TFOE 100 tip can permit focusing frequency waves via a concave structure. FIG. 29 presents one illustrative example, where a multifunctional neural interface enabling spatiotemporal encoding and decoding 2900 is used to treat a subject. This method is further depicted in the FIG. 30 diagram, whereby a computer 3010 provides photoacoustic stimulation 3012 via 2900 to the brain 3014, and subsequently receives electrical recording feedback 3016. Alternatively, FIGS. 31A-31B present an illustrative embodiment where an implantable cuff for light mediated low invasive PNS stimulation 3100 is used to treat a subject at 200 microns and 100 microns, respectively. The MECH elastronics 3110 thereby provide optoacoustic stimulation to nerve fibre 3112. Further, it is envisioned that the methods and devices of the present disclosure can generate stable and reversible sonoporation at each focal target through modification of the ultrasound parameters, enabling precise control for biomedical ultrasound application, which is not available with existing technologies, especially for drug delivery and gene transfer. FIG. 32 provides an overview of the functionalization step 3210, cast and annealing step 3220, and resulting CNT/Silk 3230 product. FIG. 33 provides a before and after image of the excited neurons 3310 due to optoacoustic stimulation. Additionally, it should be noted that the TFOE 100 is immune to electromagnetic interference and hence is compatible with magnetic resonance imaging (MRI).

In the present disclosure, a TFOE is presented that generates acoustic waves with a spatial confinement of ~20 µm, enabling optoacoustic neural modulation with single neuron and subcellular precision. The near field acoustic wave generated by TFOE 100 allows optoacoustic stimulation along with simultaneous monitoring of cell responses using whole cell patch clamp recording, which has been reported to be challenging under conventional ultrasound stimulation. Coupling TFOE 100 with ex vivo brain slice electrophysiology, the present disclosure presents cell-type-specific responses to acoustic stimulation for excitatory and inhibitory neurons.

According the embodiments of the present disclosure, the optoacoustic effect has been extensively used for biomedical imaging, and more recently, it has been explored for neuromodulation 26. Compared to previously reported optoacoustic stimulator, the TFOE 100 offers new capabilities through adapting new device designs and innovative fabrication methods. The highly efficient optoacoustic conversion layer in the TFOE 100 is made of carbon nanotubes of improved solubility embedded in a thermo-expansive PDMS matrix, which significantly improves light to sound conversion efficiency. Additionally, the punch-through coating method ensures uniform coating of the much smaller tapered fiber tip with great control and reliability.

It should be noted that a key advantage of the TFOE 100 is its unprecedented spatial resolution. Transcranial ultrasound neuromodulation has been demonstrated in rodents, non-human primates and in humans. However, due to the wave diffraction limit, focused ultrasound neuromodulation offers a spatial precision of a few millimeters 19, which prohibits site-specific modulation in small animals or single neuron stimulation and therefore lacks the capabilities to study cell-type-specific responses. To overcome this limitation, TFOE 100 generates localized acoustic field at 1 MHz with a spatial resolution of ~20 µm, 1000 times smaller compared to the acoustic wavelength. Utilizing the localized acoustic field, the present disclosure demonstrates neural stimulation with single cell and subcellular precision, and reveals the differential response to TFOE stimulation of subcellular structures by specifically targeting the neuronal soma, dendrites and axons.

By harnessing the controllability of the pulsed laser, the present disclosure identifies the accumulative effect of optoacoustic stimulation at the single cell level, indicating that ultrasonic stimulus can be integrated over a finite duration to become effective. The result from TFOE 100 with the capability of assessing single neuron activity in a network-free condition further ascertains the stimulus accumulation effect as an intrinsic signal interpretation of individual neurons.

More importantly, it is contemplated by the present disclosure that successful TFOE stimulation has been achieved with a single laser pulse of 3 nanoseconds, which generates an acoustic pulse of 1 microsecond. Previously, single tone burst ultrasound with 10 acoustic cycles and overall duration of 22.7 microseconds has been reported as the shortest acoustic stimuli for neuron modulation. Therefore, the present disclosure represents significant improvement of temporal resolution of current acoustic stimulation techniques.

Furthermore, it is contemplated by the present disclosure that TFOE 100 allows integration of acoustic stimulation with whole cell patch clamp recordings. The electrophysiological recordings of TFOE stimulated single neurons in brain slices revealed distinct responses of excitatory pyramidal neurons and inhibitory interneurons to TFOE stimulation. The distinct responses may originate from differences in the intrinsic threshold or variations in the distribution of different ion channels. Moreover, the inhibitory neurons showed elevated threshold of action potential generation compared to excitatory neurons. This contrasts with finding using electric stimulation, where the inhibitory neurons have a lower threshold than pyramidal cells. This discrepancy can be attributed to the different mechanism between acoustic and electric stimulation. Thus, further study, for example, on the ion channel involvement during acoustic stimulation by pharmacologically or genetically modifying ion channels, will provide new insight to the electrophysiological mechanisms of mechanical neuromodulation.

The genetic-free, single-cell stimulation technique provided by the methods of devices of the present disclosure offers new tools to understand the mechanism of neuron stimulation and how individual neurons work together in networks to implement neural computation. Without any metal components, the TFOE 100 is immune to electromagnetic interference and is compatible with magnetic resonance imaging (MRI), which hold promise for future study toward understanding of behavior and disease in human patients.

It should be noted that in addition to the aforementioned applications, neuro-modulation is a valuable platform to understand brain and treat diseases. Precise manipulation of brain activity in behaving subjects is critical to decipher brain and diseases. Optimally, both modulation and reading are non-invasive. As a solution, ultrasound neuro-modulation (USNM) is an emerging non-invasive neural modulation technique, as low frequency ultrasound can non-invasively modulate brain activities. It is contemplated that USNM has higher spatial resolution (<5 mm) compared to TMS and tDCS (~cm). However, lack of guidance hinders accurate ultrasound neuro-modulation. Accurate USNM needs real-time guidance and assessment of brain circuits with sub-mm resolution. It is contemplated that it would be ideal to have ultrasound (US) imaging which is inherently compatible with USNM to provide such guidance.

However, ultrasound is limited in sensing neuro-activities and providing volumetric imaging. For example, Transcranial Doppler ultrasound (tDUS), which monitors blood flow, is limited to use in cognitive science study. US imaging provides only sectional images (B-mode) that is difficult to achieve volumetric monitoring.

Therefore, standardized and volumetric guidance is needed for ultrasound neuro-modulation in researches and clinics. With the aforementioned in mind, fMRI is the most fit candidate to guide and assess USNM. This can be accomplished via functional magnetic resonance imaging (fMRI), which is non-invasive volumetric functional imaging with ~200 µm resolution. Thereby, fMRI is the best candidate to guide USNM (mm level resolution) for non-invasive neuro-modulation.

However, existing MRI-compatible USNM tools are limited and/or inaccessible to researchers. Therefore, advanced engineering is needed to re-design conventional USNM, such as removing all ferrite and metallic components (as most US transducers utilize materials including nickel, ferrite, gold, etc. that interfere with magnetic fields). Additionally, these materials complicate shielding on electronic components to minimize interference. At the present, new MRI-compatible USNM is limited. So far, only 1 system approved in 2016 by FDA for Insightec (Haifa, Israel, founded in 1999). Only 21 systems are installed worldwide, vs. thousands MRI systems currently in use. Further, a compact and portable USNM tool is difficult to create. Similar to DBS (which involves utilizing a lead-fiber to deliver a charge from an implanted pulse generator to an electrode in the brain), USNM needs to be applied chronically to achieve continuous suppression of symptoms. Therefore, compact and portable design USN tools are required. Yet, existing USN tools are rigid and require bulky amplifiers.

Figure 38A:
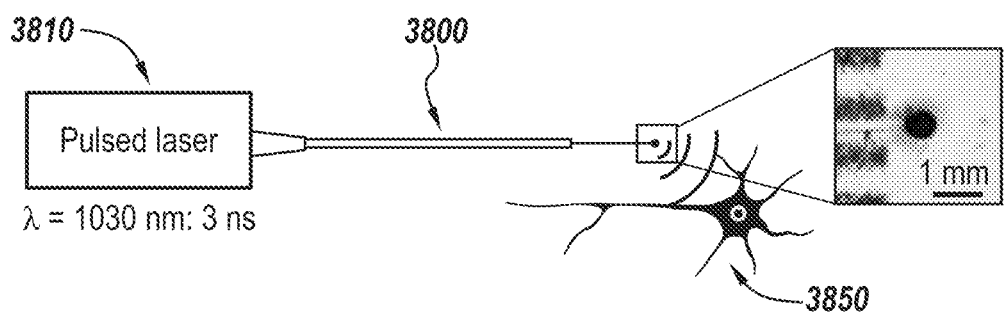
FIG. 38A is a schematic of the Optoacoustic Brain Modulation by Fiberbased Optoacoustic Converter (FOC).
Figure 38B:
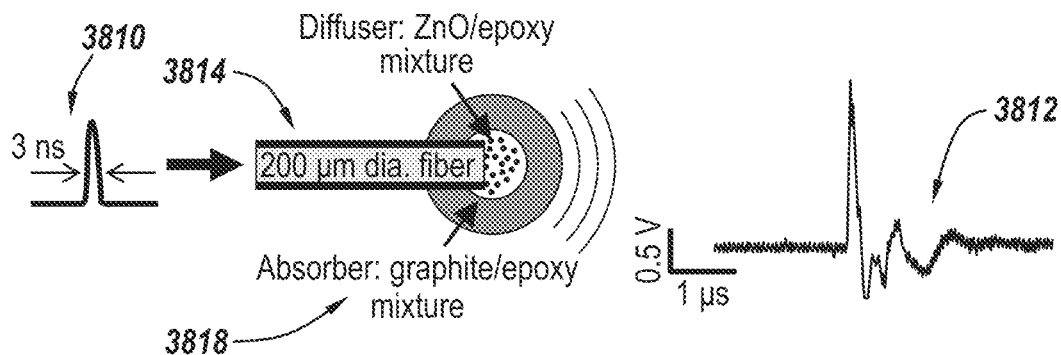
FIG. 38B is a schematic of the FOC as it generates photoacoustic stimulation.

Therefore, there is an unmet need to provide a non-invasive neuro-modulation tool that is non-invasive, MRI-compatible, wearable and widely accessible. According to the embodiments of the present disclosure, an Optoacoustic Brain Modulation by Fiber-based Optoacoustic Converter (FOC) can provide stimulation much like TFOE 100. As an illustrative example, FIG. 38A illustrates a schematic overview of the Optoacoustic Brain Modulation by Fiberbased Optoacoustic Converter (FOC) as pulsed laser 3810 delivers stimulation to neurite tissue 3850 via FOC 3800. FIG. 38B illustrates a schematic overview of the FOC as it generates photoacoustic stimulation, generating optoacoustic signal 3812 via FOC 3800. To do so, pulsed laser 3810 is delivered via 200 micron fiber 3814, which thereby engages ZnO/epoxy mixture diffusion layer 3816 and graphite/epoxy mixture absorption/expansion layer 3818 to generate signal

Figure 39A:
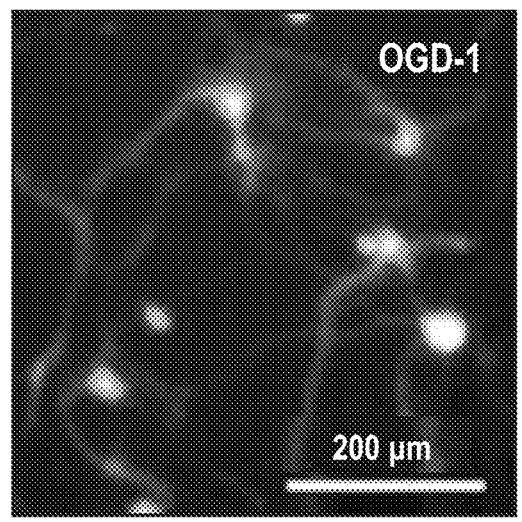
FIGS. 39A-39C provide an image and graphs of the FOC inducing calcium transients in cultured primary neurons.
Figure 39B:
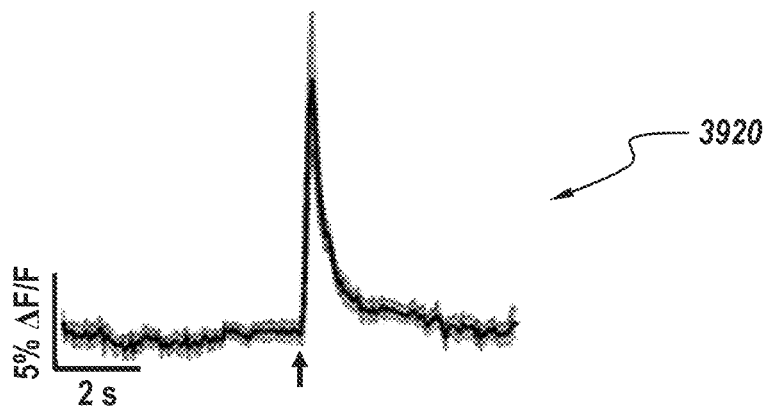
Figure 39C:
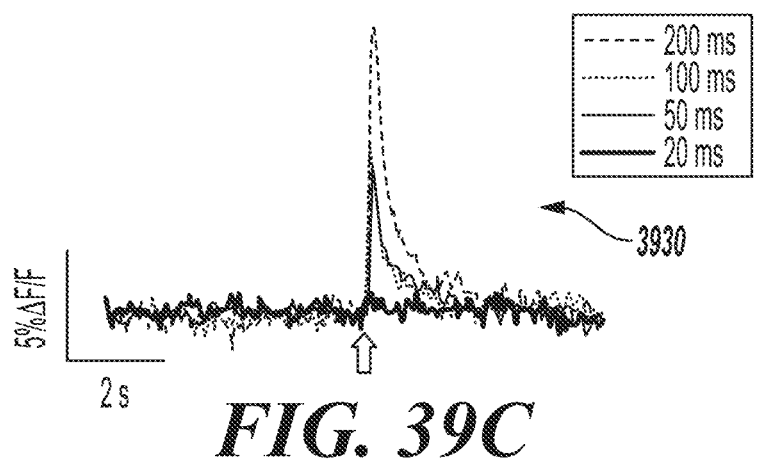
Figure 40A:
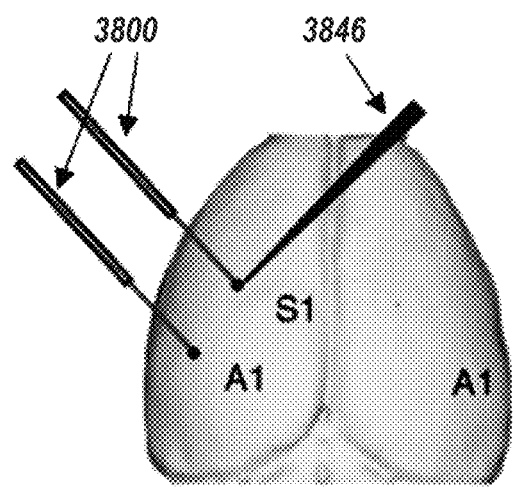
FIGS. 40A-40B are a schematic and graph of the FOC inducing neural activation in vivo in the mouse brain, respectively.
Figure 40B:
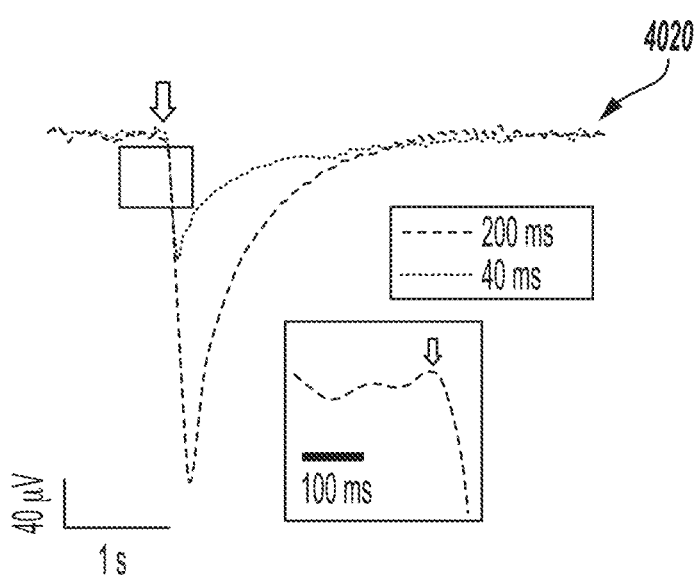

3812, much like TFOE 100. To illustrate this, FIGS. 39A-C provide images and graphical depictions of the FOC 3800 inducing calcium transients in cultured primary neurons, with primary neurons stained. Further, FIGS. 40A-B provide images and graphical depictions of the FOC 3800 inducing neural activation in vivo in the mouse brain, involving cutting tool 3846 and FOC 3800. However, FOC 3800, due to its invasive and thereby surgical nature, is not always optimal.

Figure 41:
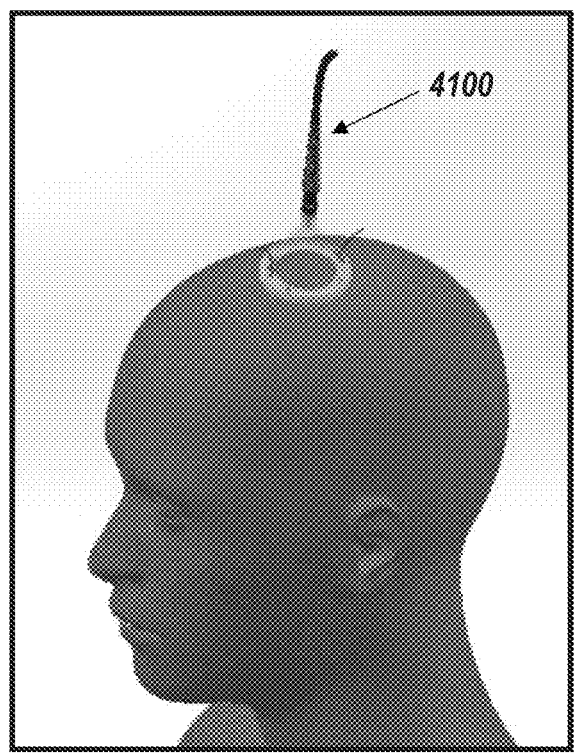
FIG. 41 is a rendering of the Non-invasive Neural Modulation System using AMRI-compatible Soft Optoacoustic Pad (SOAP) as a treatment.
Figure 42:
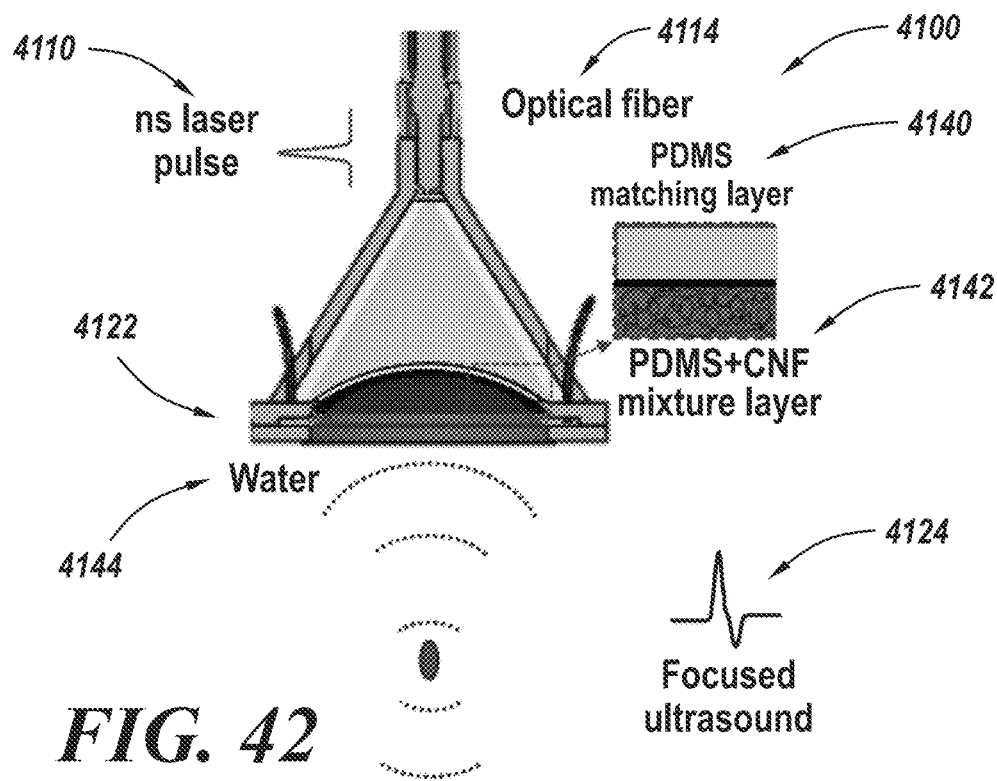
FIG. 42 is a schematic of how the SOAP provides focused ultrasound to a treatment location.
Figure 43:
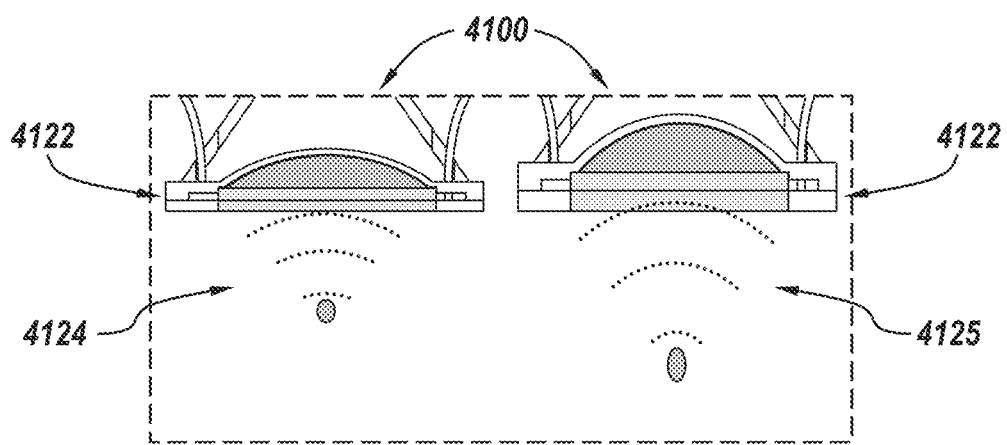
FIG. 43 is a schematic of how the SOAP provides adaptive focus tuning.

According to the present disclosure, a Non-invasive Neural Modulation System using AMRI-compatible Soft Optoacoustic Pad (SOAP) solves this issue. FIG. 41 provides an illustrative overview of the Non-invasive Neural Modulation System using AMRI-compatible Soft Optoacoustic Pad (SOAP) as a treatment. The SOAP 4100 delivers focused ultrasound treatment to neurite tissue utilizing water 4144, a PDMS matching layer 4140, and a PDMS+CNF mixture layer 4142. FIG. 42 provides an illustrative schematic of how the SOAP 4100 provides this focused ultrasound 4124 to a treatment location, similarly enabled by laser pulse 4110 and optical fiber 4114. Focused ultrasound 4124 can further be adjusted by changing water volume inside SOAP 4100; FIG. 43 provides an illustrative schematic of how the SOAP 4100 can thereby provide adaptive focus tuning by comparing wavelengths of differing ultrasounds 4124 and 4125 respectively.

Figure 44A:
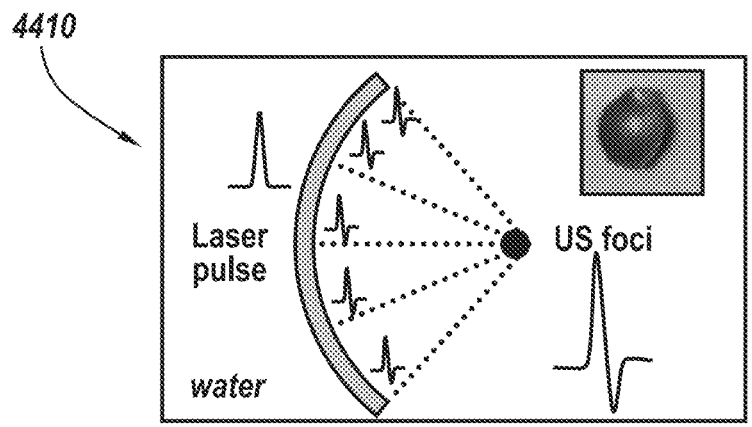
FIGS. 44A-44C are images depicting illustrative embodiments relating to the generation of focused ultrasound by a curved optoacoustic film that represents a static engineered phase profile in optoacoustic emission.
Figure 44B:
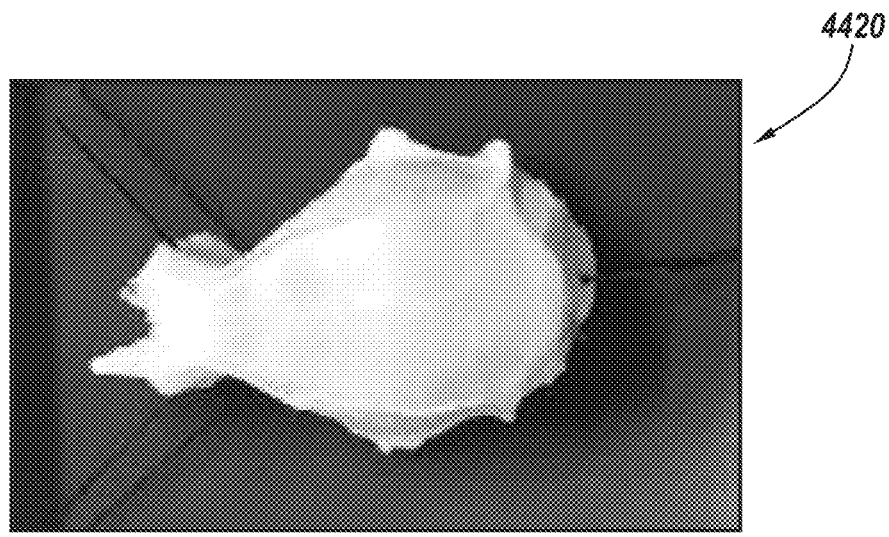
Figure 44C:
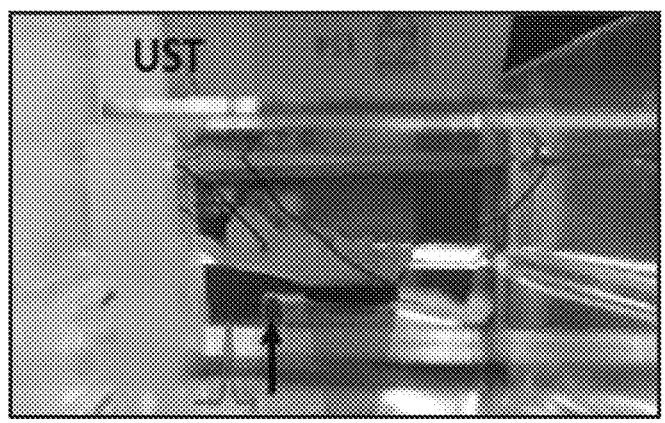
Figure 44D:
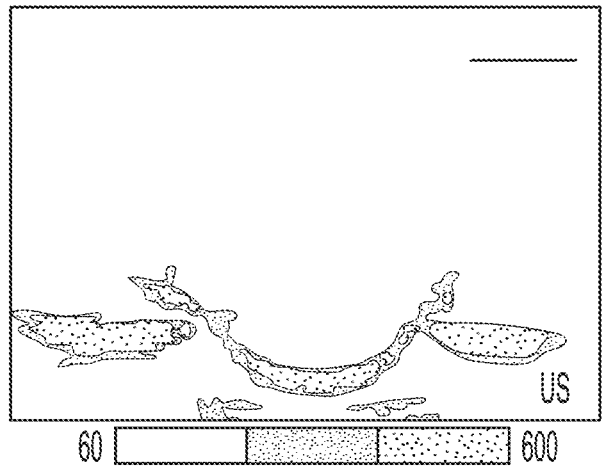
FIGS. 44D-44F are generated ultrasound images illustrating focused ultrasound applied without the rat skull present, and 44G-44I are images illustrating with the rat skull present.
Figure 44E:
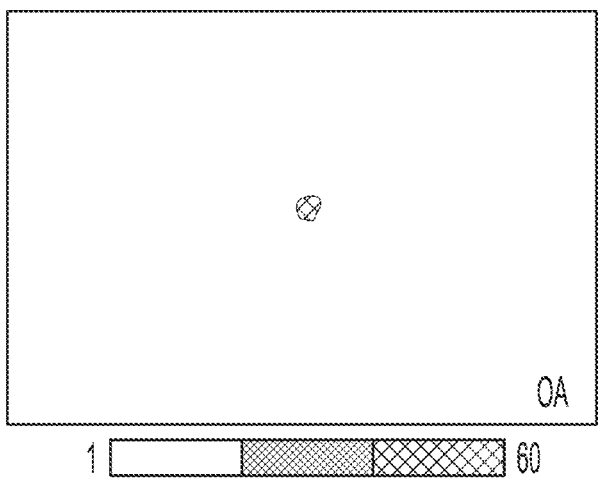
Figure 44F:
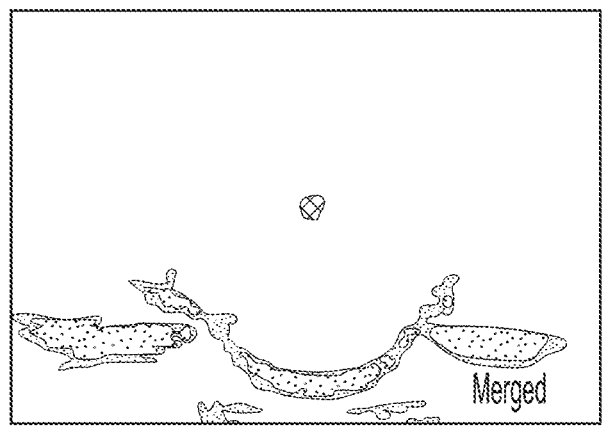
Figure 44G:
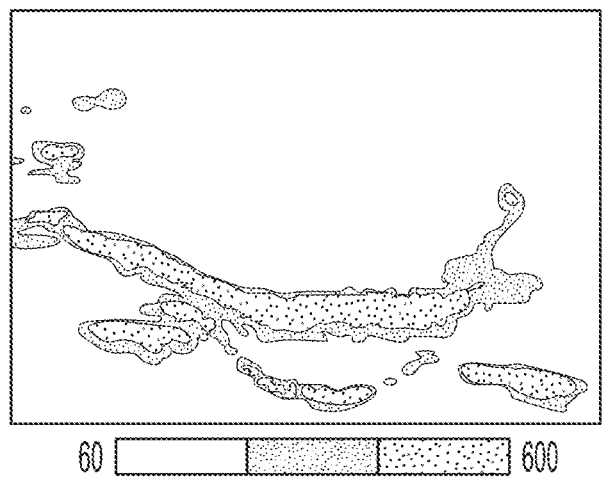
Figure 44H:
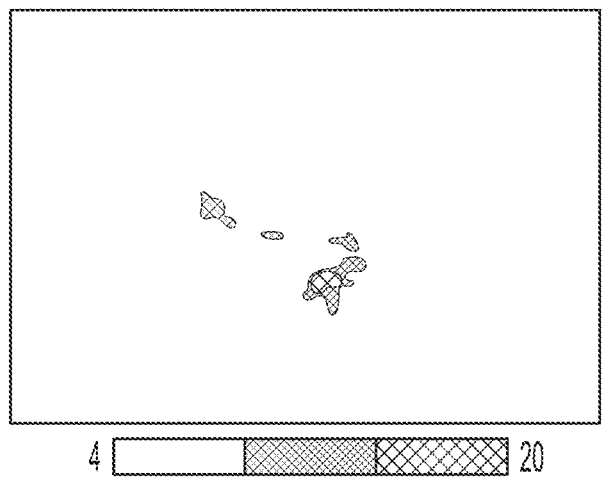

According the exemplary embodiments herein, this treatment is applied in FIGS. 44A-I. FIGS. 44A-C provide images depicting illustrative embodiments relating to the generation of focused ultrasound by a curved optoacoustic film that represents a static engineered phase profile in optoacoustic emission. FIGS. 44D-F provide the generated ultrasound images illustrating without the rat skull present (scale bar: 5 mm. US: ultrasound (44D), OA: optoacoustic (44E)), and merged ultrasound and optoacoustic (44F), and 44G-I provide images illustrating with the rat skull present (scale bar: 5 mm. US: ultrasound (44G), OA: optoacoustic (44H)), and merged ultrasound and optoacoustic (44I).

According the exemplary embodiments herein, the design and fabrication of SOAP 4100 (with, for example, 4 MPa at focus (no bone) with <0.65 MHz ultrasonic emission) is contemplated. It is further contemplated that transcranial US transmission needs <0.65 MHz ultrasound. 1 MPa at focus has been shown to be sufficient to induce human brain response without damage. Additionally, 4-fold attenuation in pressure level by human skull is expected. FIG. 45 provides a schematic illustration of the setup dynamic for the SOAP 4100 system. Laser pulse 4112, by way of FG1 and FG2 respectively, delivers said pulse 4112 via optical fiber 4114 to air 4126 over the SOAP 4100 treatment area. The SOAP is comprised of adjustable water 4144, a PDMS matching layer 4140, and a PDMS+CNF mixture layer 4142.

Figure 47:
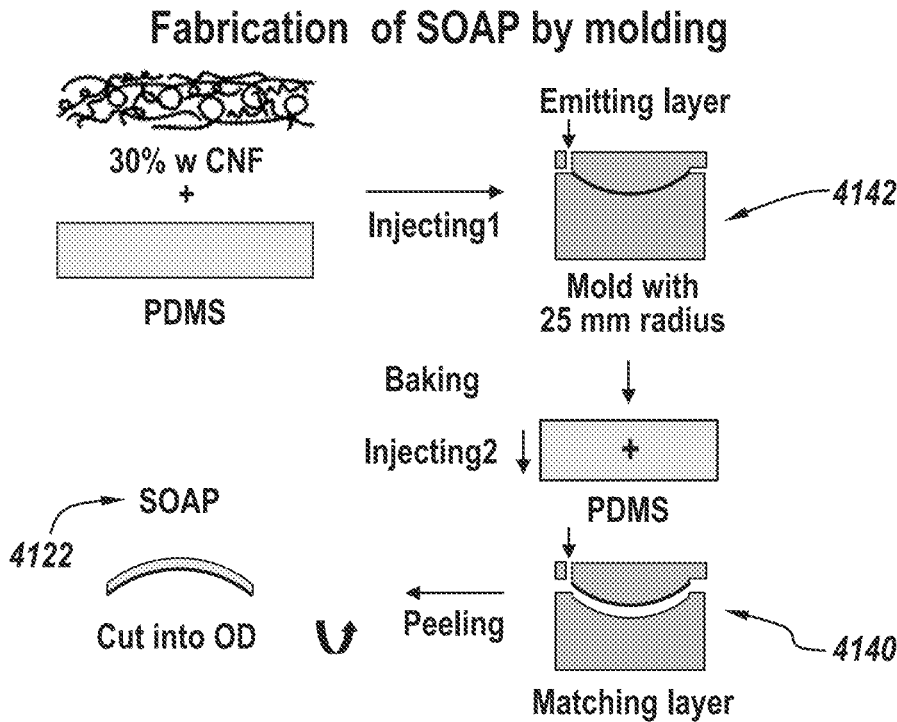
FIG. 47 is a schematic of the fabrication process of the SOAP via molding.

Continuing with the illustrative embodiment, fabrication of the SOAP pad 4122, which can be inserted into SOAP 4100, by way of molding is instructed via FIG. 47, which provides a schematic illustration of the fabrication process of the SOAP pad 4122. A solution of 30% CNF is injected into a mold with a 25 mm radius. The solution is baked in the mold to form, and PDMS is added, to form emitting PDMS+CNF mixture layer 4142. The resulting product, 4142, is injected with additional PDMS, and peeled with the PDMS matching layer 4140, cut into OD, and forms the SOAP pad 4122 comprising PDMS matching layer 4140 and PDMS+CNF mixture layer 4142. SOAP 4122 can be further scaled and adjusted for different subjects per FIG. 46, which provides a tabular overview of the envisioned human and mouse subject diameter and focal length parameters (human: 30 mm diameter, 25 mm focal length; mouse: 5 mm diameter, 3 mm focal length). It is envisioned that the SOAP 4100 is soft-polymer based.

Figure 48:
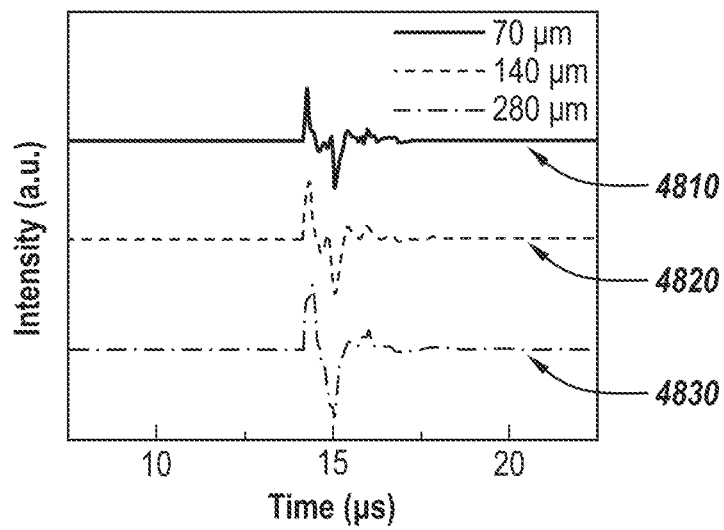
FIG. 48 is a graph of simulation data relating to ultrasound wave form with different thicknesses.
Figure 49:
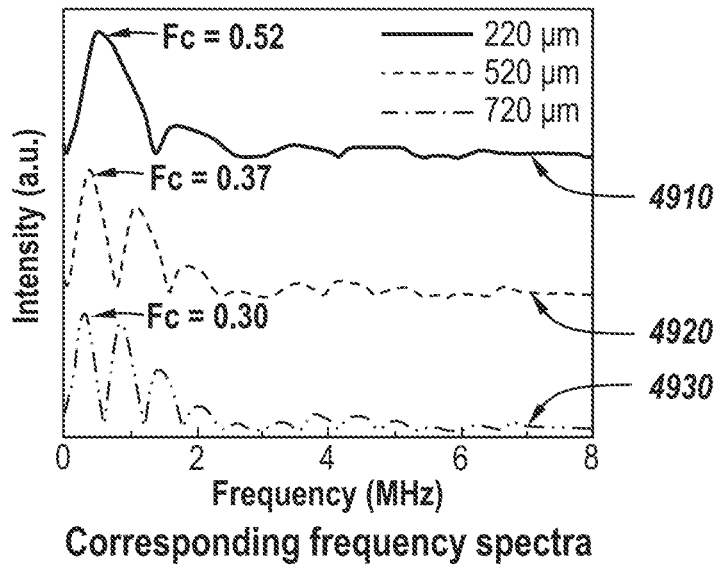
FIG. 49 is a graph of simulation data relating to corresponding frequency spectra.
Figure 50:
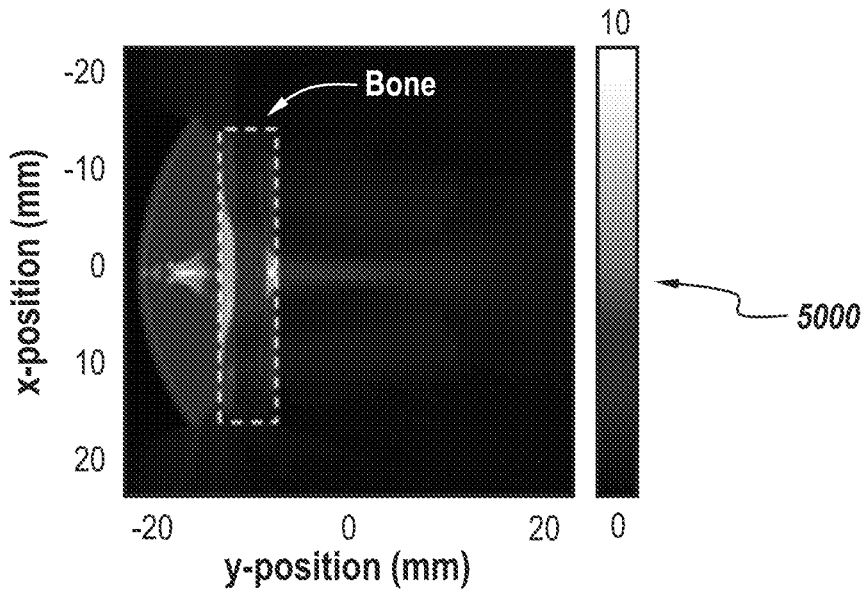
FIG. 50 is an image of simulation data relating to a focus inside with human skull bone thickness of 6 mm, with a lateral FWHM of 4.6 mm.

According to the embodiments herein, desired intensity of optoacoustic stimulation should vary depending on the diameter and focal lengths of the mold. FIG. 48 provides a graphical depiction of simulation data relating to ultrasound wave form with different thicknesses. FIG. 49 provides a graphical depiction of simulation data relating to corresponding frequency spectra. FIG. 50 provides an image of simulation data relating to a focus inside with human skull bone thickness of 6 mm, with a lateral FWHM of 4.6 mm.

Figure 51:
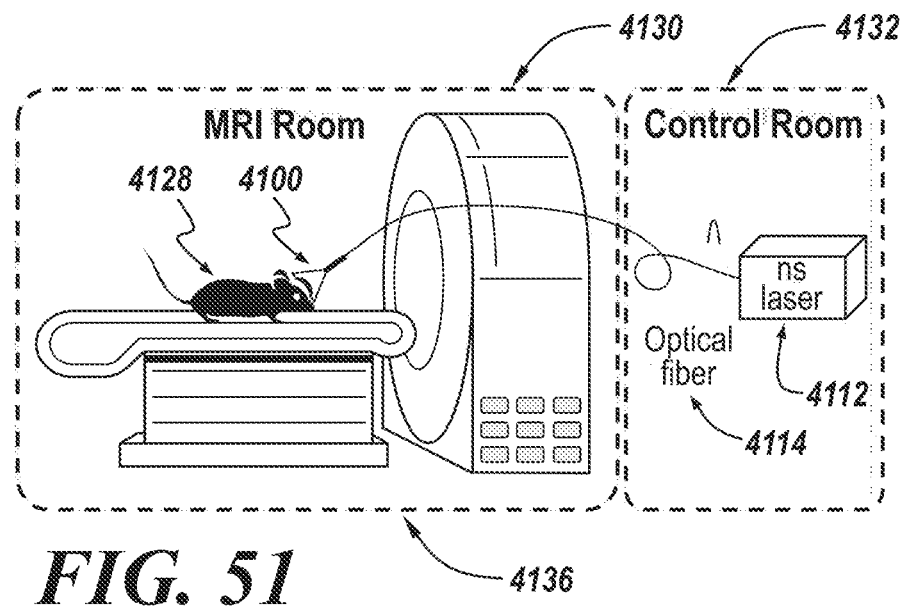
FIG. 51 is a diagram of a restrained mouse subject undergoing neural modulation ex vivo.

Thereby, the SOAP 4100 can be utilized ex vivo on a mouse brain slice. According to an illustrative embodiment, adult C57BL/6J mice (age 14-16 weeks) can be utilized as specimens, focusing on 12 contiguous coronal image slices of 0.5 mm thickness with the first slice placed 2 mm rostral of bregma according to a stereotaxic mouse brain atlas. FIG. 51 illustrates a diagram of the restrained mouse subject 4128 undergoing neural modulation ex vivo in MRI Room 4136 via laser pulse 4112, optical fiber 4114, and MRI unit 4130 respectively. For parameters, BOLD-fMRI imaging using a gradient-echo echoplanar imaging (GE-EPI) sequence (TR/TE=1,000/12 ms, flip angle 60°, matrix 80×35, 1 average) with a temporal resolution of 1 s is envisioned. Further, it is envisioned that 200 ms SOAP modulation at 1 kHz laser repetition rate will be conducted on each mouse used.

Figure 52:
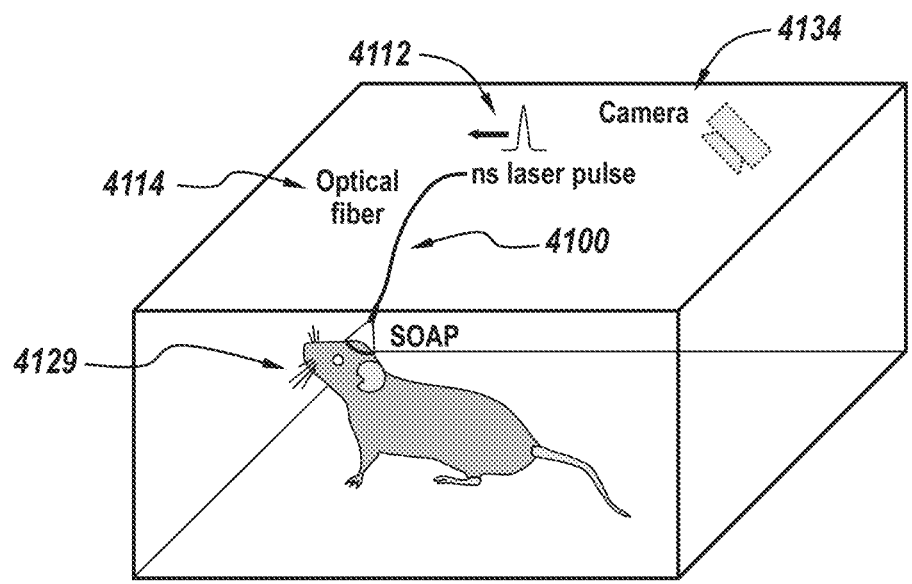
FIG. 52 is a diagram of a free-moving mouse subject undergoing non-invasive in vivo neural modulation.

Additionally, SOAP 4100 can be applied non-invasively in vivo by way of neural modulation in a free-moving mouse subject. FIG. 52 illustrates a diagram of a free-moving mouse subject 4129 undergoing non-invasive in vivo neural modulation. It is contemplated that the SOAP 4100 is lightweight and compact enough to be wearable for free-moving mouse experiments. It is envisioned that the SOAP 4100 will target primary and secondary motor cortex in the left mouse hemisphere by way of laser pulse 4112, optical fiber 4114, and SOAP 4100. Movement pattern is expected to change when SOAP 4100 is on, when compared to the control group (e.g. clockwise movement when SOAP 4100 is on), which can be monitored by camera 4134.

Figure 53:
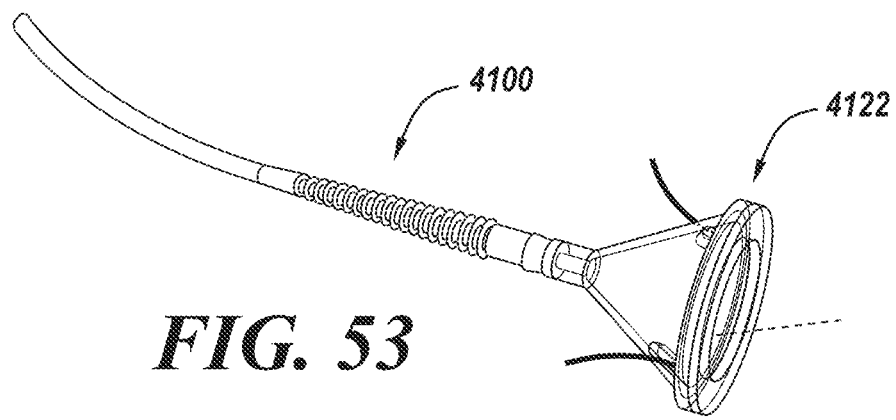
FIG. 53 is a schematic of the SOAP device.

FIG. 53 provides a schematic overview summarizing the SOAP 4100 device. The SOAP 4100 is an optical powered & polymer-based ultrasound emitter which is MRI compatible, and is the first-time non-invasive optoacoustic in vivo brain modulation. Additionally, SOAP 4100 permits low frequency ultrasound generation, which is distinct from conventional optoacoustic emitters (in the ~tens of MHz). The SOAP 4100 has tunable capability and applicability in focused ultrasound generation via adjustable water volume and molding respectively. In this way, SOAP 4100 can enable real-time MRI guided BBB opening with MRI-compatible focused ultrasound. Further, SOAP 4100 can be flexible and designed to tune the acoustic focus with actuators, such as pneumatic pump.

According to another aspect of the present disclosure, the usage of neuromodulation as a powerful tool to decipher neurocircuits and treat neurological diseases is further detailed. Transcranial focused ultrasound (tFUS) provides a millimeter-scale spatial resolution due to sub-MHz frequency. However, targeting brain sub-regions in small animals desires submillimeter precision. The present disclosure includes an optically-driven focused ultrasound (OFUS) generated by a soft optoacoustic pad (SOAP) fabricated by embedding candle soot nanoparticles in a polydimethylsiloxane spherical surface. SOAP can generate an ultrasound focus at 15 MHz with a lateral resolution of 66 µm, which is two order of magnitude smaller than that of tFUS. The present disclosure demonstrates that OFUS achieves neurostimulation in vitro with a sub-microsecond single cycle and 0.06 µJ/cm2, two orders of magnitude less ultrasound energy compared to tFUS successfully used for neural stimulation. Additionally, the present disclosure demonstrates submillimeter transcranial stimulation in the mouse motor cortex in vivo. By delivering a submillimeter precision non-invasively, OFUS opens a new way for neuroscience studies and neurological disease treatments by way of an optically-driven focused ultrasound for non-invasive neuromodulation with submillimeter precision in vivo.

According to the exemplary embodiments herein, to understand how brain functions control behaviors and its dysfunction causes diseases, a modality to modulate neuronal activity with high precision is needed. In small animals, a neuromodulation tool with sub-millimeter precision can map the brain sub-regions by modulate a small population of neurons. Invasive methods, such as electrical stimulation and optogenetics, can provide a spatial resolution at submillimeter scale. Electrical stimulation tools have already been a gold standard in neuromodulation studies and disease treatment. For example, deep brain stimulation achieves effective treatment for several diseases by implanted electrodes. It has been approved for clinical treatment of Parkinson's disease, depression, and epilepsy. However, the current spread limits the precise control of targeting. Optogenetics provides an unrivaled sub-cellular spatial resolution and specificity in targeted cell types by using light to trigger transfected neurons, which has advanced the studies of neuroscience. Transcranial optogenetics in mice can further avoid surgery and successfully stimulate a brain area ~0.8 to 1 mm laterally at a penetration depth of 5~6 mm. However, transcranial optogenetics has a light transmission rate ~0.02% at 7 mm. Both conventional and transcranial optogenetics rely on viral transfection which has yet to be approved for use in human brains. Non-invasive methods offer effective neuromodulation while avoiding the risk of surgery. Transcranial direct current stimulation (tDCS) and transcranial magnetic stimulation (TMS) are non-invasive, but provide a spatial resolution of centimeter-level due to the long wavelength of electromagnetic waves used. The emerging transcranial focused ultrasound (tFUS) has been demonstrated as a non-invasive neuromodulation method with high precision in various models, such as mice, rats, rabbits, monkeys, and even in humans. Both pulsed and continuous sonication schemes has been employed, while pulsed sonication is more popular due to lower stimulation threshold to elicit neural responses. A low intensity within 100 W/cm2 has been used to minimize possibility of tissue damage. To achieve high transcranial efficiency, tFUS with a low ultrasonic frequency of ~1 MHz or less is preferred, which limits its spatial resolution to several millimeters. For humans, this spatial resolution can achieve stimulation volumes corresponding to individual nuclei in thalamus. To target brain sub-regions in small animals at a scale of a few hundred microns, a non-invasive neuromodulation tool with submillimeter precision is needed.

It should be noted that the optoacoustic effect is an alternative way to generate ultrasound. Optoacoustic materials absorb a short pulse of light and convert it into a transient temperature increase and thermal expansion, resulting in the generation of an ultrasound pulse. Recent work has demonstrated this by way of a fiber-based optoacoustic emitter (FOE) for high spatial resolution neurostimulation. In these fiber based optoacoustic emitters, as detailed earlier by way of TFOE 100, the optoacoustic material can be coated on the tip of an optical fiber and the coated fiber acts as a highly localized point source of ultrasound, providing a resolution from submillimeter to a few tens microns enabling selectively activating subcellular structures. However, since it exploits near-field ultrasound for localized neuromodulation, fiber based optoacoustic emitters need to be surgically implanted to the neural tissues and cannot be applied transcranially.

According to the exemplary embodiments of the present disclosure, an optically-driven focused ultrasound (OFUS) 5400 for non-invasive neuromodulation with submillimeter precision is presented. In addition to previously presented SOAP 4100, the film can be curved so that it will generate a focused ultrasound for non-invasive modulation. Curved SOAP 5410 based on polydimethylsiloxane (PDMS) and a carbon-based absorber can be fabricated, and enable tighter spatial focusing and maximization of the focal pressure; accordingly, the diameter of the curvature can be tailored to reach a numerical aperture (NA=0.95) close to the theoretical limit (NA=1). To efficiently convert photons to acoustic wave by the optoacoustic effect, SOAP 5400 can include designed curvatures based on four different optoacoustic materials, including heat shrink membrane (HSM), carbon nanotube mixed with polydimethylsiloxane (CNT-PDMS), carbon nanoparticle mixed with PDMS (CNP-PDMS), and candle soot layered with PDMS (CS-PDMS), can also be fabricated and tested. Their optoacoustic conversion efficiencies can thereby be compared by measuring the pressure at the foci of these OFUS fabricated. With CS-PDMS OFUS 5400, the present disclosure generates ~48 MPa at ultrasound focus with 0.62 mJ/cm2 laser input. Additionally, CS-PDMS OFUS having a ~66 µm spatial resolution with transcranial ability is further demonstrated, and achieves two orders of magnitude improvement from the a few millimeter resolution offered by tFUS. By calcium imaging, the present disclosure achieves direct and transcranial single-pulse stimulation with SOAP 5410 reliably and safely in cultured neurons in vitro. The total ultrasound energy input of SOAP 5410 is two orders of magnitude less than that delivered with conventional ultrasound transducer to evoke similar level of neuron responses. With immunofluorescence imaging, the present disclosure includes visualizing a stimulation volume of submillimeter in mouse brain. Additionally, the present disclosure involves validating functional outcomes by stimulating the motor cortex non-invasively in mice with SOAP 5410 in vivo using the electrophysiological recording.

Figure 54A:
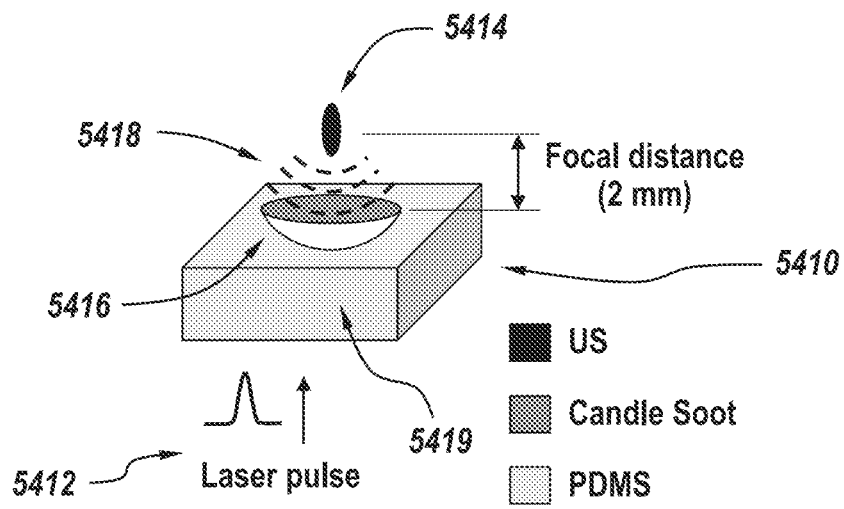
FIGS. 54A-H further detail the design, fabrication, and characterization of SOAP.
Figure 54B:
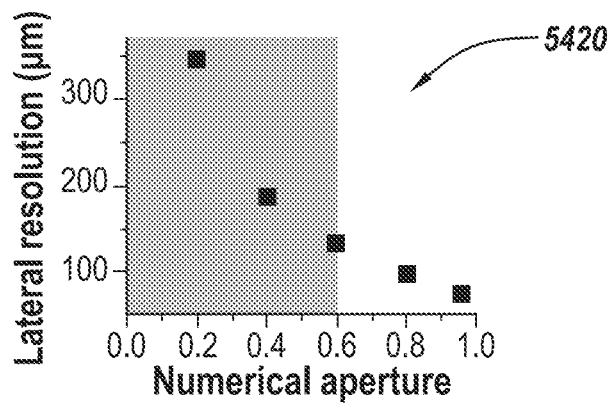

The present disclosure further details the fabrication of SOAP 5410 and optimization of optoacoustic efficiency. To generate a focused ultrasound field with submillimeter precision, numerical simulations to predict generated acoustic fields and optimize the geometric design of SOAP 5410 are presented. FIG. 54A shows the schematic illustration of SOAP 5410. A nanosecond laser 5412 is delivered from the bottom of SOAP 5410. Through the optoacoustic effect, ultrasound waves 5414 are generated at the surface of the curved SOAP 5410, then the waves 5414 emitted from different angles on the curvature will arrive at its geometric center 5416 in-phase. The geometric center 5416 includes candle soot 5418, and is disposed on PDMS layer 5419. A focal distance of 2 mm is designed to ensure the ultrasound can penetrate the skull and reach the cortical layer in a mouse brain for stimulation. Numerical simulations using k-wave toolbox in MATLAB can be performed to calculate the generated acoustic field. SOAP 5410-generated OFUS 5400 propagates into the water with air-backing to mimic the application scenarios. Accordingly, the central frequency of 15 MHz and bandwidth of 200% can be set according to reported data of carbon-based absorbers. The focal distance and tuned radius and curvature diameters are thereby fixed to provide submillimeter precision. The ratio of the curvature diameter to radius is therefore proportional to numerical aperture (NA). The lateral resolution is defined as the full width at half maximum of the lateral profile. The relationship of the lateral resolution to NA is plotted in FIG. 54B. The higher NA is, the more precise the lateral resolution is. In FIG. 54B, area 5420 indicates the range of NA in conventional ultrasound transducers. In the fabrication process of a conventional single-element focused ultrasound transducer, it is difficult to reach high NA due to the cracking in the single crystal piezoelectric material. However, a high NA close to the theoretical limit is feasible with optoacoustic material, as it provides a half of the best lateral resolution that a conventional transducer can provide at the same ultrasonic frequency.

Figure 54C:
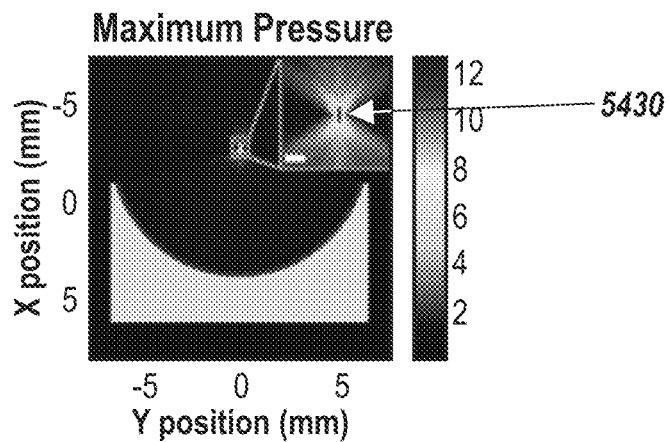

To push the lateral resolution to the limit at 15 MHz, a high NA for SOAP of 0.95, which is close to the theoretical limit, can be selected. The radius of SOAP 5410 is thereby optimized to 6.35 mm, and the diameter of curvature set to 12.2 mm. This geometry provided an OFUS 5400 at the center of the curvature as expected, as detailed in FIG. 54C, which is an image 5430 of the acoustic field generated by SOAP 5410 in k-wave simulation with designed geometry. The inset is zoom in at acoustic focus, with a scale bar of 200 μm. The generated OFUS has a lateral resolution at −6 dB of 78 μm, and an axial resolution of 209 μm. This spatial resolution is sufficient for our submillimeter precision neurostimulation in small animals.

Continuing with the illustrative embodiment, the present disclosure provides that such a high NA provides OFUS 5400 not only with a high lateral resolution but also a high focal gain at the focus point. By adapting the concept of the lateral resolution for acoustic-resolution photoacoustic microscopy, the lateral resolution of OFUS 5400 can be calculated by the following equation.

$$R_L = 0.71 \frac{v}{NA \cdot f} \quad (1)$$

Here, v is the ambient sound speed, f is the central frequency. By this equation, the theoretical lateral resolution of OFUS R_L=75 μm, which is consistent with the simulation results. Moreover, a spherical surface with high NA provides a low f-number and high focal gain G, which is defined by the ratio of the pressure at the focal point to the pressure on the spherical surface according to the following equation.

$$G = \frac{2\pi f}{c_0} r \left(1 - \sqrt{1 - \frac{1}{4f_N^2}}\right) \quad (2)$$

In this equation, f, $c_0$, r, and $f_N$ stands for the acoustic frequency, the speed of sound in the medium, the radius of curvature, and f-number which is the ratio of the radius of curvature to the diameter of the SOAP 5410. By taking the water attenuation coefficient $2.2 \times 10^{-3}$ dB/(cm×MHz$^2$) into consideration, the effective focal gain $G_{eff}$≈280 for SOAP 5410 can be estimated. This focal gain is 5 to 92 fold higher compared to the focal gain of the conventional ultrasound transducer with $f_N$=1 to 4 [1, 37-41]. By pushing the NA to the limit, the precision of lateral resolution can be maximized at 15 MHz, as well as improve the pressure at the focal point by orders of magnitude compared to a conventional focused ultrasound transducer.

Figure 54D:
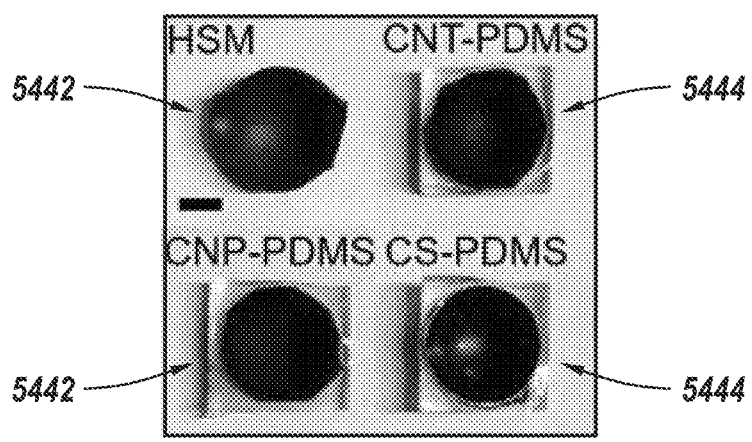

According to the exemplary embodiments herein, to optimize the optoacoustic conversion efficiency, the preparation of the four materials to fabricate SOAP according to described geometric design, including HSM 5442, CNT-PDMS 5444, CNP-PDMS 5446, and CS-PDMS 5448, is detailed in FIG. 54D. From left to right, top to bottom: heat shrink membrane 5442, carbon nanotube-PDMS 5444, carbon nanoparticles-PDMS 5446, and candle soot-PDMS 5448 are presented, with scale bar: 5 mm. For HSM 5442, the elastic black polyolefin itself serves as light-absorber and expansion material simultaneously. For the rest three designs CNT-PDMS 5444, CNP-PDMS 5446, and CS-PDMS 5448, the carbon-based materials, as light-absorber materials, are embedded into PDMS, which serve as the expansion material. They form a mixture at the curvature surface to maximize optoacoustic conversion. The method for fabricating CS-PDMS 5448 is also provided by the present disclosure. Briefly, a metal ball can be coated with candle soot for 10 to 15 s and then dipped into PDMS. This candle soot layer is then transferred to PDMS by curing PDMS at 110° C. for 15 min. The CS-PDMS 5448 of SOAP is then obtained after removing the metal ball. The fabrication methods for all other SOAPs are described later on.

Figure 54E:
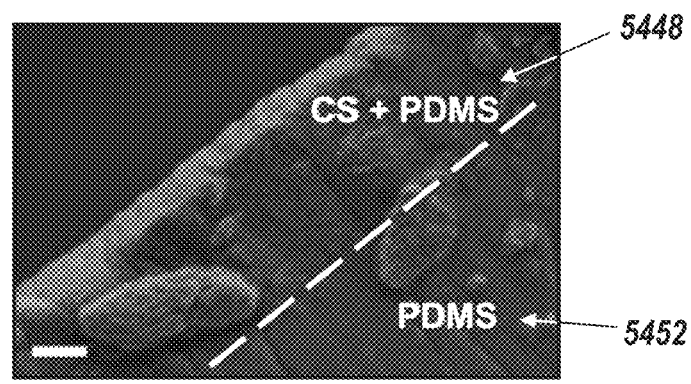
Figure 54F:
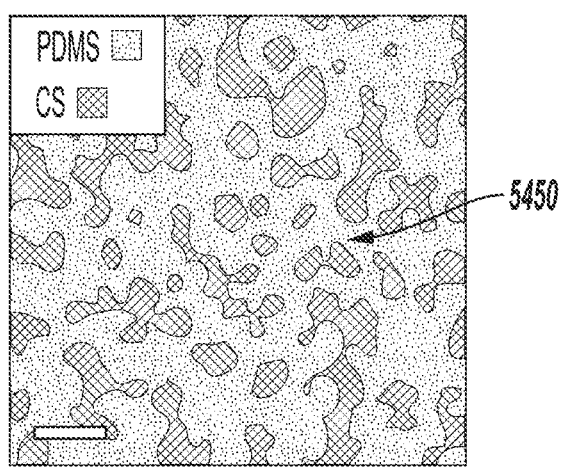

To investigate whether the transfer process produces a well-mixed matrix of CS and PDMS, the CS-PDMS 5448 of SOAP can be sliced to thin layers with a thickness of ~200 μm and exanimated the morphology by using a scanning electron microscopy (SEM). An evenly mixed layer composed of CS and PDMS, with a thickness of 2.7 μm, can be observed and separated from the pure PDMS layer 5452 in FIG. 54E, wherein the dashed line separated CS and PDMS mixture region and pure PDMS region, with scale bar: 1 μm. This thickness is very close to the theoretical thickness of 2.15 μm for the optimal optoacoustic transduction of CS-PDMS 5448. From the SEM image, the diameter of CS nanoparticles can be identified as ~55 nm. Additionally, the deposition rate of the CS layer 5452 was ~200 μm/s, which is also consistent with documented rates. Besides the morphology, the chemical composition of the structure of the CS-PDMS composite can be further studied by using stimulated Raman scattering (SRS) and photothermal imaging. The femtosecond SRS of C—H bonds in PDMS only occurs at a certain phase (here assigned as X channel) when the two beams temporally overlapped (t~0 s), while the candle soot's pump-probe signal (Y channel) occurs at almost all phases and has a much longer decay. Therefore, one pure CS 5454 sample and CS-PDMS 5448 sample can be prepared, and chemically distinguished the spatial distribution of the two materials. The merged image 5450 illustrates that a uniform matrix of CS and PDMS has been made via FIG. 54F, with a scale bar: 2 μm. Such a uniform mixture allows for rapid transfer of heat light-absorbing CS to PDMS, which is a foundation for efficient optoacoustic conversion.

Figure 54G:
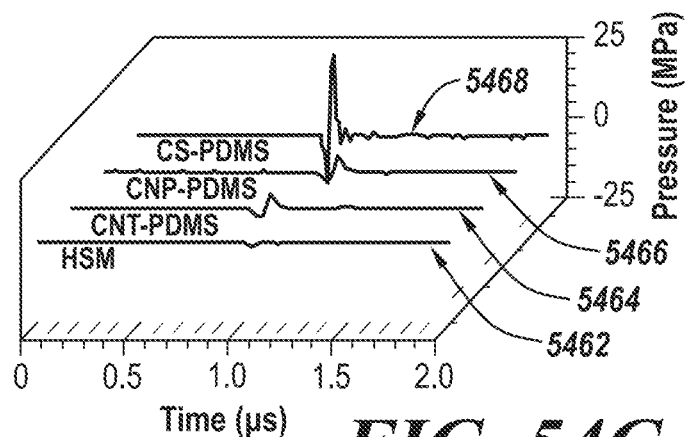
Figure 54H:
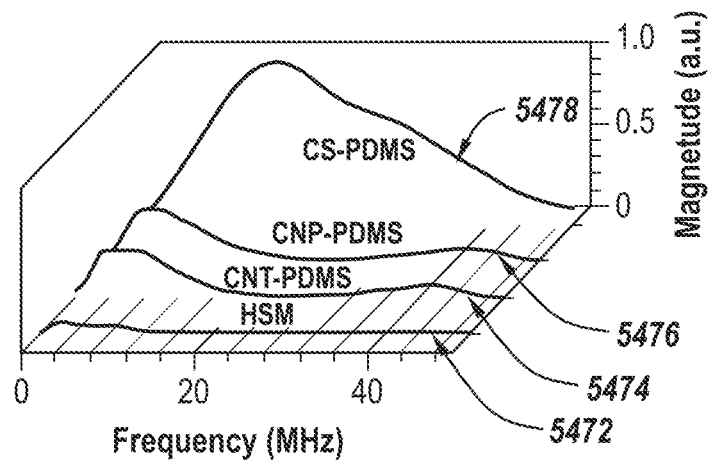

According to the exemplary embodiments herein, to characterize the optoacoustic efficiency of the four fabricated SOAPs, a 1064 nm pulsed laser with 8 ns pulse width can be delivered to each design to generate OFUS signals. The waveforms and pressure of the optoacoustic signals generated from each OFUS with 0.62 mJ/cm2 laser input were recorded by a needle hydrophone, as detailed in FIG. 54G. HSM graph line 5462 provided the smallest amplitude, 5 times smaller compared to CNT-PDMS graph line 5464 and CNP-PDMS graph line 5466. While signals from CNT-PDMS 5464 and CNP-PDMS 5466 were at the same level, CS-PDMS graph line 5468 generated ~48 MPa, which is 6-fold larger than them. This is consistent with previous efforts. After analyzing the waveform by the FFT transform, the frequency spectrum of the OFUS signal is obtained and detailed in FIG. 54H. HSM graph line 5472 had a central frequency at ~3 MHz, CNT-PDMS graph line 5474 and CNP-PDMS graph line 5476 had higher central frequency at ~5 MHz, while CS-PDMS graph line 5478 had the highest central frequency ~15 MHz, and ~6 dB widths defined at 5 and 35 MHz. Based on these characterizations, in some embodiments, CS-PDMS SOAP can be ideal to subject to further experiments, not only due to the highest optoacoustic conversion efficiency compared to the rest of SOAPs, but also because the broadest bandwidth can provide a tightest focus and shortest cycle duration for improved spatiotemporal control. In this way, CS-PDMS SOAP can be fabricated with demonstrable high NA, high focal gain, and board bandwidth at the focus for neural stimulation.

Figure 55A:
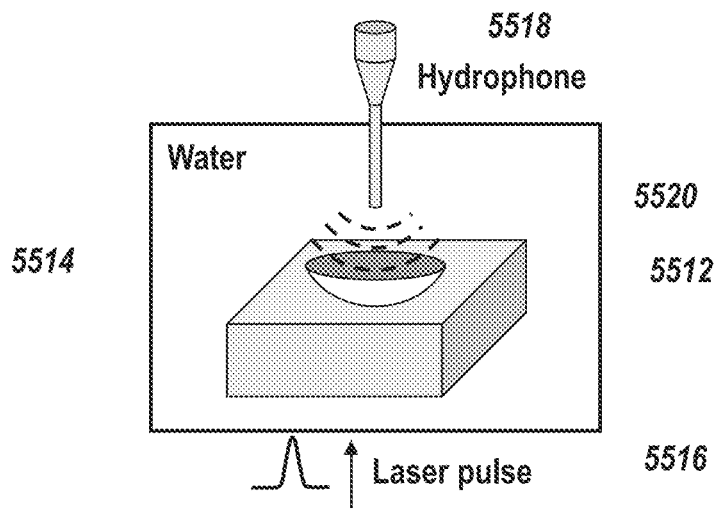
FIGS. 55A-55F illustrate transcranial efficiency and high spatial resolution of OFUS penetrating mouse skull.
Figure 55B:
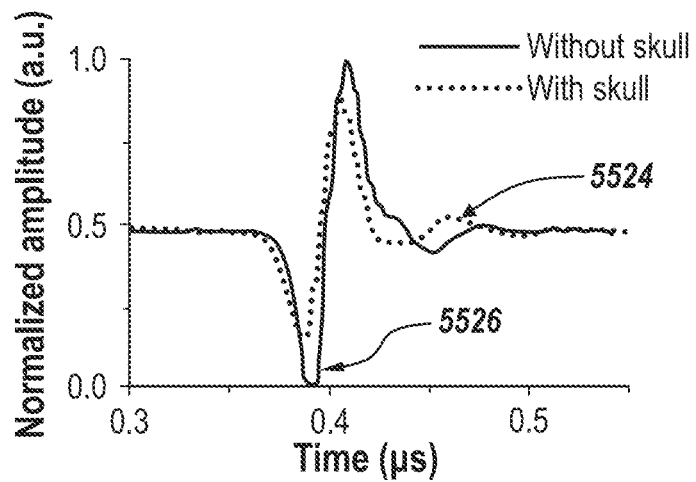
Figure 55C:
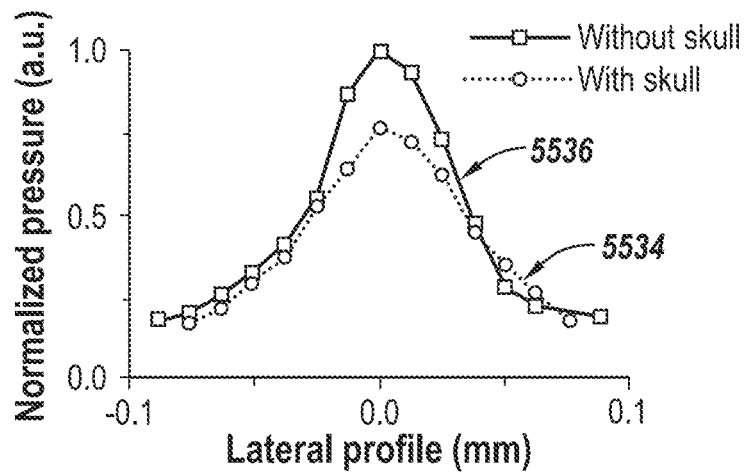
Figure 55D:
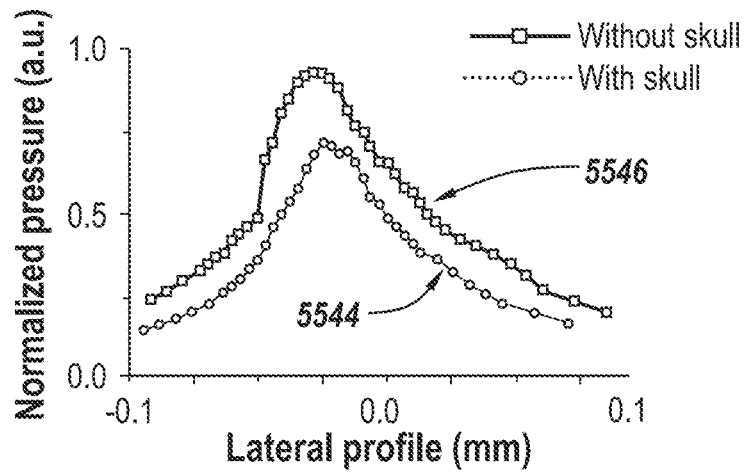

According to another aspect of the present disclosure, OFUS demonstrates high spatial resolution and transcranial efficiency. To demonstrate that OFUS can remain at high resolution after penetrating skulls for non-invasive applications, the spatial resolution of the CS-PDMS SOAP can be characterized before and after penetrating a piece of mouse skull. FIG. 55A is a schematic of the experimental setup for characterizing ultrasound generated by SOAP with a needle hydrophone. In FIG. 55A, the CS-PDMS SOAP 5512 is placed in a water tank 5514 illuminated with laser pulses 5516. A needle hydrophone 5518 is employed to acquire the ultrasound 5520 amplitude and profile from the top of SOAP 5512. For the transcranial ability test, the mouse skull can carefully be trimmed to the size of OFUS (thickness ~0.15 mm) and placed it between the hydrophone 5518 and OFUS. FIG. 55B is a graph of the normalized acoustic waveform generated by SOAP 5512 without and with mouse skull. The transcranial efficiency of OFUS can be calculated by comparing the amplitude of transcranial ultrasound signal to that of original signal, as illustrated in FIG. 55B. The transcranial signal is thereby normalized to the original one for a clear view. The transcranial efficiency for OFUS on mouse skull at graph line 5524 was 69%, which is significantly higher compared to 38% at graph line 5526 for 5 MHz conventional ultrasound transducer. This is due to the broad bandwidth of OFUS; while the high-frequency component was absorbed and reflected, the low-frequency component can still penetrate the skull. To characterize the focus size without and with mouse skull, the focus can be swept to acquire lateral and axial profiles, as detailed in FIGS. 55C and 55D. FIG. 55C is a graph of the lateral resolution of OFUS without and with mouse skull at graph lines 5536 and 5534 respectively. FIG. 55D is a graph of the axial resolution of OFUS without and with mouse skull at graph lines 5546 and 5544 respectively. The hydrophone 5518 is mounted to an XYZ translation stage and moved at the step of 12.7 μm to acquire the profile. All profiles were normalized to original profiles for comparison. Data in FIGS. 55C and 55D thereby show no obvious change in the profile after penetration of the mouse skull. Lateral and axial resolution are defined according to the full width at half maximum (FWHM) in the respective directions. The lateral and axial resolution of OFUS changed from 66 μm and 284 μm to 83 μm and 287 μm, respectively. The original resolutions of the OFUS are close to simulation data. It should be noted that these resolutions are two orders of magnitude more precise comparing to the resolution of low-frequency ultrasound typically used in ultrasound neuromodulation, which was ~5 mm and ~40 mm respectively for a 0.5 MHz transducer.

Figure 55E:
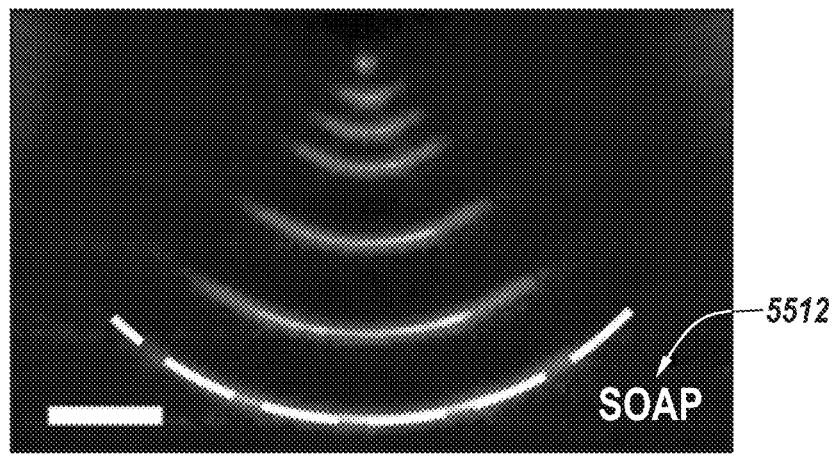
Figure 55F:
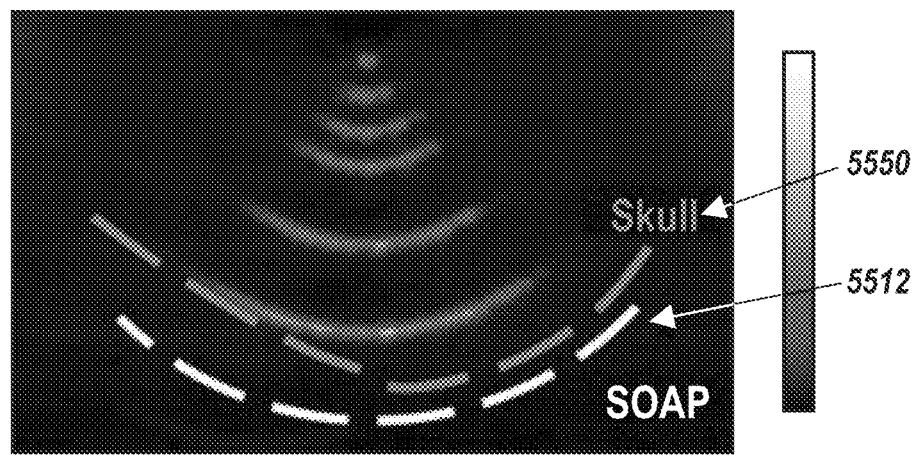

Continuing with the illustrative example, to examine the location of focal regions of OFUS, the propagation of ultrasound focus can be visualized by an optoacoustic tomography system. The laser pulse is delivered from the bottom of the SOAP 5512. The position of SOAP 5512, the mouse skull 5550, and the optoacoustic signal can be recorded by a 128-element ultrasound transducer array from the top. From the merged image, no significant change in the position of the focus was observed. FIGS. 55E-55F are images of the SOAP 5512-generated ultrasound propagation without (55E) and with (55F) skull 5550. The white dashed line indicates SOAP 5512; the dark dashed line identifies the mouse skull, and the scale bar is 2 mm. In FIGS. 55E-55F, by tuning the delay for the ultrasound transducer array, the propagation process of the OFUS can be reconstructed from the surface to the focus area. Images were scaled to the original propagation signal for comparison. These propagation results not only illustrate the interference process of optoacoustic signal to generate a tight focus, but also demonstrate that this process would not be influenced significantly by the existence of mouse skull and remain a tight transcranial focus.

Figure 56A:
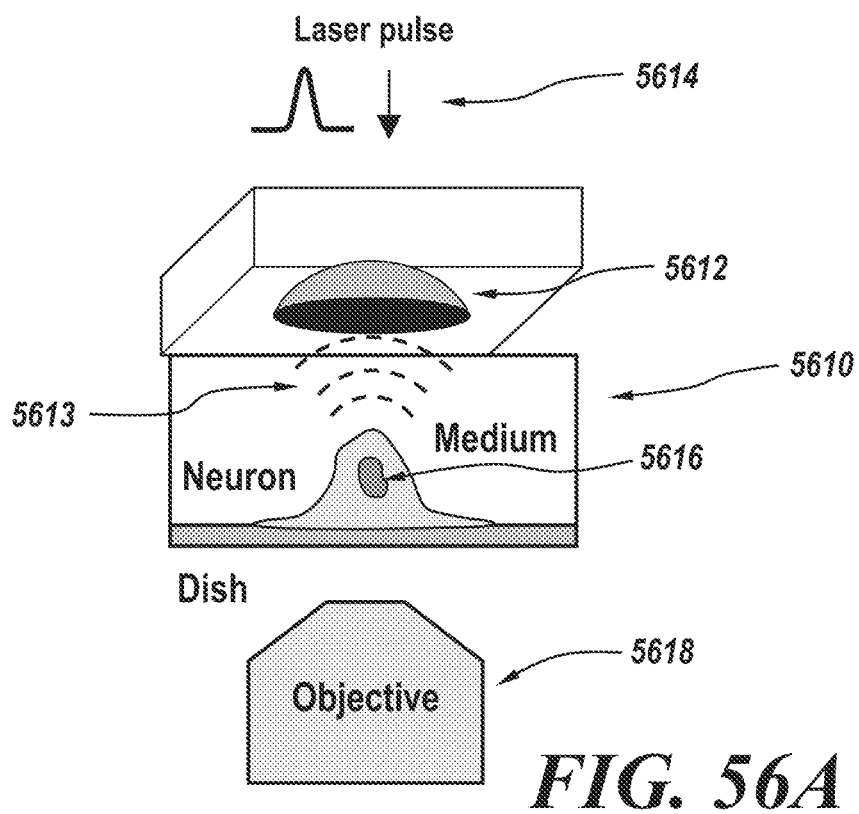
Figure 56B:
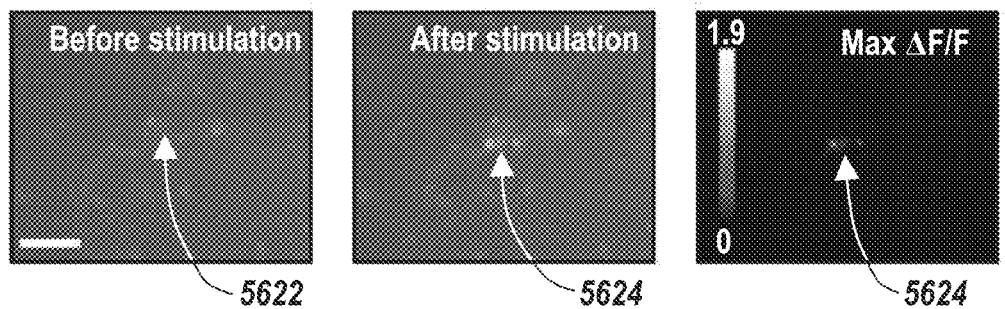
Figure 56C:
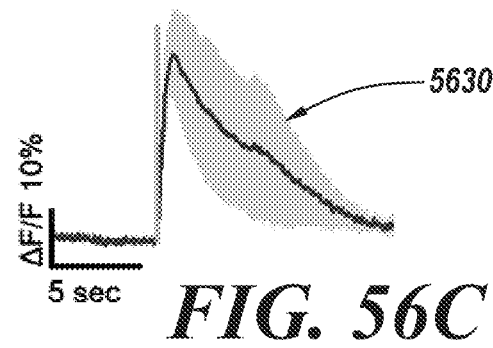
Figure 56D:
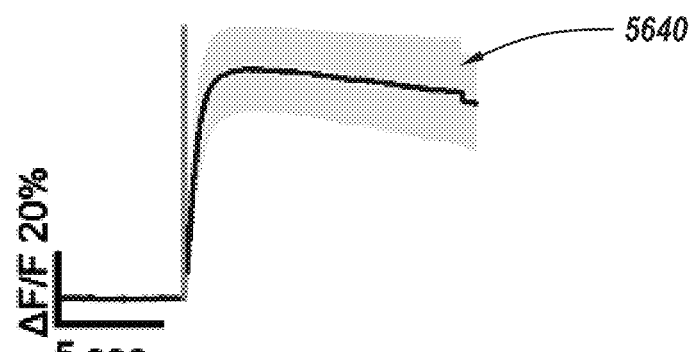
Figure 56E:
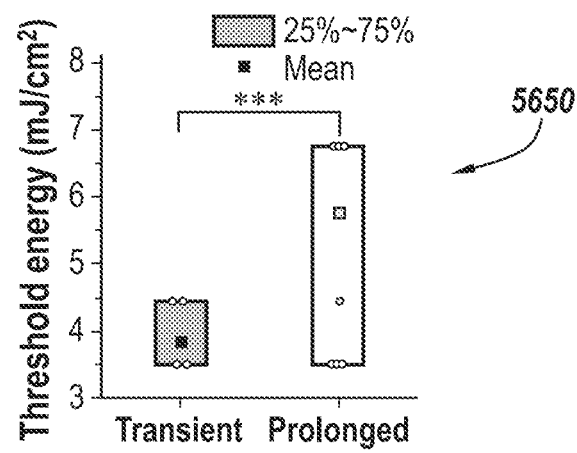

According to another aspect of the present disclosure, SOAP enables direct and transcranial stimulation of primary cortical neurons. With the demonstration of SOAP's high optoacoustic efficiency and tight transcranial focus, whether SOAP can evoke responses in cultured neurons can also be evaluated. As an illustrative example, primary cortical neurons from rats expressing GCaMP6f can be used for study in vitro. FIG. 56A is a schematic of direct in vitro stimulation experimental setup. The calcium signal can be recorded by a fluorescence imaging system 5610 consisting of an inverted wide-field microscope and a CMOS camera 5618, as presented in FIG. 56A. Before the experiment, the light path of the input laser 5614 should be aligned with the imaging system 5610. Then, the SOAP 5612 is mounted by a customized holder to an XYZ translation stage, and carefully adjusted to align with the light path of the input laser 5614. The SOAP can be placed ~2 mm above the cultured neuron 5616. To locate the focus in XY direction, 9.9 μm fluorescent beads can be used as indicators. When the laser 5614 is on, the position of the ultrasound focus can be visualized by the movement of beads due to acoustic radiation force. Based on the beads' movement, the focus of diameter is identified at around 100 μm, which is consistent with the tested lateral resolution. For neural stimulation, a single pulse of 1064 nm with 8 ns pulse width can be delivered, which generates a single cycle of optoacoustic signal. Following this, calcium traces from 37 neurons were recorded and analyzed (N=7 dishes). FIG. 56B shows a representative image of observed calcium transient with an input laser energy of 3.5 mJ/cm2 before and after stimulation at 5622 and 5624, respectively. The rightest panel shows the maximum ΔF/F at 5626. The neuron activation is only observed at the center of the field of view and the rest showed no response, which demonstrated a localized stimulation ability of SOAP with submillimeter spatial resolution. Among 37 neurons, two types of response can be observed: transient response and prolonged response. FIG. 56C is a graph of averaged calcium traces of a transient dynamic. In FIG. 56C, those two responses are separated at a decay time constant of 5 s. The transient responses show a decay time constant of τ=4.2 s. Responses were observed by way of graph line 5630 at the focus immediately after laser onset with max ΔF/F of 31%±8% (N=6 from 3 cultures, data in mean±SD), indicating a successful single-cycle stimulation. This single cycle lasts 0.26 μs. The duty cycle of a single-cycle stimulation is defined to be the cycle duration in one second. OFUS provides a super low duty cycle of $2.6 \times 10^{-4}$%. The prolonged responses have a time constant of $\tau=7.8$ s. For these neurons, a max $\Delta F/F$ of 62%±12% is observed right after the laser onset in FIG. 56D (N=31 from 4 cultures). FIG. 56D is a graph of averaged calcium traces of a prolonged dynamic of OFUS stimulation. Therein, the vertical line indicates OFUS stimulation, and the mean trace in solid and standard error of the mean in shaded at graph line 5640. These activations are observed not only at the focus, but also propagated through the network. To understand the phenomenon of different dynamics, the threshold for each response can be studied. The input laser energy is started low and increased until the neuron response is recorded. FIG. 56E is a graph detailing statistics of the threshold energy of the transient and prolonged stimulation. FIG. 56E thereby shows the averaged threshold to evoke transient and prolonged activations at 5650. The threshold for a transient response is 3.8±0.5 mJ/cm2, significantly lower than that of a prolonged response, which is 5.7±1.8 mJ/cm2 (two-sample t-test, N=37 from 7 cultures, ***$p<0.001$). Such an ability of neurons differentiates the magnitude of mechanical stimuli and response to higher amplitude stimulation with a longer time constant agrees well with several reports.

Figure 56F:
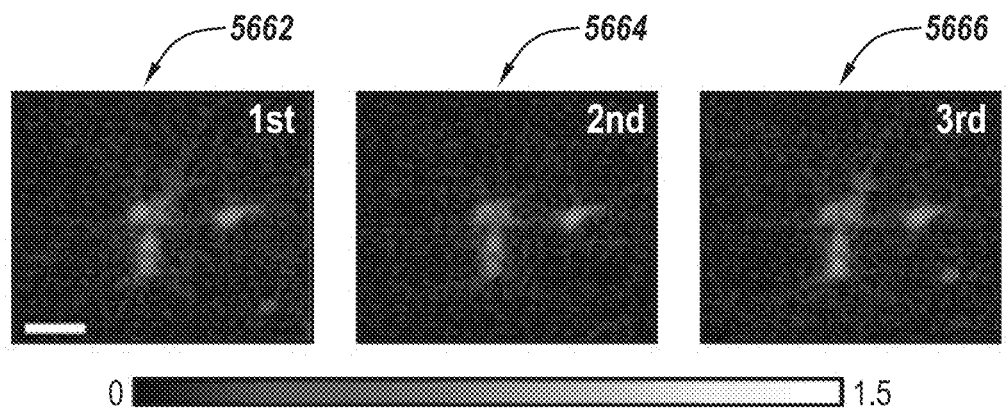

Continuing with the illustrative example, to demonstrate the safety of neural stimulation with SOAP, whether neurons can be stimulated repeatedly is also presented. In this way, single-cycle stimulations can be delivered at the same group of neurons for 3 times with an interval of 2 min. The laser energy was 3.5 mJ/cm$^2$. FIG. 56F shows images of maximum IF/F for each stimulation at a scale bar of 50 μm, with no visible deformation or damage in morphology observed in images 5662, 5664, or 5666, respectively. FIG. 56G is a graph presenting the corresponding calcium traces. Traces with a similar amplitude of max IF/F were recorded at graph line 5670, which demonstrated that no functional damage of the neuron was observed after repeated stimulation. The viability of neurons was further demonstrated after repeated stimulation at 6.5 mJ/cm$^2$ and 8.4 mJ/cm$^2$. Those two energy levels were selected 70% higher than the threshold to leave extra margin for the safety demonstration. Five groups of neurons were thereby studied at each energy level. For each group, 10 pulses were delivered with an interval of 5 s. In each pulse, 3 cycles at 10 Hz were included. To calculate cell viability, live and dead cells can be counted within an area of 200×200 μm$^2$ at the focus after 30 min incubation. No light group was performed as a control. As a result, no significant difference was observed in the cell viability between the stimulated group and the control group. These data collectively show that OFUS can stimulate neurons repeatedly and reliably, without any damage to the morphology or functionality of neurons.

Notably, the total energy needed to evoke a similar amplitude of neural response for SOAP is several orders of magnitude less compared to the conventional ultrasound. Neural stimulation is performed with a 0.5 MHz conventional focused ultrasound transducer in exactly the same experimental setup as the SOAP experiments in vitro. The process started with low ultrasound intensity and a short duration of continuous wave (CW) ultrasound. Then, the intensity can be increased along with duration step by step until a neural response with max $\Delta F/F>10$% is recorded. As an illustrative example, an ultrasound intensity of $3.02 \times 10^4$ W/cm$^2$ with 500 ms duration was demonstrated to evoke a calcium response up to 18% in the experimental setup. Compared to the conventional transducer, SOAP evokes neuron response at a similar level with six orders of magnitude less energy in exactly the same situation. FIG. 57 is a table including the experimental conditions and total energy to evoke similar amplitude of neuron response. Even compared to previous works with a conventional transducer to evoke ~15% calcium response, SOAP delivered two orders of magnitude less energy, as provided in Table 5700 of FIG. 57. This demonstrates the high stimulation efficiency of SOAP with a unique single-cycle stimulation mode that benefits from the optoacoustic effect.

Figure 58B:
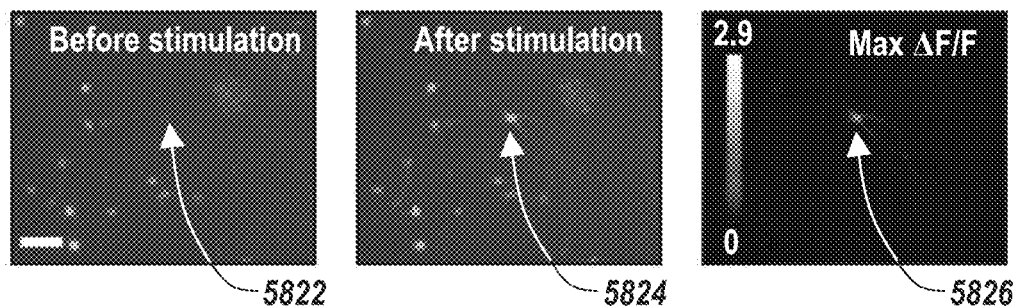
Figure 58C:
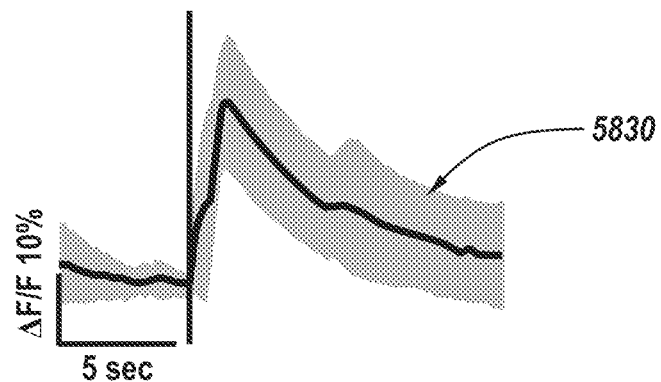
Figure 58D:
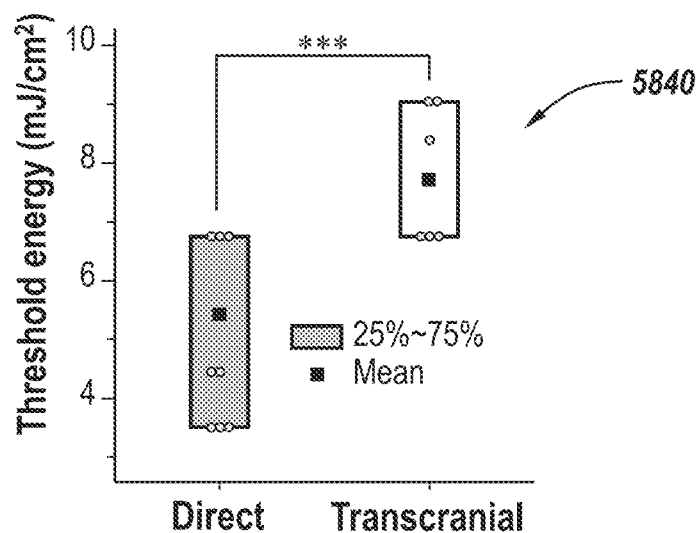

According to another aspect of the present disclosure, to test the transcranial stimulation capability, neural stimulation by OFUS can be further studied by penetrating a piece of mouse skull. FIG. 58A is a schematic of transcranial in vitro stimulation experimental setup 5810. As an illustrative example, a piece of mouse skull 5812 was embedded in the curvature of SOAP 5814. SOAP 5814 was illuminated from the top by laser pulse 5811, and the fluorescence imaging of GCaMP6f neuron 5816 was recorded from the bottom of the cell culture dish by camera 5818. The ultrasound focus 5813 was aligned by the translation stage and fluorescent beads as previously described. Accordingly, FIG. 58B shows the representative images and video of calcium signal before and after transcranial stimulation by OFUS, and corresponding max $\Delta F/F$ image at 5822 and 5824, respectively. The rightest panel shows the maximum $\Delta F/F$ at 5826, with a scale bar of 50 μm used throughout. Only the neuron in the middle of the field of view was activated, confirming that the transcranial focus was still tight for high-precision stimulation. With a single cycle stimulation by OFUS, successful stimulations with max $\Delta F/F$ of 27%±5% were recorded (N=18 from 7 cultures) by way of graph line 5830 in FIG. 58C, which is a graph of averaged calcium response trace of transcranial OFUS stimulation. Therein, the vertical line indicates OFUS stimulation, and the mean trace in solid and standard error of the mean in shaded. The thresholds for direct stimulation and transcranial stimulation were compared in FIG. 58D, which is a graph detailing statistics of threshold energy of direct and transcranial stimulation with single pulse. While the average threshold for direct stimulations was 5.4±1.5 mJ/cm2, the transcranial stimulation had a threshold of 7.7±1.1 mJ/cm2 (two-sample t-test, N=46 from 11 cultures, ***$p<0.001$). This increase of laser energy due to attenuation of penetrating mouse skull was consistent with our previous result for 69% of transcranial efficiency for OFUS. Collectively, these results demonstrate the ability of OFUS to stimulate cortical neurons both directly and transcranially.

Figure 59A:
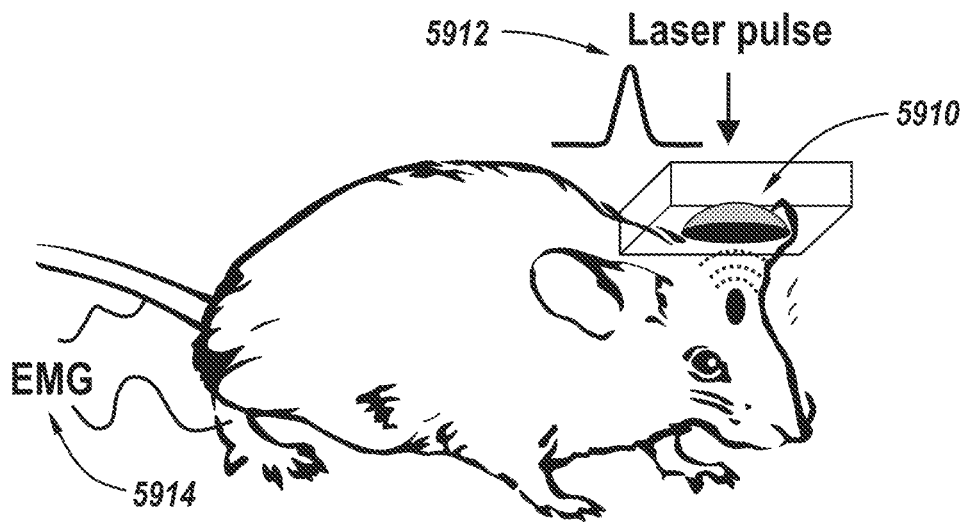
FIGS. 59A-59F illustrate representative immunofluorescence examinations with the OFUS stimulation and EMG recording trace.
Figure 59B:
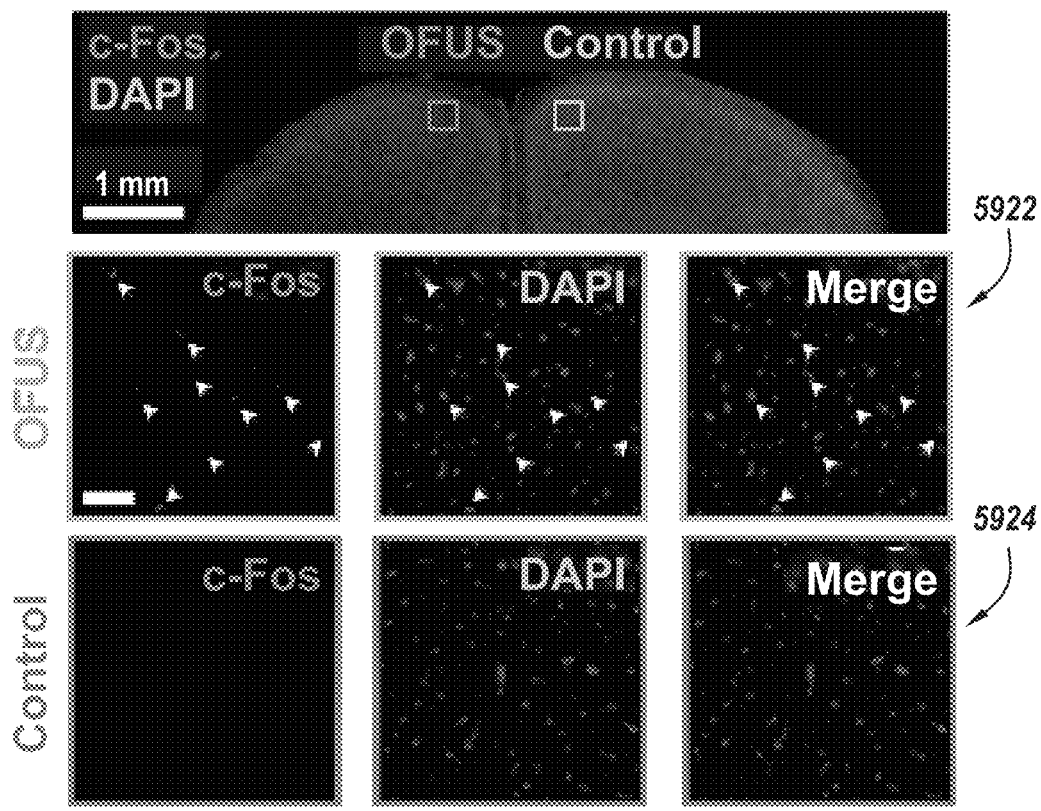
Figure 59C:
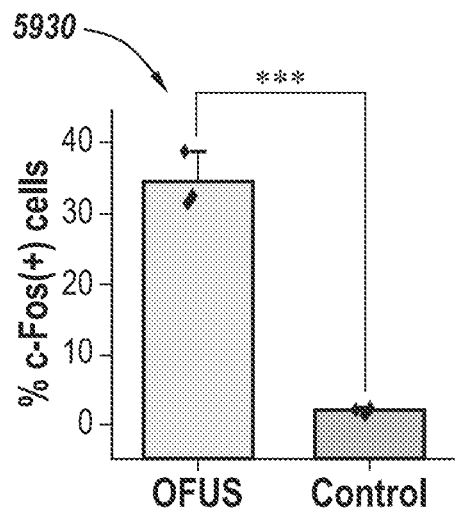

According to another aspect of the present disclosure, OFUS mediates high-precision neural stimulation in vivo. With successful stimulation of cultured neurons directly and transcranially, the present disclosure also includes whether OFUS can activate neurons in living animals. As an illustrative example, adult C57BL/6J mice were used for stimulation in vivo, and the effect of stimulation was evaluated by immunofluorescence method and electrophysiology recording. Mice were deeply anesthetized with isoflurane and shaved to expose the scalp. FIG. 59A is a schematic of experimental setup of OFUS stimulation in vivo. A CS-PDMS SOAP 5910 was mounted to a customized 3D-printed holder and attached it to an XYZ translation stage. The input laser 5912 was delivered from the top, and the focus of generated ultrasound was carefully aligned with the motor cortex based on stereotaxic coordinates (Medial-Lateral: 1.5, Anterior-Posterior: 0.5). Accordingly, FIG. 59B is a set of images of c-Fos and DAPI staining within the stimulation 5922 and control area 5924. For reference in clockwise order, c-Fos, DAPI, and merge comprise the OFUS stimulated area 5922, and the control group below at 5924 with the c-Fos, DAPI, and merge views respectively at contralateral area; scale bar: middle and lower panel, 50 µm. First, the stimulated area is visualized by labeling c-Fos protein in stimulated neurons. To induce robust c-fos expression, OFUS stimulation is applied with laser energy of 1.0 mJ/cm$^2$ (corresponding to a peak-to-peak pressure of 39 MPa) for a pulse train of 20 pulses at 10 Hz, which lasted 30 min with a 33% duty cycle. The mice were put to rest for 1 h to maximize c-Fos expression. The mouse brain was then extracted and fixed in 10% formalin for 24 h. Brain slices of 150 µm thick were stained with c-Fos and DAPI and imaged with a confocal microscope. c-Fos positive cells observed at the OFUS-stimulated area 5922 were more than the control group 5924 at the contralateral area. The percentage of c-Fos positive cells in OFUS group 5922 and the control group 5924 was then calculated. FIG. 59C is a graph 5930 with statistical analysis for percentage of c-Fos positive neurons. The percentage was significantly increased in OFUS group compared to the control (two-sample t-test, n=3, ***p<0.001). Importantly, the c-Fos signal was confined to an area of ~200 µm in diameter, demonstrating superior spatial resolution compared to conventional piezo-transducer-based transcranial ultrasound stimulation (1~5 mm). Moreover, the c-Fos expression was confined at the target site. The size of this area was close to the focus size of OFUS. This demonstrates the expression of c-Fos was induced by the focus of OFUS directly. No significant c-Fos expression outside the targeted area due to indirect stimulation was observed. These results confirm the ability of OFUS to directly evoke responses of neurons non-invasively with high spatial resolution.

Figure 59D:
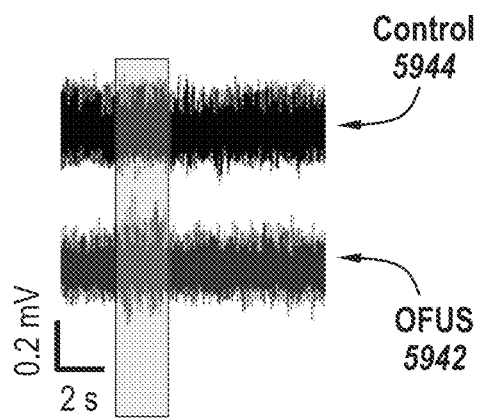
Figure 59E:
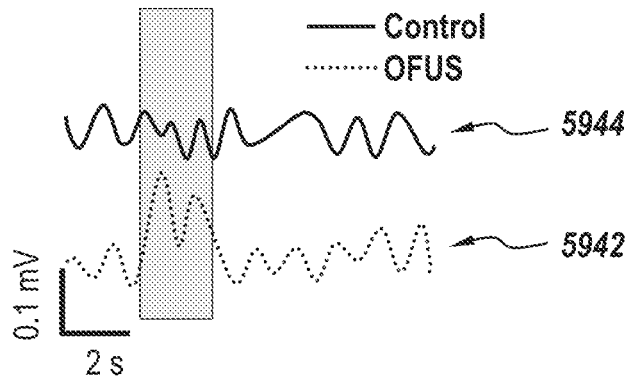

Continuing with the illustrative example, further evaluation of the functional outcome by OFUS stimulation was conducted with the electromyography (EMG) method. The focus of SOAP 5910 was aligned to the primary motor cortex of the mouse brain to evoke cramps of muscles. To record muscle activities, the EMG electrode 5914 was inserted parallel to the biceps femoris muscle into the hind limb, and the ground electrode was inserted into the tail, as detailed in FIG. 59A. As a result, laser pulse train with a duration of 2 s at 1.0 mJ/cm$^2$ was delivered to SOAP 5910 and strong EMG responses (0.458±0.03 mV) were recorded at the same time from the contralateral hind limb by way of FIG. 59D, which is a representative EMG recording of 2 s OFUS stimulation 5942 and no light control group 5944 (box: Laser pulse train). It should be noted that those EMG signals have a typical delay of ~61±6 ms between laser onset and EMG response. After processing with a bandpass filter and full-wave rectifier, the envelope of the EMG signal was plotted in FIG. 59E, which is a representative EMG signal after band-pass filter and full-wave rectifier and envelope also gauging OFUS stimulation 5942 and no light control group 5944. As a control to eliminate the possibility of EMG response evoked by the auditory effect of ultrasound, the somatosensory cortex was stimulated based on stereotaxic coordinates. No significant response was observed. This result suggests that the EMG response is evoked directly by OFUS stimulation but not an auditory effect of ultrasound.

Figure 59F:
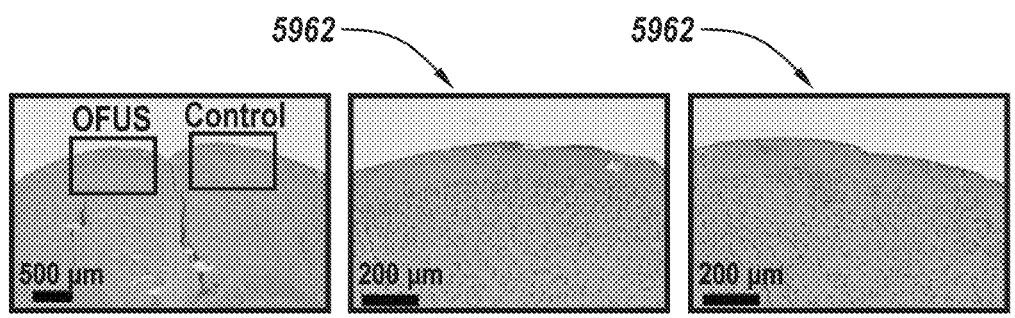

According to another aspect of the present disclosure, the safety of OFUS stimulation by hematoxylin and eosin (H&E) staining can be evaluated. As an illustrative example, after the EMG recording, mice were sacrificed, and brains were extracted and fixed. Brain slices of 5 µm thick with were obtained every 150 µm and standard H&E staining was performed. All of the brain slices were then examined by a slice scanner and compared between targeted area and the control group at contralateral area. FIG. 59F is a set of images detailing histology results after stimulation in vivo for safety evaluation for OFUS group 5962 and control group 5964. Therein, no significant change in morphology of cells between those groups was observed. This illustrated that the OFUS stimulation does not induce visible damage to mouse brains.

According to the illustrative examples provided by the present disclosure, the ultrasound field generated by SOAP was simulated by an open-source k-Wave toolbox on MATLAB R2019b (MathWorks, MA) in 2D. No absorption was considered during the simulation. SOAP was delivering ultrasound into the water as the propagation medium. The backing material was set to air. The density and acoustic speed were defined accordingly.

According to the illustrative examples provided by the present disclosure, to fabricate the HSM-SOAP 5442, to form a curvature, a piece of heat-shrink tubing (McMaster-Carr, 6363K214) was filled with a steel bead with a diameter of 12.7 mm (McMaster-Carr, 9529K22), and heated up with a heat gun to fully shrink. After that, the tubing can be cut 2 mm away from the great circle of the steel bead and to obtain an HSM-SOAP.

According to the illustrative examples provided by the present disclosure, to fabricate the CNT-PDMS 5444 and CNP-PDMS SOAP 5446, 5 wt % multi-wall carbon nanotubes (VWR, MFCD06202029) and CNP (Sigma-Aldrich, 633100-25G) were mixed with the PDMS base and curing agent matrix (10:1 weight ratio, Dow Corning Corporation, Sylgard 184) respectively. The mixture was poured into a 3D-printed mold designed with 12.7 mm diameter and 2 mm focal distance and degassed in vacuum for 30 min. To get fully cured CNT-PDMS and CNP-PDMS samples, the mixture was heated in an oven to 60° C. for 2.5 hrs before being obtained from the mold.

According to the illustrative examples provided by the present disclosure, to fabricate the CS-PDMS 5448, a steel bead with a diameter of 12.7 mm was placed at the flame core of a paraffin wax candle for 10 to 15 s to be fully coated with flame synthesized candle soot nanoparticles. Then, the coated bead was dipped into the degassed PDMS base and curing agent matrix (10:1 weight ratio), and adjusted to leave the surface of the PDMS matrix 2 mm lower than the great circle plane of the bead. The cured sample was obtained after 15 min heating at 110° C. on a heat plate.

According to the illustrative examples provided by the present disclosure, ultrasound generation and characterization involved a Q-switched Nd: YAG laser (Quantel Laser, CFR ICE450) with 8 ns pulse at 1064 nm was delivered to SOAP to generate an optoacoustic signal. The laser was modulated by a function generator (33220A, Agilent) at a repetition rate of 10 Hz. A system consisting of a 40 µm needle hydrophone (Precision Acoustic, MH0040, optimized for 5 to 40 MHz range), a submersible preamplifier, and a DC coupler was used for the ultrasound pressure and profile measurement. The signal was then amplified with an ultrasonic pulser-receiver (Olympus, Model 5073PR) and collected with a digital oscilloscope after 4 times average (Rigol, DS4024). As the needle hydrophone has a tip smaller than the generated focus, the acquired data $P_{peak}$ only reflected part of the pressure in focus. To get an estimation of the real pressure over the ultrasound focus, a 25.4 µm step was taken to map out the pressure over the FWHM of the focus area. The data was averaged to get spatially averaged pressure $P_{averaged}$, and a coefficient C was obtained by the following equation $$C = \frac{P_{averaged}}{P_{peak}}.$$

After the pressure reached the upper dynamic limit of the hydrophone, we recorded current pressure $P_0$, moved the hydrophone out of focus to avoid signal saturation and device damage. The recorded pressure is $P_{0\text{-}out}$. Then, the laser energy was increase and recoded a pressure $P_{x\text{-}out}$. The pressure at the focus $P_x$ generated by current energy input could be estimated by the following equation $$P_x = \frac{P_x}{P_{0-out}} P_0,$$

due to constant spatial pressure distribution. The final estimated spatially averaged pressure would be acquired by multiplying $P_x$ with coefficient C.

According to the illustrative examples provided by the present disclosure, before SEM imaging (Zeiss, Supra 55VP), thin cross-section slices of SOAP were sputtered with Au/Pd for 10 s and mounted on an aluminum stub. SEM images of SOAP are obtained at 3 kV as accelerating voltage with an aperture size of 20 microns.

According to the illustrative examples provided by the present disclosure, SRS and photothermal imaging involved an 80-MHz femtosecond pulsed laser (Spectra-Physics, InSight X3) provides a tunable beam (from 680 nm to 1300 nm) and a synchronized beam (fixed at 1045 nm) for the multimodal imaging system. To image the PDMS and candle soot, the tunable beam was set to 801 nm as the pump beam, along with the fixed wavelength beam as the Stokes for femtosecond stimulated Raman scattering (SRS) microscopy for C—H bond and also the probe beam for pump-probe microscopy for candle soot simultaneously. After the Stokes/probe beam was modulated by an acoustic-optic modulator (Isomet Corporation, 1205c), two beams were combined by a dichroic mirror and directed into a lab-built laser scanning microscope. The temporal delay between two beams was controlled by a motorized delay stage. A 60× water objective (Olympus, UPlanApo 60XW, NA=1.2) focused the collinear beams onto the sample. The power of each beam on the sample is 2 mW. The two beams were collected in the forward direction by an oil condenser (Olympus, Aplanat Achromat 1.4, NA=1.4) and then filtered by short pass filters. After filtering, only the pump beam was detected by a photodiode with a laboratory-built resonant amplifier. A phase-sensitive lock-in amplifier (Zurich Instrument, MFLI) demodulated the detected pump beam for the stimulated Raman loss signal and the pump-probe signal according to the modulation transfer. Therefore, an x-y-t image can be measured for the composition.

According to the illustrative examples provided by the present disclosure, an optoacoustic tomography system consists of a customized 128-element transducer array (L22-14v, Verasonics Inc., 50% bandwidth) and a 128-channel ultrasound data acquisition system (Vantage 128, Verasonics Inc.). The PAT system is synchronized with Quantel by a function generator and a delay generator (DG535, Stanford Research Systems). The function generator triggered Quantel and the delay generator with pulse mode at 10 Hz repetition rate. The delay generator added another tunable delay to the Vantage 128 to receive ultrasound signal at different time delays after the optoacoustic signal is generated. By tuning the delay, a propagation process of the optoacoustic signal can be visualized.

According to the illustrative examples provided by the present disclosure, embryonic neuron culture involved 35 mm glass-bottomed dishes coated with 50 μg/ml poly-D-lysine (Sigma-Aldrich) in an incubator at 37° C. with 5% $CO_2$ overnight and washed with sterile $H_2O$ three times before seeding the neuron. Primary cortical neurons were derived from Sprague-Dawley rats (E18) of either sex and digested in papain (Thermo Fisher Scientific Inc.). A medium with 10% heat-inactivated fetal bovine serum (FBS, Atlanta Biologicals), 5% heat-inactivated horse serum (HS, Atlanta Biological), 2 mM Glutamine Dulbecco's Modified Eagle Medium (DMEM, Thermo Fisher Scientific Inc.) was used for washing and triturating dissociated cells. Cells were cultured in cell culture dishes (100 mm diameter) for 30 min at 37° C. in a humid incubator to eliminate fibroblasts and glial cells. The supernatant containing neurons was collected and seeded in poly-D-lysine coated dishes with 10% FBS+ 5% HS+2 mM glutamine DMEM medium. After 16 h, replaced the medium with Neurobasal medium (Thermo Fisher Scientific Inc.) containing 2% B27 (Thermo Fisher Scientific Inc.), 1% N2(Thermo Fisher Scientific Inc.), and 2 mM glutamine (Thermo Fisher Scientific Inc.). 5 μM 5-fluoro-2'-deoxyuridine (Sigma-Aldrich) and AAV9.Syn.Flex.GCaMP6f.WPRE.SV40 virus (Addgene, MA, USA) at 1 μl/ml final concentration was added to the medium at day 5, for preventing glial proliferation and expressing GCaMP6f, respectively. 50% of the medium was replaced with a fresh culture medium every 3-4 days, and neurons were used for stimulation after 10-13 days.

According to the illustrative examples provided by the present disclosure, OFUS stimulation in vitro involved the SOAP mounted on a 3D-printed holder to a translation stage for fine adjustment of the device position. The Quantel laser was delivered to SOAP in free space for optoacoustic signal generation. An inverted microscope (Eclipse TE2000-U, Nikon) with 10×objective (Plan Fluor, 0.3 NA, 16 mm WD, Thorlabs), illuminated by a 470-nm LED (M470L2, Thorlabs), filtered by a filter set for fluorescent protein (MDF-GFP, Thorlabs), imaged with a CMOS camera (Zyla 5.5, Andor), was used for fluorescence imaging. Before stimulation, the focus of ultrasound was visualized by 9.9 μm fluorescent beads (G1000, Duke Scientific Corp) and adjusted to the center of the field of view. Then SOAP was dipped into neuron culture dish at the same position in X and Y direction, and 2 mm above the neuron in the Z direction. The camera was synchronized with the laser. While the camera was recording at 20 Hz for 20 s, the laser was delivered at 5th second. The fluorescence intensities in imaging sequences were analyzed with ImageJ (Fiji) after experiments.

According to the illustrative examples provided by the present disclosure, for cell viability studies, five groups of neuron were randomly selected in each dish at each energy level. Meanwhile, a dish of neuron was delivered 30 pulses of OFUS in total at selected energy level. Every 3 consecutive cycles were delivered at 10 Hz with an interval of 5 s. The live and dead cells were calculated within an area of 200×200 μm2 at the focus. All the neurons were labelled with GCaMP6f. The dead cells were stained with 1 μL 100 μg/Ml propidium iodide (P1304MP, Thermo Fisher Scientific Inc.) solution for 15 min. The cells were incubated for 30 min before imaged with fluorescence microscope for analysis.

According to the illustrative examples provided by the present disclosure, OFUS stimulation in vivo involved adult C57BL/6J mice (age 14-16 weeks) initially anesthetized with 5% isoflurane in oxygen and then fixed on a standard stereotaxic frame with 1.5~2% isoflurane. A tail pinch was used to determine the anesthesia depth. A heating pad was placed under the mouse to maintain the body temperature. The hair on the targeted brain was removed. SOAP mounted on a 3D-printed holder was aligned to the targeted motor cortex of the mouse. The Quantel laser was delivered to SOAP in free space at a 10 Hz repetition rate. For c-fos expression, a pulse train was delivered with 33% duty cycle (2 s laser on, 4 s laser off) for 30 min. For EMG recording, a pulse train of 2 seconds was delivered.

According to the illustrative examples provided by the present disclosure, EMG recording and processing involved aligning SOAP with the primary motor cortex. To record the muscle activity, the needle electrode was inserted subcutaneously into the hind limb biceps femoris muscle and the ground electrode was inserted into the footpad. The control group was recorded on the trunk ipsilateral to the stimulation site. EMG signals were recorded by a Multi-Clamp 700B amplifier (Molecular Devices), filtered at 1 to 5000 Hz, digitized with an Axon DigiData 1,550 digitizer (Molecular Device), and filtered by a noise eliminator (D-400, Digi-timer). EMG signal was filtered with bandpass filter at 0.5~500 Hz and full-wave rectification. Then the envelope of the processed signal was plotted.

According to the illustrative examples provided by the present disclosure, immunofluorescence staining involved after the stimulation session, the mouse was put to rest for 1 h for maximized c-fos expression, then was sacrificed and perfused transcardially with phosphate-buffered saline (PBS, 1×, PH 7.4, Thermo Fisher Scientific Inc.) solution and 10% formalin. After fixation, the brain was extracted and fixed in 10% formalin solution for 24 hrs. The fixed mouse brain was immersed in 1×PBS solution. The brain was sliced to coronal sections with 150 μm thickness with an Oscillating Tissue Slicer (OST-4500, Electron Microscopy Sciences). Brain slices were gently transferred by a brush into 10% formalin solution for another 24 h fixation, then blocked with 5% Bovine serum albumin (Sigma-Aldrich)-PBS solution for 30 min at room temperature. The slices were permeabilized with 0.2% Triton (Triton X-100, 1610407, Bio-Rad Laboratories)-PBS solution for 10 min, and incubated with Anti c-Fos Rabbit antibody (4384S, Cell Signaling Technology) at a concentration of 2 μg/mL at 4° C. overnight. Following primary incubation, slices were incubated with secondary antibody Alexa Fluor 488 goat anti-rabbit IgG (Thermo Fisher Scientific) at a concentration of 1 μg/mL and DAPI (Thermo Fisher Scientific) at 5 μg/mL in dark for 2 h at room temperature. Between steps, the slices were rinsed with 0.2% Tween (Tween 20, Tokyo Chemical Industry)-PBS solution 4 times for 5 min. Fluorescent images were acquired with an FV3000 Confocal Laser Scanning Microscope (Olympus). Confocal images were acquired under an excitation wavelength of 405 nm for DAPI and 488 nm for c-Fos.

According to the illustrative examples provided by the present disclosure, histology staining involved after the stimulation session, the mouse was sacrificed immediately, and perfused and fixed as previously described. The brain was embedded in paraffin and sliced for 5 μm thickness at 150 μm step to obtain coronal sections. Slicing and standard H&E staining were performed at Mass General Brigham Histopathology Research Core. Histology images were acquired with a VS120 Automated Slide Scanner (Olympus).

According to the illustrative examples provided by the present disclosure, a thermal couple (DI-245, DataQ) was used to record the temperature profile. The tip of the thermal couple was placed at the focus, the surface of SOAP respectively. The laser with energy of 6.2 mJ/cm2 was turned on for 10 s at 10 Hz during recording. A group of no light at the surface was also recorded as a baseline.

According to the illustrative examples provided by the present disclosure, regarding statistical analysis, acoustic waveforms, calcium traces, and electrophysiological traces were plotted with Origin 2020. FFT transforms for the frequency spectrum were performed with MATLAB R2019b. Data are presented with the mean±standard error of the mean. Calcium images are processed with ImageJ. All comparative data are analyzed with a two-sample t-test. p values were defined as: n.s., not significant ($p>0.05$); * $p<0.05$;  $p<0.01$; * $p<0.001$.

It should be noted that the biosafety of OFUS is a crucial for successful neuromodulation. In these illustrative examples, biosafety was evaluated by cell viability after repeated stimulation in vitro and histological imaging in vivo where no damage was concluded. Additionally, cavitation and thermal accumulation are two major potential bioeffects of ultrasound exposure. To evaluate the safety, the mechanical index was calculated and tested the temperature rise of OFUS. With the laser input for in vivo experiment, the estimated peak-to-peak pressure 39 MPa delivered to the mouse brain is below the level in which no tissue lesion was reported previously. The peak negative pressure of OFUS was measured to be 18 MPa, which is below the threshold of generating bubble cloud in soft tissue (25-30 MPa). Acoustic attenuation coefficient for brain tissue of 0.91 dB/(cm×MHz) [53] were used to estimate the MI and calculated MI=3.3 of OFUS stimulation. In comparison, short-pulse ultrasound exposure with a pulse duration of 1.4 μs at MI=3.9 has been reported with rare cavitation-related damage in brain tissue. Thus, the shorter pulse duration of 0.26 μs and lower MI of the illustrative embodiments should be well below the damage threshold for tissue cavitation. For thermal safety, the temperature profiles were recorded with thermal sensor. The laser energy of 6.2 mJ/cm$^2$ was applied, which matched the highest energy threshold used according to the illustrative examples relating to this aspect of the present disclosure. OFUS was delivered for 10 s and tested at the focus of OFUS, the surface of SOAP, and a control group without light at the surface of SOAP. A maximum temperature rise of 0.4 K was observed at the surface after 10 s heating. Therefore, with longest duration of 2 s, no significant temperature rise >0.1 K can be induced at the focus of OFUS in this work. Furthermore, the highest possible temperature rise is still far below the threshold required to modulate neuron activities ($\Delta T \geq 5$ K) [55] and will not damage cells. Therefore, OFUS has been demonstrated to be safe for tissue both by biological and physical evidence.

According to the illustrative examples of this aspect of the present disclosure, a CS-PDMS SOAP was developed, and generated OFUS, characterized the spatial resolution and transcranial ability, and validated the submillimeter transcranial neural stimulation in vitro and in vivo. The large NA from the optoacoustic effect allowed a tight focus at 66 μm, which is beyond the reach of the piezo-based low-frequency ultrasound. The broadband emission allowed a transcranial efficiency of 69% of OFUS penetrating a piece of mouse skull. Direct and transcranial stimulations of GCaMP6f labeled rat cortical neurons in vitro were recorded with fluorescent imaging. The total ultrasound energy input of OFUS to evoke neural response is two to six orders of magnitudes lower than conventional ultrasound, providing a high stimulation efficiency. Successful non-invasive stimulation at the motor cortex of living mice in vivo by OFUS was demonstrated by the immunofluorescence method and EMG recording. The safety of OFUS stimulation was evaluated both in vitro and in vivo by cell viability and histology biologically, and by MI and temperature rise physically.

It should be noted that an important observation about OFUS stimulation is that the stimulation was evoked by the direct effect of the acoustic wave instead of indirect effects, e.g. auditory confounding effect. In experiments in vitro, cultured neurons were responding to the OFUS stimulation without auditory circuits. In studies in vivo, c-Fos positive neurons were located at the stimulation site corresponding to the direct stimulation. Moreover, no response was recorded in the control group which was stimulated at the somatosensory cortex in EMG recording, indicating that the bone conduction to the cochlear was not involved in the process. Such observation agrees with reported direct stimulation with ultrasound.

According to the exemplary embodiments herein, SOAP is a device providing a single fixed ultrasound field. While complex brain functions are not controlled by a single site, multisite stimulation provides more possibilities in modulation and therapies. It can deliver patterned neuromodulation, which, for example, can further provide selectivity in motor control for therapy. On the strength of flexibility of the fabrication process, the OFUS device can scale up to a massive array for multisite neuromodulation. For conventional PZT-based ultrasound massive array, the massive cabling connected to each element is fabricated with copper to minimize electromagnetic interference, which further impedes the application of a wearable clinical device. On the contrary, a light-weighted OFUS device provides improved comfort for long-term treatment. Such a device without any metal components further offers improved compatibility with real-time magnetic resonance imaging (MRI) guidance and functional MRI monitoring. These benefit the closed-loop of real-time multisite stimulation and treatment evaluation in clinical application.

Notably, OFUS can offer high ultrasound intensity by simply improving the energy of input light. It offers an opportunity for OFUS to be applied for ultrasound treatment in lieu of conventional high intensity focused ultrasound (HIFU). For example, histotripsy delivers low frequency (<3 MHz), short pulses (<10 cycles) of high intensity ultrasound (>20 MPa) into tissue for cavitation-based therapy. However, HIFU needs high voltage to reach a certain intensity, which meanwhile leads to a narrow bandwidth (<30%), a long ringdown time (>5 cycles), and a risk of dielectric breakdown[70]. OFUS generated by SOAP has been demonstrated with high frequency, high intensity, precise single-cycle control, and a broad bandwidth of 200%. This niche highlights a future direction of OFUS application in ultrasound surgery with improved spatiotemporal control and minimized damage and heat accumulation to surrounding tissue.

According to the exemplary embodiments of the present disclosure, OFUS generated by SOAP harnesses submillimeter precision non-invasively towards neurological research in small animals and brain sub-regions. Its flexibility in fabrication, high spatiotemporal resolution and intensity, and improved electromagnetic compatibility further allow clinical applications, such as ultrasound surgery, drug delivery, and pain management. This work thus underlines the profound potential for OFUS to be utilized as a valuable platform technology in neuroscience research and clinical therapies.

Whereas many alterations and modifications of the disclosure will become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A tapered fiber optoacoustic emitter (TFOE) comprising:
   a nanosecond laser configured to emit laser pulses; and
   an optic fiber with a tip, the optic fiber configured to guide the laser pulses, the tip having a coating including a diffusion layer and a thermal expansion layer,
   wherein:
      the diffusion layer comprises epoxy and zinc oxide nanoparticles configured to diffuse the light while restricting localized heating around the diffusion layer;
      the thermal expansion layer comprises carbon nanotubes (CNTs) and Polydimethylsiloxane (PDMS) configured to convert the laser pulses to generate ultrasound; and
      a frequency of the ultrasound is determined based on a thickness of the diffusion layer and a CNT concentration of the thermal expansion layer.

2. The device of claim 1, wherein the ultrasound comprises omnidirectional acoustic waves generated locally at the tip through the optoacoustic effect when excited by the laser pulses.

3. The device of claim 2, wherein the omnidirectional acoustic waves are localized within a sub-100 micron distance from the tip.

4. The device of claim 3, wherein the omnidirectional acoustic waves are configured to activate single neurons of a subject.

5. The device of claim 4, wherein the omnidirectional acoustic waves allow for optoacoustic stimulation and simultaneous monitoring of cell response in the subject using whole cell patch clamp recording.

6. The device of claim 1, wherein the device further comprises tuning the frequency by varying a thickness of the diffusion layer or a CNT concentration of the thermal expansion layer, to induce cell membrane sonoporation in effected cells of a subject.

7. The device of claim 6, wherein the frequency of the ultrasound is tuned by varying a thickness of the diffusion layer or a CNT concentration of the thermal expansion layer to provide controllable frequencies in the range of 0.083 MHz-5.500 MHz.

8. The device of claim 7, wherein the coating is a single layer nano-composite mixed from 5% to 15% (w/w) multi-wall carbon nanotube in Polydimethylsiloxane.

9. A method of operating a tapered fiber optoacoustic emitter (TFOE) comprising:
emitting laser pulses with a nanosecond laser and guiding the laser pulses with an optic fiber having a tip, the tip coated with a diffusion layer comprising epoxy and zinc oxide and a thermal expansion layer comprising carbon nanotubes (CNTs) and Polydimethylsiloxane (PDMS);
diffusing the laser pulses while restricting localized heating, around the diffusion layer;
converting the diffused light to generate ultrasound, with the thermal expansion layer; and
tuning a frequency of the ultrasound based on a thickness of the diffusion layer and a CNT concentration in the expansion layer.

10. The method of claim 9, wherein the ultrasound comprises omnidirectional acoustic waves generated locally at the tip through the optoacoustic effect when excited by the laser pulses.

11. The method of claim 10, wherein the omnidirectional acoustic waves are localized within a sub-100 micron distance from the tip.

12. The method of claim 11, wherein the omnidirectional acoustic waves are configured to activate single neurons of a subject.

13. The method of claim 12, wherein the omnidirectional acoustic waves allows for optoacoustic stimulation and simultaneous monitoring of cell response in the subject using whole cell patch clamp recording.

14. The method of claim 9, wherein the method further comprises tuning the frequency, by varying a thickness of the diffusion layer or a CNT concentration of the thermal expansion layer, to induce cell membrane sonoporation in effected cells.

15. The method of claim 14, wherein the frequency of the ultrasound is tuned by varying a thickness of the diffusion layer or a CNT concentration of the thermal expansion layer to provide controllable frequencies in the range of 0.083 MHz-5.500 MHz.

16. The method of claim 9, wherein the coating is a single layer nano-composite mixed from 5% to 15% (w/w) multi-wall carbon nanotube in Polydimethylsiloxane.

17. A tapered fiber optoacoustic emitter (TFOE), comprising:
a nanosecond laser configured to emit laser pulses; and
an optic fiber with a tip, the optic fiber configured to guide the laser pulses, the tip having a coating including a thermal expansion layer, wherein:
the thermal expansion layer comprises carbon nanotubes (CNTs) and
Polydimethylsiloxane (PDMS) configured to convert the laser pulses to generate ultrasound,
wherein embedding CNT into a fibroin hydrogel forms an optoacoustic film, the fibroin hydrogel configured to stimulate neural growth in a subject in response to ultrasound; and
the frequency of the ultrasound is tuned based on a thickness of the CNT concentration of the expansion layer.

18. The device of claim 17, wherein the tip further comprises a diffusion layer.

19. The device of claim 18, wherein the diffusion layer comprises epoxy and zinc oxide nanoparticles configured to diffuse the light while restricting localized heating around the diffusion layer.

20. The device of claim 19, wherein the frequency of the ultrasound is tuned by varying a thickness of the diffusion layer.

21. The device of claim 17, wherein the optoacoustic film is flat.

22. The device of claim 17, wherein the optoacoustic film is curved.

23. The device of claim 22, wherein the curved optoacoustic film generates a focused ultrasound for non-invasive modulation.

* * * * *